United States Patent
Bertani et al.

(10) Patent No.: US 7,727,988 B2
(45) Date of Patent: Jun. 1, 2010

(54) AZABICYCLO[3.1.0]HEX-3-YL}ALKYL) PYRIMIDINEDIONE

(75) Inventors: Barbara Bertani, Verona (IT); Giorgio Bonanomi, Verona (IT); Anna Maria Capelli, Verona (IT); Anna Checchia, Verona (IT); Romano Di Fabio, Verona (IT); Gabriella Gentile, Verona (IT); Fabrizio Micheli, Verona (IT); Alessandra Pasquarello, Verona (IT); Giovanna Tedesco, Verona (IT); Silvia Terreni, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 311 days.

(21) Appl. No.: 11/693,756

(22) Filed: Mar. 30, 2007

(65) Prior Publication Data
US 2007/0249642 A1  Oct. 25, 2007

(30) Foreign Application Priority Data

Apr. 3, 2006 (GB) ................. 0607892.7
Jan. 9, 2007 (GB) ................. 0700363.5
Feb. 21, 2007 (GB) ................. 0703404.4

(51) Int. Cl.
C07D 401/14 (2006.01)
A61K 31/513 (2006.01)
(52) U.S. Cl. .................. 514/252.02; 514/255.05; 514/274; 544/238; 544/295; 544/310
(58) Field of Classification Search ................. 544/238, 544/295, 310; 514/252.02, 255.05, 274
See application file for complete search history.

(56) References Cited

U.S. PATENT DOCUMENTS

| 6,096,755 | A | 8/2000 | Steiner | 514/279 |
| 6,204,284 | B1 | 3/2001 | Beer et al. | 514/412 |
| 2006/0235004 | A1 | 10/2006 | Geneste et al. | 514/218 |
| 2007/0142438 | A1 | 6/2007 | Arista et al. | 514/341 |
| 2009/0054449 | A1 | 2/2009 | Geneste et al. | 514/252.18 |
| 2009/0221618 | A1 | 9/2009 | Arista et al. | 514/274 |

FOREIGN PATENT DOCUMENTS

| WO | WO 2006/108701 | 10/2006 | ................. 403/6 |
| WO | WO 2006/133946 | 12/2006 | ................. 403/12 |
| WO | WO2007/113258 | 10/2007 | |
| WO | WO2007/113260 | 10/2007 | |

OTHER PUBLICATIONS

Le Foll, et al., PubMed Abstract (Expert Opin Investig Drugs, 16(1):45-57), Jan. 2007.*
Bio Med Chem Lett, 2006, 16, 1934-1937.
Bio Med Chem Lett, 2006, 490-494.

* cited by examiner

*Primary Examiner*—Deepak Rao
(74) *Attorney, Agent, or Firm*—James M. Kanagy; Edward R. Gimmi; Charles M. Kinzig

(57) ABSTRACT

The present invention relates to novel compounds of formula (I)' or a salt thereof:

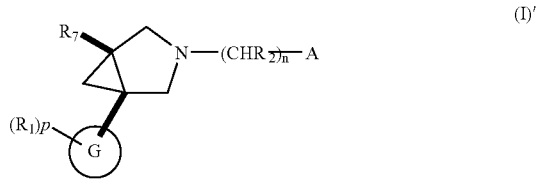

wherein
G is selected from a group consisting of: phenyl, a 5- or 6-membered monocyclic heteroaryl group, or a 8- to 11-membered heteroaryl bicyclic group;
A is a group P1 or a group P2 wherein
P1 is

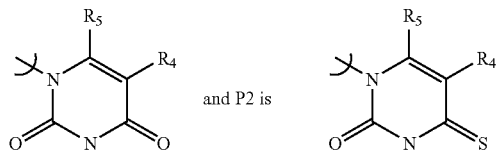

and the other groups are define in herein.

6 Claims, No Drawings

AZABICYCLO[3.1.0]HEX-3-YL}ALKYL)PYRIMIDINEDIONE

The present invention relates to novel compounds, processes for their preparation, intermediates used in these processes, pharmaceutical compositions containing them and their use in therapy, as modulators of dopamine $D_3$ receptors.

Recently a patent application has been published as WO2005/080382 and discloses the compounds of the following formula or salts thereof:

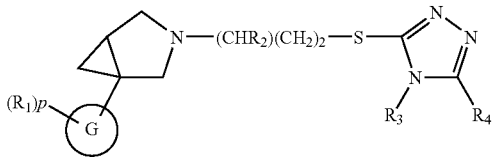

wherein
G is selected from a group consisting of: phenyl, pyridyl, benzothiazolyl, indazolyl;
p is an integer ranging from 0 to 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;
$R_2$ is hydrogen or $C_{1-4}$alkyl;
$R_3$ is $C_{1-4}$alkyl;
$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl;
$R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;

and when $R_1$ is chlorine and p is 1, such $R_1$ is not present in the ortho position with respect to the linking bond to the rest of the molecule; and when $R_1$ corresponds to $R_5$, p is 1.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

The present invention provides a compound of formula (I) or a salt thereof:

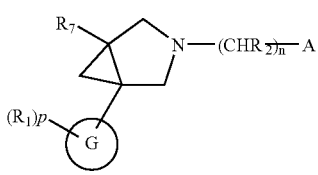

(I)

wherein
G is selected from a group consisting of: phenyl, a 5- or 6-membered monocyclic heteroaryl group, or a 8- to 11-membered heteroaryl bicyclic group;
A is a group P1 or a group P2
wherein
P1 is

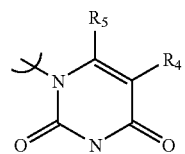

and P2 is

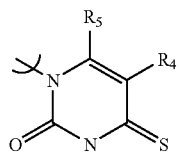

p is an integer ranging from 0 to 5;
$R_1$ is halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_6$; and when p is an integer ranging from 2 to 5, each $R_1$ may be the same or different;
$R_2$ is hydrogen or $C_{1-4}$alkyl;
n is 3, 4, 5 or 6;
$R_6$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such $R_6$ group is optionally substituted by one or two substituents selected from: halogen, cyano, $C_{1-4}$alkyl, halo$C_{1-4}$alkyl, $C_{1-4}$alkoxy, $C_{1-4}$alkanoyl;
$R_4$ is selected in the group consisting of: hydrogen, halogen, hydroxy, cyano, $C_{1-4}$alkyl, $C_{3-7}$ cycloalkyl, halo$C_{1-4}$ alkyl, $C_{1-4}$alkoxy, halo$C_{1-4}$alkoxy, $C_{1-4}$alkanoyl and NR'R"; or $R_4$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl, halo$C_{1-4}$alkoxy and $SF_5$;
$R_5$ is selected in the group consisting of: hydrogen, halogen, hydroxy, cyano, $C_{1-4}$alkyl, $C_{3-7}$ cycloalkyl, halo$C_{1-4}$ alkyl, $C_{1-4}$alkoxy, halo$C_{1-4}$alkoxy, $C_{1-4}$alkanoyl and NR'R"; or $R_5$ is a phenyl group, a 5-14 membered heterocyclic group; and any of such phenyl or heterocyclic groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl and $SF_5$;
$R_7$ is hydrogen or $C_{1-2}$alkyl;
R' is H, $C_{1-4}$ alkyl or $C_{1-4}$ alkanoyl;
R" is defined as R';
R' and R" taken together with the interconnecting nitrogen atom may form a 5-, 6-membered saturated or unsaturated heterocyclic ring;

wherein at least one of $R_4$ and $R_5$ is hydrogen; and wherein only one $R_2$ group may be different from hydrogen.

Because of the presence of the fused cyclopropane, compounds of formula (I) are believed to have a "cis" disposition of the substituents (both groups linked to the bicyclic ring system are on the same face of this bicyclic ring system).

In one embodiment of the present invention compounds of formula (I)' are provided which correspond to the compounds of formula (I), or salts thereof, having "cis" disposition, represented by the bold highlight of the bonds

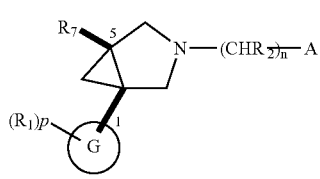

(I)' wherein G, A, p, n, $R_1$, $R_2$, and $R_7$ are defined as above for compounds of formula (I).

It will be appreciated that compounds of formula (I)' possess at least two chiral centres, namely at position 1 and 5 in the 3-azabicyclo[3.1.0]hexane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In compounds of formula (I)' there are at least two chiral centres, which are located in the cyclopropane portion, as depicted below (the bold highlight of the bonds means the "cis" configuration); through optical resolution of a mixture containing the two stereoisomers which are enantiomers with respect to the chiral centres in the cyclopropane, single stereoisomers of compounds of formula (I)' may be obtained as shown in the scheme below:

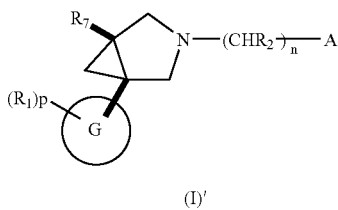

(I)'

↓ Resolution

-continued

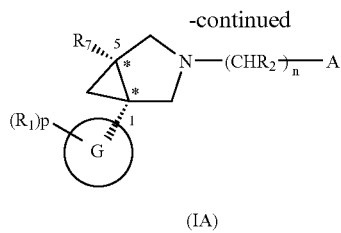

(IA)

Absolute configuration of chiral center at position named 1 and 5 may be assigned using Cahn-Ingold-Prelog nomenclature based on groups' priorities.

In one embodiment of the present invention compounds of formula (IA) are provided that correspond to stereochemical isomers of compounds of formula (I)', enriched in configuration shown in the picture below at chiral centers at position named 1 and 5:

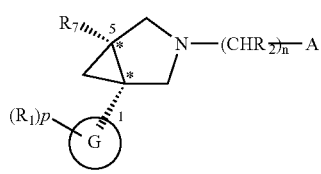

(IA)

wherein G, A, p, n, $R_1$, $R_2$, and $R_7$ are defined as above for compounds of formula (I), or a salt thereof.

It is intended in the context of the present invention that stereochemical isomers of formula (IA) enriched in one configuration at centers named 1 and 5, correspond in one embodiment to at least 90% e.e. (enantiomeric excess). In another embodiment the isomers correspond to at least 95% e.e. In another embodiment the isomers correspond to at least 99% e.e.

In another embodiment of the present invention compounds of formula (IH) are provided that correspond to stereochemical isomers of compounds of formula (I)', enriched in configuration (1S,5R) or (1R,5R)

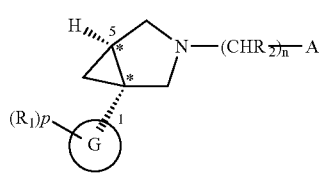

(IH)

wherein G, A, p, n, $R_1$ and $R_2$ are defined as above for compounds of formula (I) and $R_7$ is hydrogen, or a salt thereof.

Different nomenclature for absolute configuration assigned to chiral center named 1 [(1R) or (1S)] may be generated by different meanings for G group.

For example, when the group G is a phenyl group, absolute configuration nomenclature for compounds of formula (IH) is (1S,5R).

It is intended in the context of the present invention that stereochemical isomers enriched in configuration (1S,5R) or (1R,5R) of formula (IH) correspond in one embodiment to at least 90% e.e. (enantiomeric excess). In another embodiment the isomers correspond to at least 95% e.e. In another embodiment the isomers correspond to at least 99% e.e.

In another embodiment of the present invention the stereochemical isomers enriched in configuration (1R,5S) are provided.

In another embodiment of the present invention compounds of formula (IL) are provided that correspond to stereochemical isomers of compounds of formula (I)', enriched in configuration shown in the picture below at chiral centers at position named 1 and 5:

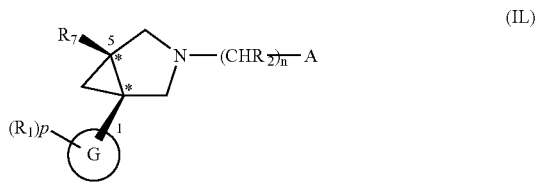

(IL)

wherein G, A, p, n, $R_1$, $R_2$ and $R_7$ are defined as above for compounds of formula (I), or a salt thereof.

The term '$C_{1-4}$ alkyl' as used herein as a group or a part of the group refers to a linear or branched alkyl group containing from 1 to 4 carbon atoms; examples of such groups include methyl, ethyl, propyl, isopropyl, n-butyl, isobutyl, tert butyl.

The term '$C_{3-7}$ cycloalkyl group' as used herein means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term '$C_{1-4}$ alkoxy group' as used herein may be a linear or a branched chain alkoxy group, for example methoxy, ethoxy, propoxy, prop-2-oxy, butoxy, but-2-oxy or methyl-prop-2-oxy and the like.

The term '$C_{1-4}$ alkanoyl group' as used herein may be a linear or a branched chain alkanoyl group, for example acetyl, ethylcarbonyl, n-propylcarbonyl, i-propyl carbonyl, n-butylcarbonyl or t-butylcarbonyl and the like.

The term 'halogen' as used herein refers to a fluorine, chlorine, bromine or iodine atom.

The term 'halo $C_{1-4}$ alkyl' as used herein means an alkyl group having one or more carbon atoms and wherein at least one hydrogen atom is replaced with halogen such as for example a trifluoromethyl group and the like.

The term 'halo $C_{1-4}$ alkoxy group' as used herein may be a $C_{1-4}$ alkoxy group as defined before substituted with at least one halogen, preferably fluorine, such as $OCHF_2$, or $OCF_3$.

The term 'aryl' as used herein means an aromatic carbocyclic moiety such as phenyl, biphenyl or naphthyl.

The term '5,6-membered monocyclic heteroaryl' as used herein means an aromatic monocyclic heterocycle ring of 5 or 6 members and having at least one heteroatom selected from nitrogen, oxygen and sulfur, and containing at least 1 carbon atom.

Representative 5, 6 membered monocyclic heteroaryl groups include (but are not limited to): furyl, thiophenyl, pyrrolyl, pyridyl, oxazolyl, isooxazolyl, pyrazolyl, imidazolyl, thiazolyl, isothiazolyl, pyridazinyl, pyrimidinyl, pyrazinyl, triazinyl, triazolyl and tetrazolyl.

The term '8, 11-membered bicyclic heteroaryl' as used herein means an aromatic bicyclic heterocycle ring of 8 to 11 members and having at least one heteroatom selected from nitrogen, oxygen and sulfur, and containing at least 1 carbon atom.

Representative 8, to 11 membered bicyclic heteroaryl groups include (but are not limited to): benzofuranyl, benzothiophenyl, indolyl, isoindolyl, azaindolyl, quinolinyl, isoquinolinyl, benzoxazolyl, benzimidazolyl, benzothiazolyl, quinazolinyl and phthalazinyl.

The term 5-14 membered heterocycle means a 5 to 7-membered monocyclic, or 7-to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a physiologically acceptable anion or cation. Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations.

In one embodiment, $R_1$ is halogen, cyano, acetyl, trifluoromethyl or trifluoromethoxy.

In another embodiment, $R_1$ is trifluoromethyl.

In one embodiment, $R_2$ is hydrogen. In another embodiment $R_2$ is $C_{1-4}$ alkyl (e.g. methyl).

In one embodiment $R_4$ is hydrogen, $C_{1-4}$alkyl, halo$C_{1-4}$ alkyl, $C_{1-4}$alkoxy, halo$C_{1-4}$alkoxy, $C_{1-4}$alkanoyl, halogen, phenyl or hydroxy.

In another embodiment $R_4$ is hydrogen, $C_{1-4}$alkyl (for example methyl), halogen (for example fluorine), halo$C_{1-4}$ alkyl (for example trifluoromethyl), an optionally substituted 5-14 membered heterocycle (for example optionally substituted thiophenyl, pyrrolidinyl, pyridinyl, isoxazolyl, pyridazinyl, oxazolyl, pyrazinyl), optionally substituted phenyl, cyano or $C_{3-7}$ cycloalkyl (for example cyclopropyl).

In a further embodiment, $R_4$ is an optionally substituted phenyl or 5, 6-membered heteroaryl group (for example optionally substituted thiophenyl, pyridinyl, isoxazolyl, pyridazinyl, oxazolyl, pyrazinyl).

In one embodiment $R_5$ is hydrogen, $C_{1-4}$alkyl, halo$C_{1-4}$alkyl, $C_{1-4}$alkoxy, halo$C_{1-4}$alkoxy, $C_{1-4}$alkanoyl, phenyl, hydroxy or halogen.

In another embodiment $R_5$ is hydrogen.

In one embodiment, $R_6$ is a group selected from: isoxazolyl, 2-pyrrolidinonyl, —CH$_2$—N-pyrrolyl, 1,1-dioxido-2-isothiazolidinyl, 2-thienyl, 2-pyridyl, 2-thiazolyl which is optionally substituted by one or two substituents selected from: halogen, cyano, $C_{1-2}$alkyl (e.g. methyl), halo$C_{1-2}$alkyl (e.g. trifluoromethyl), $C_{1-2}$alkoxy (e.g. methoxy), $C_{1-3}$alkanoyl (e.g. acetyl).

In one embodiment, G is phenyl.

In one embodiment $R_7$ is hydrogen or methyl.

In another embodiment $R_7$ is hydrogen.

In one embodiment, p is 0, 1 or 2.

In another embodiment, p is 1.

In one embodiment, n is 3 or 4.

In another embodiment, $R_4$ is hydrogen, methyl, hydroxy, phenyl or fluorine.

In another embodiment, $R_5$ is hydrogen.

In another embodiment, $R_6$ is isoxazolyl, 2-pyrrolidinonyl, -1,1-dioxido-2-isothiazolidinyl.

In another embodiment, $R_7$ is hydrogen.

In one embodiment, A is a group $P_1$.

In another embodiment, p is 1 and $R_1$ is trifluoromethyl.

In one embodiment, a compound of formula (IB) or a salt thereof is provided, wherein $R_1$, $R_2$, $R_4$, $R_5$, p, n, and $R_7$ are as defined for formula (I):

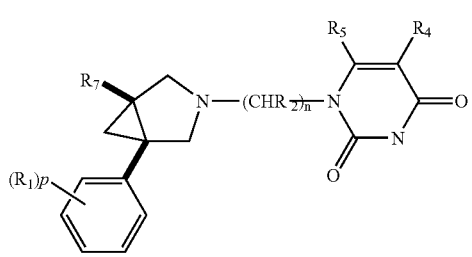
(IB)

In Formula (IB), in one embodiment, n is 3 or 4, p is 1, $R_1$ is trifluoromethyl, $R_2$ is hydrogen, $R_4$ is hydrogen, methyl, hydroxy, fluorine or an optionally substituted phenyl or 5,6-membered heteroaryl group, $R_5$ is hydrogen and $R_7$ is hydrogen.

In another embodiment, a compound of formula (IG) or a salt thereof is provided, wherein $R_1$, $R_2$, $R_4$, $R_5$, p, n, and $R_7$ are as defined for formula (I):

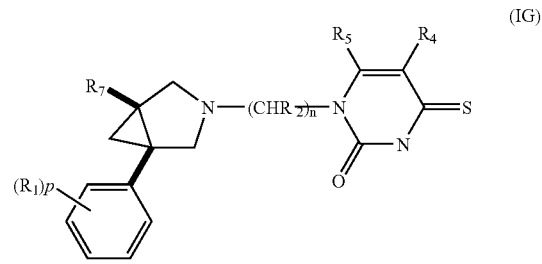
(IG)

In Formula (IG), in another embodiment, n is 3 or 4, p is 1, $R_1$ is trifluoromethyl, $R_2$ is hydrogen, $R_4$ is hydrogen, methyl, hydroxy, phenyl or fluorine, $R_5$ is hydrogen and $R_7$ is hydrogen.

The absolute configuration of the compounds of the present invention was may be assigned in agreement with the method described in the PCT International Publication WO2005/080382.

Further embodiments of the present invention are compounds of formula (IB)' which correspond to the stereochemical isomers of compounds of formula (IB) as defined above enriched in configuration (1S,5R).

In one embodiment, a stereochemical isomer of formula (IB)' or a salt thereof is provided, enriched in the configuration shown in the picture below at chiral centers at position named 1 and 5, wherein $R_1$, $R_2$, $R_4$, $R_5$, p, n, and $R_7$ are as defined for formula (I):

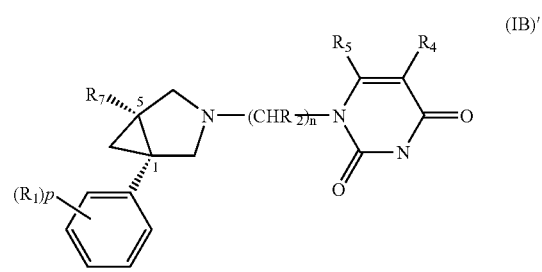
(IB)'

In Formula (IB)', in one embodiment, n is 3 or 4, p is 1, $R_1$ is trifluoromethyl, $R_2$ is hydrogen, $R_4$ is hydrogen, methyl, hydroxyl, fluorine or an optionally substituted phenyl or 5, 6-membered heteroaryl group, $R_5$ is hydrogen and $R_7$ is hydrogen.

In another embodiment, a stereochemical isomer of formula (IG)' or a salt thereof is provided, enriched in the configuration shown in the picture below at chiral centers at position named 1 and 5, wherein $R_1$, $R_2$, $R_4$, $R_5$, p, n, and $R_7$ are as defined for formula (I):

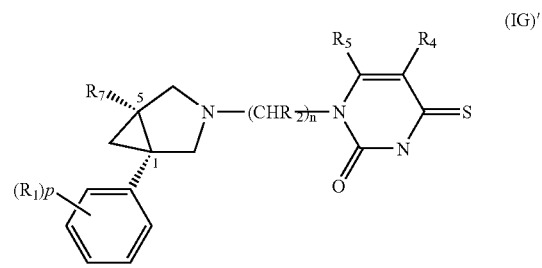
(IG)'

In Formula (IG)', in one embodiment, n is 3 or 4, p is 1, $R_1$ is trifluoromethyl, $R_2$ is hydrogen, $R_4$ is hydrogen, methyl, hydroxyl, phenyl or fluorine, $R_5$ is hydrogen and $R_7$ is hydrogen.

In a further embodiment, a stereochemical isomer enriched in the (1S,5R) configuration of formula (IM) or a salt thereof is provided, wherein $R_4$ and n are as defined for formula (I):

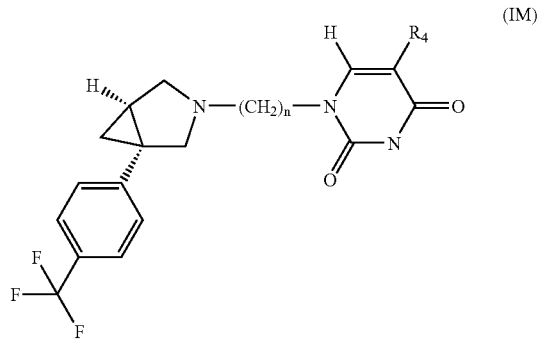

In Formula (IM), in one embodiment, n is 3 or 4, p is 1 and $R_4$ is an optionally substituted phenyl or 5,6-membered heteroaryl group (for example optionally substituted thiophenyl, pyridinyl, isoxazolyl, pyridazinyl, oxazolyl, pyrazinyl).

Certain of the compounds of the invention may form acid addition salts with one or more equivalents of the acid. The present invention includes within its scope all possible stoichiometric and non-stoichiometric forms.

Pharmaceutically acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A. C. S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) or salts thereof, may exist as polymorphs, which are included in the present invention.

Hereinafter, compounds of formula (I) and their pharmaceutically acceptable salts, solvates and prodrugs defined in any aspect of the invention (except intermediate compounds in chemical processes) are referred to as "compounds of the invention".

Those skilled in the art will appreciate that in the preparation of the compounds of the invention, it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

The present invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and non-pharmaceutically acceptable salts thereof that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and non-pharmaceutically acceptable salts thereof can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

It will be appreciated by the person skilled in the art that compounds of formula (I) may exist in the tautomeric forms (IC) and (ID) as below described:

5-methyl-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(4-{(1S,5R)-1-[4-(trifluoromethyl)phenyl]-3-azabicyclo[3.1.0]hex-3-yl}butyl)-2,4(1H,3H)-pyrimidinedione;

5-methyl-1-(4-{(1S,5R/1R,5S)-1-[3-(trifluoromethyl)phenyl]-3-azabicyclo[3.1.0]hex-3-yl}butyl)-2,4(1H,3H)-pyrimidinedione;

1-(4-{(1S,5R)-1-[4-(trifluoromethyl)phenyl]-3-azabicyclo[3.1.0]hex-3-yl}butyl)-2,4(1H,3H)-pyrimidinedione;

5-fluoro-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(5-{(1S,5R)-1-[4-(trifluoromethyl)phenyl]-3-azabicyclo[3.1.0]hex-3-yl}pentyl)-2,4(1H,3H)-pyrimidinedione;

or a salt thereof.

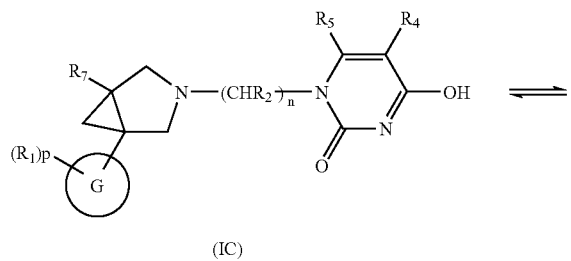

(IC)

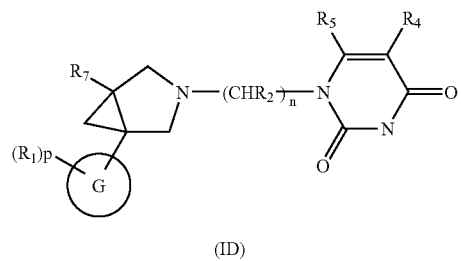

(ID)

Both tautomeric forms are intended to be included within the scope of this invention.

It will be appreciated by the person skilled in the art that compounds of formula (I) may exist in the tautomeric forms (IE) and (IF) as below described:

In another embodiment, example compounds of the present invention include:

1-(3-{(1S,5R)-1-[4-(trifluoromethyl)phenyl]-3-azabicyclo[3.1.0]hex-3-yl}propyl)-2,4(1H,3H)-pyrimidinedione;

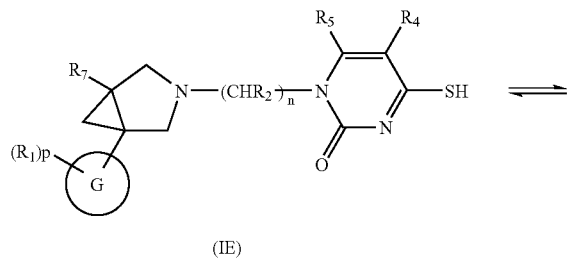

(IE)

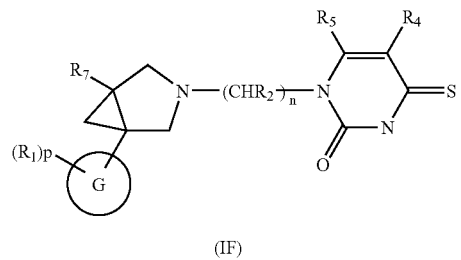

(IF)

Both tautomeric forms are intended to be included within the scope of this invention.

In one embodiment, example compounds of the present invention include:

1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(4-{(1S,5R)-1-[4-(trifluoromethyl)phenyl]-3-azabicyclo[3.1.0]hex-3-yl}butyl)-2,4(1H,3H)-pyrimidinedione;

5-methyl-1-(4-{(1S,5R/1R,5S)-1-[3-(trifluoromethyl)phenyl]-3-azabicyclo[3.1.0]hex-3-yl}butyl)-2,4(1H,3H)-pyrimidinedione;

1-(4-{(1S,5R)-1-[4-(trifluoromethyl)phenyl]-3-azabicyclo[3.1.0]hex-3-yl}butyl)-2,4(1H,3H)-pyrimidinedione;

5-fluoro-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(5-{(1S,5R)-1-[4-(trifluoromethyl)phenyl]-3-azabicyclo[3.1.0]hex-3-yl}pentyl)-2,4(1H,3H)-pyrimidinedione;

5-phenyl-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-pyrrolidinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-cyclopropyl-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[2-fluoro-4-(trifluoromethyl)phenyl]-3-azabicyclo[3.1.0]hex-3-yl}propyl)-5-(2-thienyl)-2,4(1H,3H)-pyrimidinedione;

5-(trifluoromethyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(trifluoromethyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;

2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinecarbonitrile;

2,4-dioxo-1-(4-{(1S,5R)-1-[4-(trifluoromethyl)phenyl]-3-azabicyclo[3.1.0]hex-3-yl}butyl)-1,2,3,4-tetrahydro-5-pyrimidinecarbonitrile;

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluorophenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

4-thioxo-1-(4-{(1S,5R)-1-[4-(trifluoromethyl)phenyl]-3-azabicyclo[3.1.0]hex-3-yl}butyl)-3,4-dihydro-2(1H)-pyrimidinone;

5-(2,6-difluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(methyloxy)-3-pyridinyl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione;

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

or a salt thereof.

In a further embodiment, example compounds of the present invention include:

1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(4-{(1S,5R)-1-[4-(trifluoromethyl)phenyl]-3-azabicyclo[3.1.0]hex-3-yl}butyl)-2,4(1H,3H)-pyrimidinedione;

5-methyl-1-(4-{(1S,5R/1R,5S)-1-[3-(trifluoromethyl)phenyl]-3-azabicyclo[3.1.0]hex-3-yl}butyl)-2,4(1H,3H)-pyrimidinedione;

1-(4-{(1S,5R)-1-[4-(trifluoromethyl)phenyl]-3-azabicyclo[3.1.0]hex-3-yl}butyl)-2,4(1H,3H)-pyrimidinedione;

5-fluoro-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(5-{(1S,5R)-1-[4-(trifluoromethyl)phenyl]-3-azabicyclo[3.1.0]hex-3-yl}pentyl)-2,4(1H,3H)-pyrimidinedione;

5-phenyl-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-pyrrolidinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-cyclopropyl-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[2-fluoro-4-(trifluoromethyl)phenyl]-3-azabicyclo[3.1.0]hex-3-yl}propyl)-5-(2-thienyl)-2,4(1H,3H)-pyrimidinedione;

5-(trifluoromethyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(trifluoromethyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;

2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinecarbonitrile;

2,4-dioxo-1-(4-{(1S,5R)-1-[4-(trifluoromethyl)phenyl]-3-azabicyclo[3.1.0]hex-3-yl}butyl)-1,2,3,4-tetrahydro-5-pyrimidinecarbonitrile;

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluorophenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

4-thioxo-1-(4-{(1S,5R)-1-[4-(trifluoromethyl)phenyl]-3-azabicyclo[3.1.0]hex-3-yl}butyl)-3,4-dihydro-2(1H)-pyrimidinone;

5-(2,6-difluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(methyloxy)-3-pyridinyl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione;

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(5-chloro-2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-fluoro-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-5-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

6-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(2-fluoro-3-pyridinyl)-1-(3-{(1S,5R)-1-[2-fluoro-4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R/1R,5S)-1-[3-(trifluoromethyl)phenyl]-3-azabicyclo[3.1.0]hex-3-yl}propyl)-2,4(1H,3H)-pyrimidinedione;

1-{3-[(1S,5R/1R,5S)-1-(4-chlorophenyl)-3-azabicyclo[3.1.0]hex-3-yl]propyl}-5-(2-fluoro-3-pyridinyl)-2,4(1H,3H)-pyrimidinedione;

5-(4-fluoro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(1-methylethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-chloro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(trifluoromethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione;

5-{2-[(trifluoromethyl)oxy]phenyl}-1-(3-{(1S,5R)-1-[4-(trifluoromethyl)phenyl]-3-azabicyclo[3.1.0]hex-3-yl}propyl)-2,4(1H,3H)-pyrimidinedione;

or a salt thereof.

In a further embodiment, example compounds of the present invention include:

1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(4-{(1S,5R)-1-[4-(trifluoromethyl)phenyl]-3-azabicyclo[3.1.0]hex-3-yl}butyl)-2,4(1H,3H)-pyrimidinedione;

5-methyl-1-(4-{(1S,5R/1R,5S)-1-[3-(trifluoromethyl)phenyl]-3-azabicyclo[3.1.0]hex-3-yl}butyl)-2,4(1H,3H)-pyrimidinedione;

1-(4-{(1S,5R)-1-[4-(trifluoromethyl)phenyl]-3-azabicyclo[3.1.0]hex-3-yl}butyl)-2,4(1H,3H)-pyrimidinedione;

5-fluoro-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(5-{(1S,5R)-1-[4-(trifluoromethyl)phenyl]-3-azabicyclo[3.1.0]hex-3-yl}pentyl)-2,4(1H,3H)-pyrimidinedione;

5-phenyl-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-pyrrolidinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-cyclopropyl-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[2-fluoro-4-(trifluoromethyl)phenyl]-3-azabicyclo[3.1.0]hex-3-yl}propyl)-5-(2-thienyl)-2,4(1H,3H)-pyrimidinedione;

5-(trifluoromethyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(trifluoromethyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;

2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinecarbonitrile;

2,4-dioxo-1-(4-{(1S,5R)-1-[4-(trifluoromethyl)phenyl]-3-azabicyclo[3.1.0]hex-3-yl}butyl)-1,2,3,4-tetrahydro-5-pyrimidinecarbonitrile;

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluorophenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

4-thioxo-1-(4-{(1S,5R)-1-[4-(trifluoromethyl)phenyl]-3-azabicyclo[3.1.0]hex-3-yl}butyl)-3,4-dihydro-2(1H)-pyrimidinone;

5-(2,6-difluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(methyloxy)-3-pyridinyl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione;

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(5-chloro-2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-fluoro-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-5-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

6-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(2-fluoro-3-pyridinyl)-1-(3-{(1S,5R)-1-[2-fluoro-4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R/1R,5S)-1-[3-(trifluoromethyl)phenyl]-3-azabicyclo[3.1.0]hex-3-yl}propyl)-2,4(1H,3H)-pyrimidinedione;

1-{3-[(1S,5R/1R,5S)-1-(4-chlorophenyl)-3-azabicyclo[3.1.0]hex-3-yl]propyl}-5-(2-fluoro-3-pyridinyl)-2,4(1H,3H)-pyrimidinedione;

5-(4-fluoro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(1-methylethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-chloro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(trifluoromethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione;

5-{2-[(trifluoromethyl)oxy]phenyl}-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-5-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

3-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(4-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-pyrazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

or a salt thereof.

In another embodiment, the compounds of formula (I) are selected from the group consisting of hydrochloride salts, of the compounds listed below:

1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(4-{(1S,5R)-1-[4-(trifluoromethyl)phenyl]-3-azabicyclo[3.1.0]hex-3-yl}butyl)-2,4(1H,3H)-pyrimidinedione;

5-methyl-1-(4-{(1S,5R/1R,5S)-1-[3-(trifluoromethyl)phenyl]-3-azabicyclo[3.1.0]hex-3-yl}butyl)-2,4(1H,3H)-pyrimidinedione;

1-(4-{(1S,5R)-1-[4-(trifluoromethyl)phenyl]-3-azabicyclo[3.1.0]hex-3-yl}butyl)-2,4(1H,3H)-pyrimidinedione;

5-fluoro-1-(3-{(1S,5R)-1-[4-(trifluoromethyl)phenyl]-3-azabicyclo[3.1.0]hex-3-yl}propyl)-2,4(1H,3H)-pyrimidinedione;

5-methyl-1-(5-{(1S,5R)-1-[4-(trifluoromethyl)phenyl]-3-azabicyclo[3.1.0]hex-3-yl}pentyl)-2,4(1H,3H)-pyrimidinedione;

5-phenyl-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(1-pyrrolidinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-cyclopropyl-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[2-fluoro-4-(trifluoromethyl)phenyl]-3-azabicyclo[3.1.0]hex-3-yl}propyl)-5-(2-thienyl)-2,4(1H,3H)-pyrimidinedione;

5-(trifluoromethyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(trifluoromethyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;

2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinecarbonitrile;

2,4-dioxo-1-(4-{(1S,5R)-1-[4-(trifluoromethyl)phenyl]-3-azabicyclo[3.1.0]hex-3-yl}butyl)-1,2,3,4-tetrahydro-5-pyrimidinecarbonitrile;

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluorophenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

4-thioxo-1-(4-{(1S,5R)-1-[4-(trifluoromethyl)phenyl]-3-azabicyclo[3.1.0]hex-3-yl}butyl)-3,4-dihydro-2(1H)-pyrimidinone;

5-(2,6-difluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(methyloxy)-3-pyridinyl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione;

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(5-chloro-2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-fluoro-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-5-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

6-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(2-fluoro-3-pyridinyl)-1-(3-{(1S,5R)-1-[2-fluoro-4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R/1R,5S)-1-[3-(trifluoromethyl)phenyl]-3-azabicyclo[3.1.0]hex-3-yl}propyl)-2,4(1H,3H)-pyrimidinedione;

1-{3-[(1S,5R/1R,5S)-1-(4-chlorophenyl)-3-azabicyclo[3.1.0]hex-3-yl]propyl}-5-(2-fluoro-3-pyridinyl)-2,4(1H,3H)-pyrimidinedione;

5-(4-fluoro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(1-methylethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-chloro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(trifluoromethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione;

5-{2-[(trifluoromethyl)oxy]phenyl}-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-5-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

3-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(4-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-pyrazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione.

In another embodiment, the compounds of formula (I) are selected from the group consisting of dihydrochloride salts, of the compounds listed below:

5-(1-pyrrolidinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2,6-difluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(methyloxy)-3-pyridinyl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione;

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(5-chloro-2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-fluoro-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-5-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

6-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(2-fluoro-3-pyridinyl)-1-(3-{(1S,5R)-1-[2-fluoro-4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R/1R,5S)-1-[3-(trifluoromethyl)phenyl]-3-azabicyclo[3.1.0]hex-3-yl}propyl)-2,4(1H,3H)-pyrimidinedione;

1-{3-[(1S,5R/1R,5S)-1-(4-chlorophenyl)-3-azabicyclo[3.1.0]hex-3-yl]propyl}-5-(2-fluoro-3-pyridinyl)-2,4(1H,3H)-pyrimidinedione;

5-(2-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-5-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

3-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(4-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-pyrazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione.

In another embodiment, example compounds of the present invention include:

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

or a salt thereof.

In a further embodiment, example compounds of the present invention include:

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-phenyl-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1S,5R)-1-[2-fluoro-4-(trifluoromethyl)phenyl]-3-azabicyclo[3.1.0]hex-3-yl}propyl)-5-(2-thienyl)-2,4(1H,3H)-pyrimidinedione;

1-(4-{(1S,5R)-1-[4-(trifluoromethyl)phenyl]-3-azabicyclo[3.1.0]hex-3-yl}butyl)-2,4(1H,3H)-pyrimidinedione;

5-(trifluoromethyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;

2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinecarbonitrile;

2,4-dioxo-1-(4-{(1S,5R)-1-[4-(trifluoromethyl)phenyl]-3-azabicyclo[3.1.0]hex-3-yl}butyl)-1,2,3,4-tetrahydro-5-pyrimidinecarbonitrile;

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

4-thioxo-1-(4-{(1S,5R)-1-[4-(trifluoromethyl)phenyl]-3-azabicyclo[3.1.0]hex-3-yl}butyl)-3,4-dihydro-2(1H)-pyrimidinone;

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione;

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(5-chloro-2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-fluoro-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-5-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

6-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(2-fluoro-3-pyridinyl)-1-(3-{(1S,5R)-1-[2-fluoro-4-(trifluoromethyl)phenyl]-3-azabicyclo[3.1.0]hex-3-yl}propyl)-2,4(1H,3H)-pyrimidinedione;

1-{3-[(1S,5R/1R,5S)-1-(4-chlorophenyl)-3-azabicyclo[3.1.0]hex-3-yl]propyl}-5-(2-fluoro-3-pyridinyl)-2,4(1H,3H)-pyrimidinedione;

5-(4-fluoro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-chloro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-5-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

or a salt thereof.

In a still further embodiment an example compound of the invention is 5-(2-fluoro-3-pyridinyl)-1-(3-{(1S,5R)-1-[4-(trifluoromethyl)phenyl]-3-azabicyclo[3.1.0]hex-3-yl}propyl)-2, 4(1H,3H)-pyrimidinedione or a salt thereof.

In another embodiment, an example compound of the invention is 5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride.

Some of the compounds of the present invention may be prepared following some of the procedures described in PCT International Publication WO2005/080382.

The present invention also provides a process for preparing a compound of formula (I)' or a salt thereof as defined above, which comprises the steps of:

a) reacting a compound of formula (II):

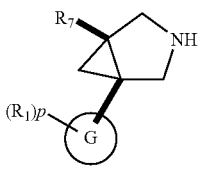

(II)

wherein $R_1$, $R_7$, G and p are as defined for formula (I), with a compound of formula (III):

X—(CHR$_2$)$_n$-A    (III)

wherein $R_2$, A and n are as defined for formula (I) and X is a leaving group,

Or b) reacting a compound of formula (II) as above defined with a compound of formula (IV)

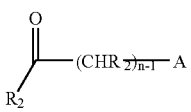

(IV)

wherein $R_2$, A and n are as defined for formula (I);

and thereafter optionally for process (a) or process (b):
(i) removing any protecting group(s); and/or
(ii) forming a salt; and/or
(iii) converting a compound of formula (I) or a salt thereof to another compound of formula (I)' or a salt thereof.

Process (a) may be performed using conventional methods for the formation of a tertiary amine. The leaving group X can be halogen such as chlorine. Alternatively X can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

Process (b) may be performed using conventional methods for the formation of a tertiary amine by means of reductive ammination. For example when, for compounds of formula (IV) $R_2$ is hydrogen, the reaction may be carried out using sodium triacetoxy borohydride in a suitable solvent such as 1,2 dichloroethane at 0° C.

In another embodiment the present invention provides a process for the preparation of compounds of formula (Ia), i.e. a compound of formula (I)' wherein p is 1 or 2 and one $R_1$ is a group $R_6$, comprises the following steps:

c) reacting a compound of formula (V):

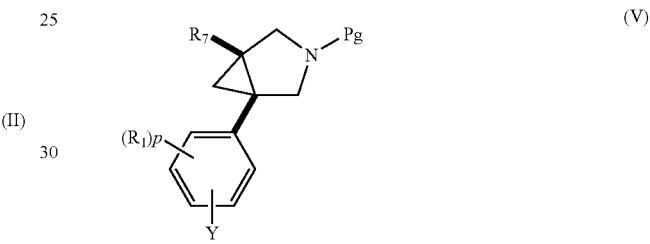

wherein $R_1$, and $R_7$ are as defined for formula (I), Pg is a suitable amine protecting group such as for example tert-buthoxy carbonyl group, p is 0 or 1 and Y is halogen, a perfluoroalkylsulfonyloxy group (e.g. trifluoromethylsulfonyloxy), or Y is a group M selected from a boron derivative (e.g. a boronic acid function B(OH)$_2$) or a metal function such as trialkylstannyl (e.g. SnBu$_3$), zinc halide or magnesium halide; with a compound of formula $R_6$—$Y_1$, wherein $R_6$ is an optionally substituted isoxazolyl, thienyl, thiazolyl or pyridyl, group, $Y_1$ is halogen when Y is a group M; or, when Y is halogen or a perfluoroalkylsulfonyloxy group, $Y_1$ is a group M as defined above or hydrogen that can be activated by a suitable base (e.g. Cs$_2$CO$_3$) in the presence of a suitable transition metal (e.g. Pd); "leaving group" is as understood by a skilled chemist, i.e. a group which can be displaced by a nucleophile in e.g. a $S_N2$, $S_N1$ or $S_NAr$ type reaction;

to form a compound of formula (XXXIV)

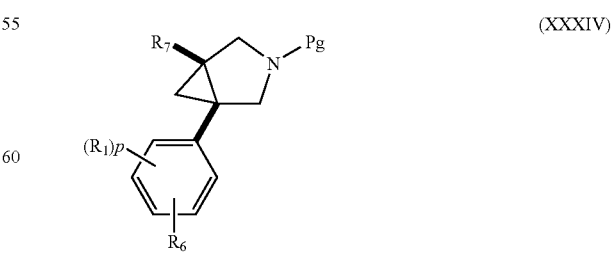

wherein $R_1$, and $R_7$ are as defined for formula (I), Pg is a suitable amine protecting group such as for example tert-buthoxy carbonyl group, p is 0 or 1 and $R_6$ is an optionally substituted isoxazolyl, thienyl, thiazolyl or pyridyl, group;

d) removing the Pg group;

e) reacting the obtained product with a compound of formula (III) or (IV), as above defined, under the conditions described for processes a) or b);

and thereafter optionally:

(i) removing any protecting group(s); and/or (ii) forming a salt; and/or (iii) converting a compound of formula (I) or a salt thereof to another compound of formula (Ia) or a salt thereof.

Reaction of a compound of formula (V) with $R_1$—$Y_1$ according to process (c) may be effected in the presence of a transition metal e.g., palladium catalyst such as bis-triphenylphosphinepalladium dichloride, tetrakis-triphenylphosphinepalladium (0) or the complex formed in situ from tris(dibenzylideneacetone) dipalladium (0) and 4,5-bis(diphenylphosphino)-9,9-dimethylxanthene. When M is a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. When M is hydrogen that can be activated by a suitable base (e.g. $Cs_2CO_3$) in the presence of a suitable transition metal (e.g. Pd) the reaction may be carried out in an inert solvent such as dioxane in the presence of a suitable base such as $Cs_2CO_3$. The substituent Y may be halogen such as bromine, or a sulfonyloxy group such as trifluoromethylsulfonyloxy; and $Y_1$ is may be a group M, such as hydrogen that can be activated by a suitable base (e.g. $Cs_2CO_3$) in the presence of a suitable transition metal (e.g. Pd).

Compounds of formula (II) may be prepared by methods well known in the art (e.g. *J. Med. Chem.* 1981, 24, 481-490 or PCT International Publication WO2005/080382). Interconversion of groups $R_1$ may be affected by methodology well known in the art (e.g. demethylation of a methoxy group resulting in a hydroxy group using a suitable Lewis acidic reagent such as boron tribromide in an inert solvent such as dichloromethane).

In one aspect of the present invention there is provided a process for the preparation of compounds of formula (IIa), i.e. a compound of general formula (II) wherein $R_7$ is hydrogen and G is a phenyl ring and $R_1$ is defined as for compounds of formula (I).

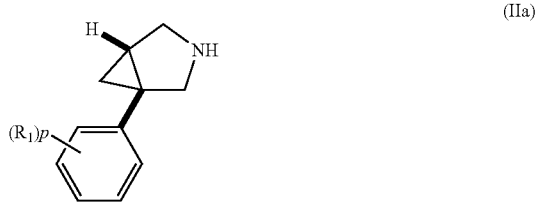

(IIa)

The process may be conveniently performed also for preparing compounds of formula (IIb), wherein the phenyl moiety of compound (IIa) is replaced by pyridine. This process comprises the following steps:

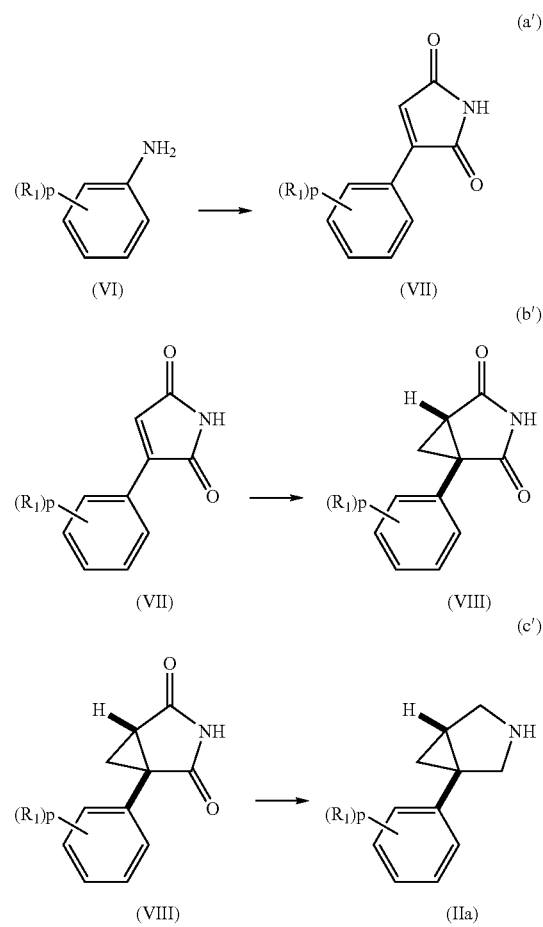

wherein:

step (a') means diazotation of an aniline (VI) followed by reaction with maleimide to give 3-arylmaleimide (VII);

step (b') means cyclopropanation of (VII) to provide bicyclic imide (VIII);

step (c') means reduction of imide (VIII) to give compounds of formula (IIa).

Step (a') may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an appropriate copper (II) salt such as anhydrous $CuCl_2$, and a suitable organonitrite, such as tert-butyl nitrite, in a compatible solvent, such as acetonitrile, is slowly added a solution of a compound of formula (VI). This is followed by allowing time to react as appropriate and a suitable workup.

Step (b') consists of slow addition of a solution of purified compound of formula (VII), or mixtures containing a compound of formula (VII), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (c') can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

In another aspect of the present invention an alternative synthetic process for the preparation of compounds of formula (II), is provided. This process comprises the following steps:

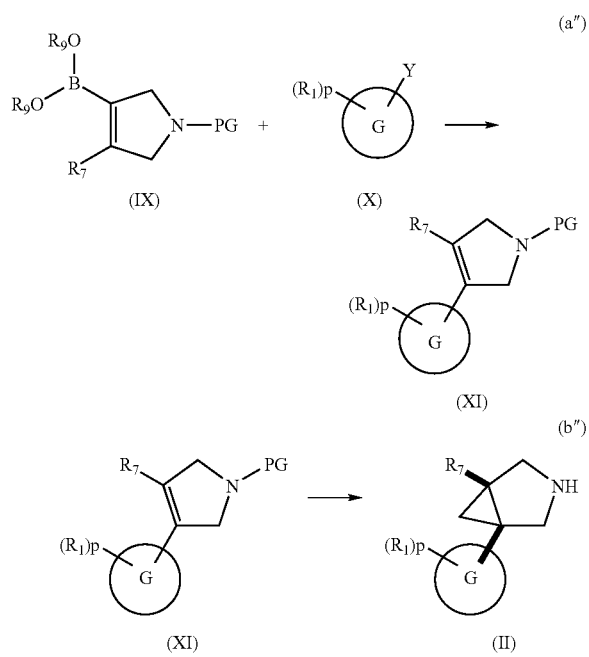

wherein:

R$_1$, p and G are as defined for formula (I), R$_9$O is a suitable alkoxy group, PG is an appropriate protecting group and Y is halogen such as bromine, or a sulfonyloxy group such as trifluoromethylsulfonyloxy; wherein:

step (a") means coupling reaction of a (2,5-dihydro-1H-pyrrol-3-yl)boronate (IX) with the aromatic halogen or sulfonyloxy derivative (X);

step (b") means cyclopropanation of (XI) followed by, if appropriate, deprotection to provide bicyclic amine (II).

Step (a") may be effected using conventional methods for the Suzuki coupling, e.g. using tetrakis(triphenylphosphine)palladium(0) as the source of catalytic palladium(0) in the presence of cesium fluoride in an appropriate solvent such as tetrahydrofuran at a suitable temperature. (R$_9$O)$_2$B may suitably be 4,4,5,5-tetramethyl-1,3,2-dioxaborolan-2-yl and PG benzyl, representing a compound of structure (X) as reported in *Synlett* 2002, 5, 829-831.

Step (b") consists of a cyclopropanation reaction effected for example using the reagent generated from trimethylsulfoxonium iodide and a suitable base such as sodium hydride. This is followed by a deprotection reaction.

In another aspect of the present invention there is provided a process for the preparation of compounds of formula (IIc), i.e. compounds of general formula (II) wherein R$_7$ is C$_{1-2}$ alkyl and G is a phenyl group. This process comprises the following steps:

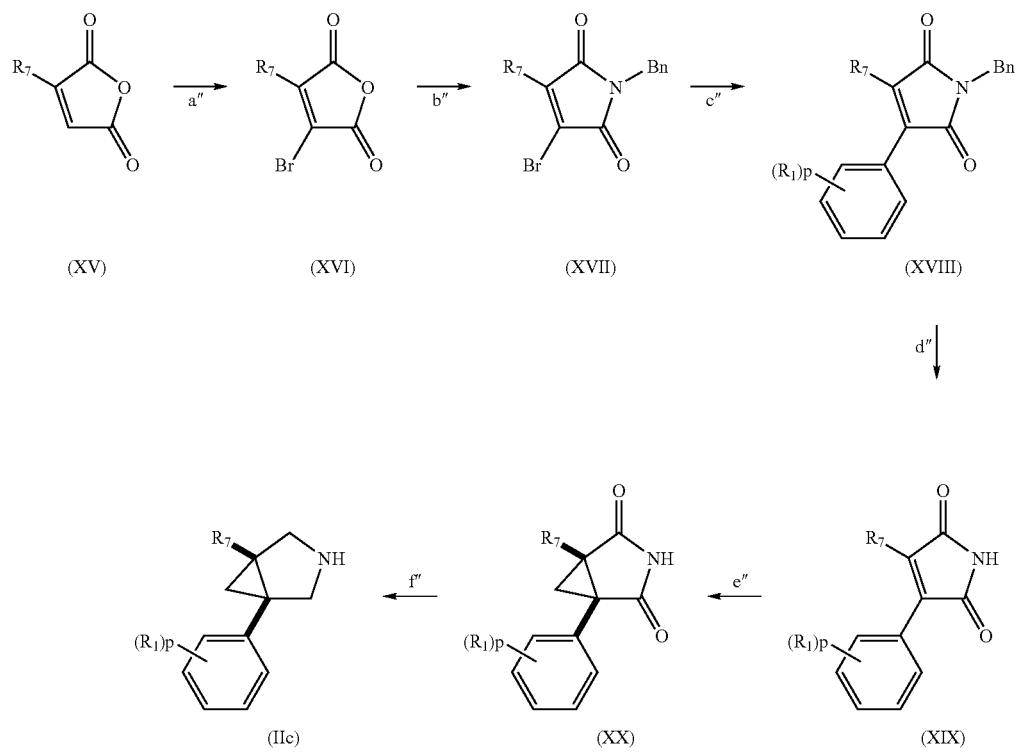

wherein:
step (a″) means bromuration of compound (XV) to give compound (XVI);
step (b″) means reaction of compound (XVI) with a benzylic amine with a benzylic amine (susceptible to afford benzylic cleavage in acidic conditions) to give imide (XVII);
step (c″) means coupling of compound (XVII) with an aryl boronic acid to give compound (XVIII);
step (d″) means removal of the benzylic protecting group of compound (XVIII) to give compound (XIX);
step (e″) means cyclopropanation of (XIX) to provide bicyclic imide (XX);
step (f″) means reduction of imide (XX) to give compounds of formula (IIc).

Step (a′) may be performed using bromine in the presence of $AlCl_3$, and heating the mixture at high temperature, suitably 120° C.

Step (b″) may be performed heating compound (XVI) together with an appropriate benzylic amine (suitably as 3,4-(dimethoxy)benzylamine or 2,4-(dimethoxy)benzylamine) in the presence of AcONa and AcOH.

Step (c″) may be performed using conventional methods for the Suzuki coupling, e.g. using $Pd(PPh_3)_2Cl_2$ as the source of catalytic palladium(0) in the presence of cesium fluoride, $BnEt_3NCl$ and a generic arylboronic acid in an appropriate mixture of solvents, (such as toluene/$H_2O$ 1:1) at a suitable temperature (such as 90° C.).

Step (d″) may be performed through an appropriate method for acidic cleavage of benzylic protecting group, such as one of those reported in "Protective groups in organic synthesis" by T. W. Greene and P. G. M. Wuts (John Wiley & sons 1991) or "Protecting Groups" by P. J. Kocienski (Georg Thieme Verlag 1994). Suitably, if the benzylic group is represented by 3,4-(dimethoxy)benzyl, protection may be removed through reaction of compound (XVIII) with TFA and anisole in the presence of sulfuric acid.

Step (e″) may be performed through slow addition of a solution of purified compound of formula (XIX), or mixtures containing a compound of formula (XIX), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (f″) may be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

A compound of formula (IIIa), i.e. compounds of formula (III) as above defined wherein A is a group $P_1$, may itself be prepared by reacting a compound of formula (XXI):

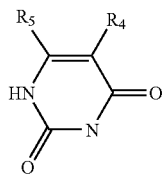

(XXI)

wherein $R_4$ and $R_5$ are as hereinbefore defined, with a compound of formula (XIII):

L(CHR_2)nX  (XIII)

wherein $R_2$ is defined as for formula (I), X is as defined above for compounds of formula (III) and L is a leaving group, e.g., a bromine atom.

The leaving group L can be halogen, such as chlorine. Alternatively L can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When L is a halogen the reaction may be carried out using a base such as potassium carbonate in the presence of a source of iodide such as sodium iodide in a solvent such as N,N-dimethylformamide at a suitable temperature, e.g. 60° C.

A compound of formula (IVa), i.e. compounds of formula (IV) as above defined wherein A is a group $P_1$, may be prepared by:
f) reacting a compound of formula (XXI):

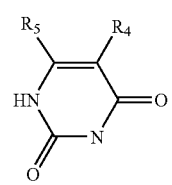

(XXI)

wherein $R_4$ and $R_5$ are defined as for compounds of formula (I), with a compound of formula (XXII)

MCR_2(CHR_2)_{n-1}X  (XXII)

wherein $R_2$ is defined as for formula (I), X is as defined above for compounds of formula (III) and M is an appropriate carbonylic protecting group (for example dimethylacetale or dioxolane);

and then
g) cleavage of the protecting group.

Cleavage of the protecting group may be carried out under appropriate conditions known to the man skilled in the art. For example, when M is dimethylacetale, the cleavage may carried out by treatment with a diluted solution of hydrochloric acid in dioxane or methanol under gentle heating (e.g. 60° C.).

A compound of formula (IVa), as above defined, may also be prepared by:
h) reacting a compound of formula (XXI), as above defined:

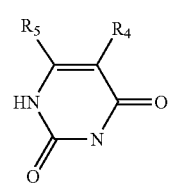

(XXI)

with a compound of formula (XXIII)

NCR_2(CHR_2)_{n-1}X  (XXIII)

wherein $R_2$ is defined as for formula (I), X is as above defined and N is a protected alcoholic function (for example: terbutyldimethylsilyl) to form a compound of formula (XXXIII)

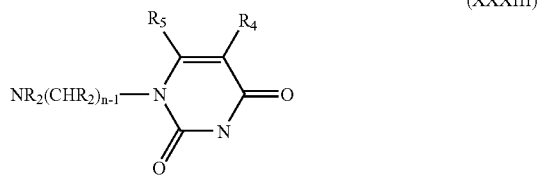

(XXXIII)

and then i) cleavage of the protecting group under appropriate conditions known to the man skilled in the art and subsequent oxidation of the free alcoholic function obtained to carbonyl group.

For example when N is a terbutyl dimethyl silyl protecting group the cleavage can be performed by treatment with a 1N solution of hydrochloric acid in dioxane at 0° C. for 1 hour. Appropriate conditions for the oxidation step comprise Dess-Martin periodinane mediated oxidation in dry THF as solvent at 0° C. for 1 hour.

Compounds of formula (XIII), (XXII) and (XXIII) are commercially available or may be prepared through reactions known in the literature.

Compounds of formula (XXI) are either commercially available or may be prepared through reactions known in the literature or through the procedures herebelow described.

Compounds (XXIa), i.e. compounds of formula (XXI) wherein $R_5$ is H and $R_4$ is a phenyl or a 5, 6 membered monocyclic heteroaryl group, may be prepared according to the following synthetic scheme:

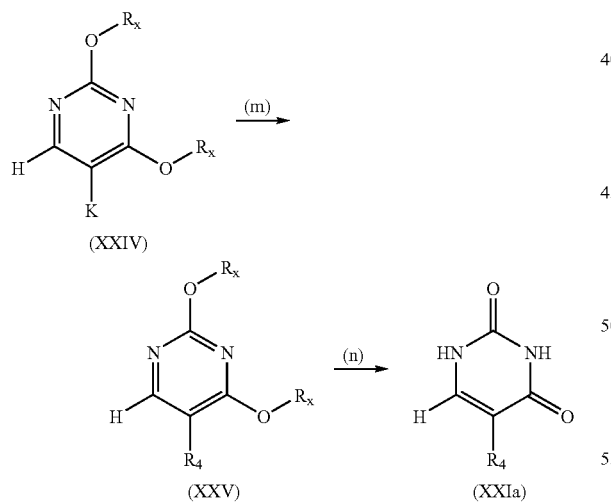

Step (m) means coupling of compounds of formula (XXIV) (commercially available, wherein $R_x$ may be a methyl, benzyl or t-butyl group) with a phenyl or heteroaryl boronic acid or ester to give compounds of formula (XXV) when K is alogen, i.e. bromine or iodine. When K is boronic acid, step (m) means coupling with a phenyl or heteroaryl alogen derivatives, i.e. bromo or iodo derivatives.

Step (n) means cleavage of the di $R_x$ protecting group to give compound (XXVI). Suitable conditions for cleavage of methyl or t-butyl protecting groups are acidic conditions; suitable conditions for removal of benzyl comprise the use of $Me_3SiI$ in dichloromethane.

Step (m) may suitably be performed using conventional method for the Suzuky coupling using for example Pd(OAc)2 as the source of catalytic palladium (0), in the presence of $Na_2CO_3$ as base and a suitable aryl boronic acid or aryl boronic ester in an appropriate solvent, such as nPrOH.

Step (n) may be performed typically by using a 4N solution of hydrochloric acid in dioxane as solvent at 0° C. for 1 hour.

An alternative process for the preparation of compounds of formula (Id), i.e. compounds of formula (I) wherein G is a phenyl ring, $R_1$ is not iodine, $R_2$ and $R_7$ are hydrogen, A is a group P1, $R_5$ is hydrogen and $R_4$ is a phenyl or a 5,6 membered monocyclic heteroaryl group, is provided, which may comprise the steps following steps:

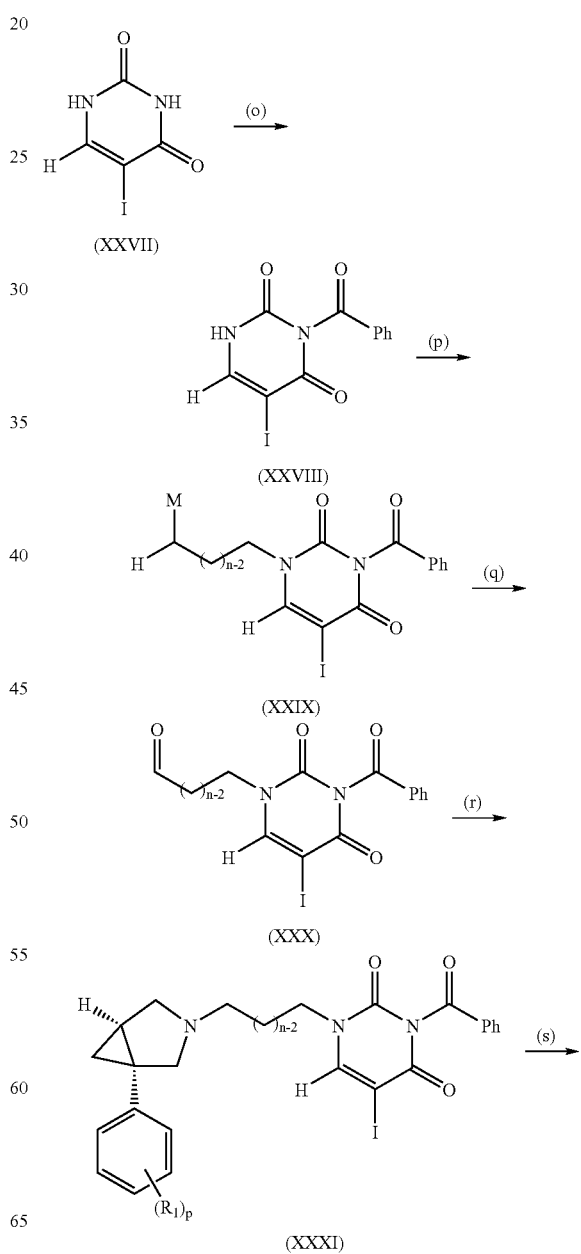

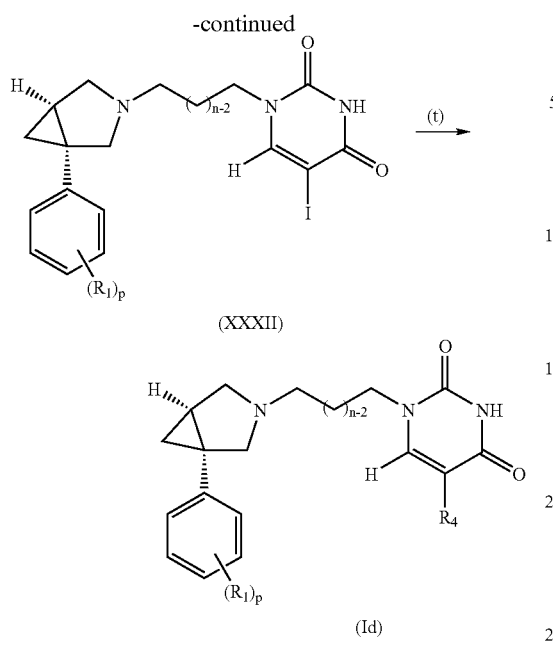

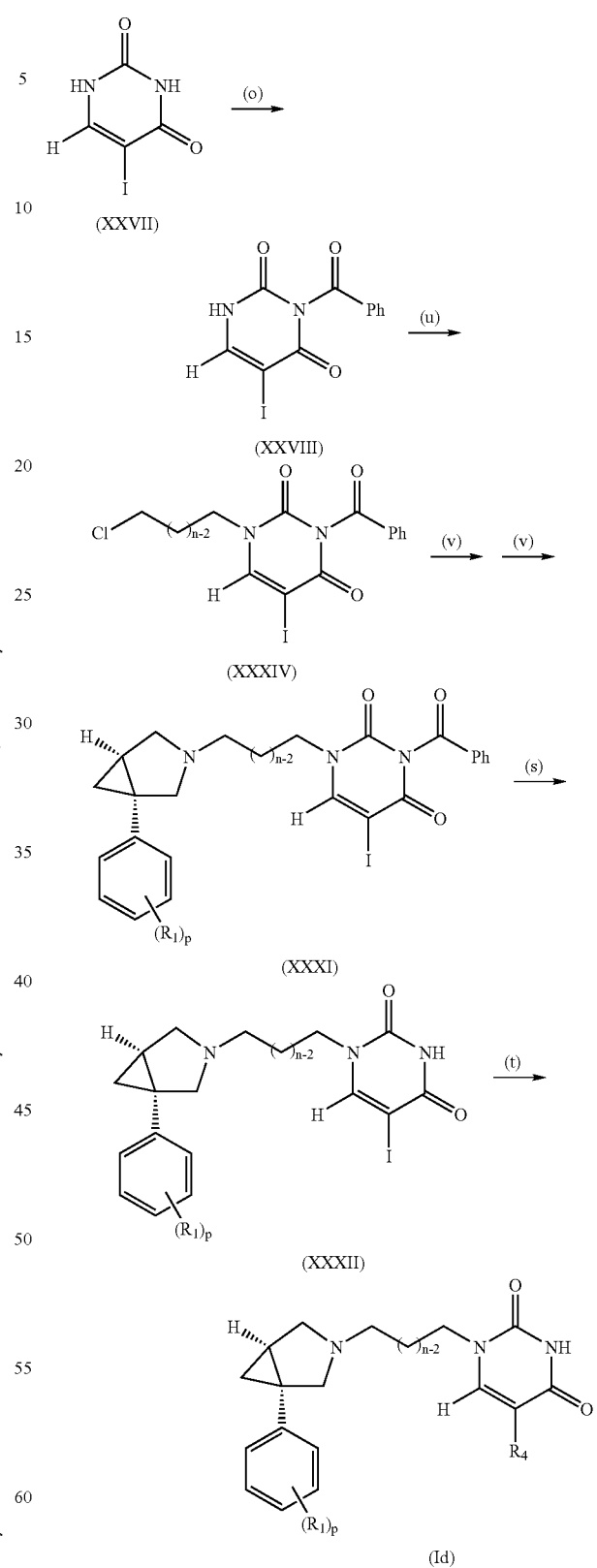

Step (o) means protection of the N-3 uracylic function of compounds of formula (XXVII) with a suitable protecting group to give compounds of formula (XXVIII). For example, when the protecting group is a benzoyl group, the reaction may be carried out using benzoyl chloride in dry pyridine as solvent at room temperature for 3 hours.

Step (p) means alkylation of N-5 uracylic function of compounds of formula (XXVIII) to give compounds of formula (XXIX), wherein M is an appropriate carbonyl protecting group (for example dimethylacetale or dioxolane). The reaction can be suitably performed for example using commercially available 3-bromo-1,1-dimethoxy propane or 3-bromo-1,1-dimethoxy butane and potassium carbonate as base in dry DMF.

Step (q) means cleavage of the carbonyl protecting group of compounds of formula (XXIX) to give compounds of formula (XXX). This step can be typically performed using a 1N solution of hydrochloric acid in dioxane as solvent at 60° C.

Step (r) means reductive amination of compounds of formula (XXX) to give compounds of formula (XXXI). This step can be typically performed using sodium triacetoxy borohydride as reductive agent in dry 1,2-dichloroethane as solvent at 0 C for 1 hour.

Step (s) means cleavage of the protecting group of compounds of formula (XXXI) to give compounds of formula (XXXII). When the protecting group is a benzoyl group, the step can be performed by means of a diluted solution of $NH_3$ (3% in MeOH) at room temperature for 3 hours.

Step (t) means coupling of compound (XXXII) with a phenyl or heteroaryl boronic acid or ester to give compounds (XXXIII). This step may be performed using conventional method for the Suzuky coupling, using for example $Pd(OAc)_2$ as the source of catalytic palladium (0), in the presence of $Na_2CO_3$ as base and a suitable phenyl or heteroaryl boronic acid or phenyl or heteroaryl boronic ester in an appropriate solvent, such as nPrOH.

Alternatively, compounds of formula (Id), as above defined, may be prepared through the following steps:

Step (o) means protection of the N-3 uracylic function of compounds of formula (XXVII) with a suitable protecting group to give compounds of formula (XXVIII). For example, when the protecting group is a benzoyl group, the reaction may be carried out using benzoyl chloride in dry pyridine as solvent at room temperature for 3 hours.

Step (u) means alkylation of N-5 uracylic function of compounds of formula (XXVIII) to give compounds of formula (XXXIV). The reaction can be suitably performed using commercially available 3-bromo-1-chloro-propane or 3-bromo-1-chloro-butane and potassium carbonate as base in dry DMF.

Step (v) means alkylation of compounds of formula (XXXIV) to give compounds of formula (XXXI). This step can be typically performed under classical alkylation conditions know to the man skilled in the art. For example the reaction may be performed in EtOH and in the presence of DIPEA, through microwave irradiation.

Step (s) means cleavage of the protecting group of compounds of formula (XXXI) to give compounds of formula (XXXII). When the protecting group is a benzoyl group, the step can be performed by means of a diluted solution of $NH_3$ (3% in MeOH) at room temperature for 3 hours.

Step (t) means coupling of compound (XXXII) with a phenyl or heteroaryl boronic acid or ester to give compounds (XXXIII). This step may be performed using conventional method for the Suzuky coupling, using for example $Pd(OAc)_2$ as the source of catalytic palladium (0), in the presence of $Na_2CO_3$ as base and a suitable phenyl or heteroaryl boronic acid or phenyl or heteroaryl boronic ester in an appropriate solvent, such as nPrOH.

Compounds of formula (Ic), i.e. compounds of formula (I)' where $R_1$, $R_2$, $R_3$, $R_4$, $R_5$, $R_6$, $R_7$, n, G and p are as above defined for formula (I) and A is a group P1, may be prepared by reacting a compound of formula (XIV):

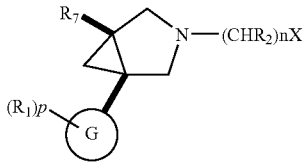

(XIV)

wherein $R_1$, $R_2$, $R_7$, G, n and p are as defined for formula (I) and X is a leaving group, with a compound of formula (XXI):

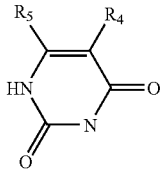

(XXI)

wherein $R_4$ and $R_5$ are as hereinbefore defined.

A compound of formula (XIV) wherein $R_1$, $R_7$, G and p are as defined for formula (I), X is a leaving group and $R_2$ is hydrogen and n is 3, can be prepared by alkylation of a compound of formula (II) in the presence of a suitable base such as a tertiary amine, for example diisopropylethylamine, with a propyl derivative carrying two leaving groups of preferrably differential reactivity in positions 1 and 3, for example 1-bromo-3-chloropropane.

Interconversion reactions between compounds of formula (I)' and salts thereof may be performed using methods well known in the art. Examples include:
(i) converting one or more of $R_1$ from alkoxy (e.g. methoxy) to hydroxy,
(ii) converting one or more of $R_1$ from hydroxy to sulfonyloxy, such as alkylsulfonyloxy or haloalkylsulfonyloxy, e.g. methanesulfonyloxy or alkylsulfonyloxy or trifluoromethanesulfonyloxy,
(iii) converting one or more of $R_1$ from halogen or perfluoroalkylsulfonyloxy to cyano;

and optionally thereafter forming a salt of formula (I)'.

When a specific enantiomer or diastereoisomer of a compound of formula (I) or salts thereof, is required, this may be obtained for example by resolution of a corresponding enantiomeric or diastereosiomeric mixture using conventional methods.

Thus, for example, specific enantiomers or diastereoisomers of the compounds may be obtained from the corresponding enantiomeric or diastereoisomeric mixture using chiral chromatographic methods such as for example chiral HPLC.

Alternatively a specific enantiomer or diastereoisomer of a compound of general formula (I), or salts thereof, may be synthesised from the appropriate optically active intermediates using any of the general processes described herein.

Compounds of formula (I) or pharmaceutically acceptable salts thereof, have been found to exhibit affinity for dopamine receptors, in particular the $D_3$ receptor, and are expected to be useful in the treatment of disease states which require modulation of such receptors, such as psychotic conditions.

Many of the compounds of formula (I) or pharmaceutically acceptable salts thereof have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of formula (I) or salts thereof are provided which have higher (e.g. $\geq 10\times$ or $\geq 100\times$ higher) affinity for dopamine $D_3$ than dopamine $D_2$ receptors (such affinity can be measured using standard methodology—see herein).

Compounds of the invention may suitably be used as selective modulators of $D_3$ receptors.

From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include substance related disorders, dyskinetic disorders such as Parkinson's disease, neuroleptic-induced parkinsonism and tardive dyskinesias; depression; anxiety, cognitive impairment including memory disorders such as Alzheimers disease, sexual dysfunction, sleep disorders, emesis, amnesia, aggression, vertigo, dementia, circadian rhythm disorders and gastric motility disorders e.g. IBS.

A wide range of psychiatric and neuropsychiatric disorders appear to be related to Obsessive-Compulsive Disorder, and form a family of related disorders referred to as obsessive-compulsive (OC) spectrum disorders. The compounds of the invention may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of the invention are also useful for the treatment of premature ejaculation. The terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

The term "psychotic disorder" includes:

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

The term "substance-related disorder" includes:

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Compounds of the invention may be useful for the treatment of cognition impairment.

The term "cognition impairment" includes cognition impairment in other diseases such as schizophrenia, bipolar disorder, depression, other psychiatric disorders and psychotic conditions associated with cognitive impairment, e.g. Alzheimer's disease.

In a further aspect therefore the present invention provides a method of treating a condition for which modulation of dopamine receptors (especially dopamine $D_3$ receptors) is beneficial, which comprises administering to a mammal (e.g. human) in need thereof an effective amount of a compound of the invention.

Modulation, as used herein, especially refers to inhibition/antagonism (which may also translate into inverse agonism in constitutively active receptor systems).

In one embodiment, the condition is a substance-related disorder, a psychotic disorder, an obsessive compulsive spectrum disorder or premature ejaculation.

The invention also provides a compound of the invention for use in therapy.

The invention also provides a compound of the invention for use in the treatment of a condition in a mammal for which modulation of dopamine receptors (especially dopamine $D_3$ receptors) is beneficial.

The invention also provides the use of a compound of the invention in the manufacture of a medicament for the treatment of a condition in a mammal for which modulation of dopamine receptors (especially dopamine $D_3$ receptors) is beneficial.

In one embodiment, compounds of the invention are used in the treatment of psychoses such as schizophrenia, in the treatment of substance abuse, in the treatment of obsessive compulsive spectrum disorders, in the treatment of premature ejaculation.

Also provided is the use of a compound of the invention in the manufacture of a medicament for the treatment of a psychotic condition, substance abuse in a mammal, obsessive compulsive spectrum disorders, and premature ejaculation.

Also provided is a compound of the invention for use in the treatment of a psychotic condition (e.g. schizophrenia), substance abuse, obsessive compulsive spectrum disorders, and premature ejaculation in a mammal.

Also provided is a compound of the invention or for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of the invention and a pharmaceutically acceptable carrier. The pharmaceutical composition can be for use in the treatment of any of the conditions described herein.

Compound of the invention may be administered by any convenient method, for example by oral, parenteral (e.g. intravenous), buccal, sublingual, nasal, rectal or transdermal administration and the pharmaceutical compositions adapted accordingly.

Compound of the invention which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the invention calculated as the free base.

The compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Functional potency of compounds of this invention can be measured by the following GTPS scintillation proximity assay (GTPS-SPA). Cells used in the study are Chinese Hamster Ovary (CHO) Cells.

Cell Line

CHO_D2

CHO_D3

Dopamine CHO $D_3$ (Biocat no 1060) transduced with bacmam G0 G-protein (Biocat no 97886)

All steps are performed at 4° C. Cell membranes are prepared as follows. Cell pellets are resuspended in 10 volumes of 50 mM HEPES, 1 mM EDTA pH 7.4, using KOH. Cells are homogenised within a glass waring blender for 2 bursts of 15 secs in 200 mls of buffer (50 mM HEPES, 1 mM leupeptin, 25 µg/ml bacitracin, 1 mM EDTA, 1 mM PMSF, 2 µM Pepstatin A). (the latter 2 reagents added as fresh ×100 and ×500 stocks respectively in ethanol). The blender is plunged into ice for 5 mins after the first burst and 10-40 mins after the final burst to allow foam to dissipate. The material is then spun at 500 g for 20 mins and the supernatant spun for 36 mins at 48.000 g. The pellet is resuspended in the same buffer as above but without PMSF and Pepstatin A. The material is then forced through a 0.6 mm needle, made up to the required volume, (usually ×4 the volume of the original cell pellet), aliquoted and stored frozen at −80° C.

The final top concentration of test drug is 3 µM in the assay and 11 points serial dilution curves 1:4 in 100% DMSO are carried out using a Biomek FX. The test drug at 1% (0.5 ul) total assay volume (TAV) is added to a solid, white Greiner polypropylene 384-well assay plate. 50% TAV (25 µl) of precoupled (for 60 mins at RT) membranes, 5 µg/well, and Wheatgerm Agglutinin Polystyrene Scintillation Proximity Assay beads (RPNQ0260, Amersham), 0.25 mg/well, in 20 mM HEPES (pH 7.4, 100 mM NaCl, 10 mM MgCl2), 60 µg/mL saponin and 30 uM GDP is added. The third addition is a 20% TAV (10 ul) addition of either buffer, (agonist format) or EC80 final assay concentration of agonist, Quinelorane, prepared in assay buffer (antagonist format). The assay is started by the addition of 29% TAV (15 ul) of GTP[35S] 0.38 nM final (37 MBq/mL, 1160 Ci/mmol, Amersham). After all additions assay plates are spun down for 1 min at 1,000 rpm. The final assay cocktail (45.5 µl) is incubated at room temperature to equilibrate for 3-6 hours before reading on a ViewLux™ (613/55 filter) luminescence imager 5 min/plate.

The effect of the test drug over the basal generates fpKi values of test drug are calculated from the $IC_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpKi is defined as −logfKi.

pKi results are only estimated to be accurate to about 0.3-0.5.

In the context of the present invention functional pKi (fpKi, corresponding to the negative logarithm of fKi) is used instead of functional Ki (fKi) and the compounds of formula (I) and salts thereof typically show fpKi for D3 receptors comprised between approximately 7.0 and 9.0.

In one embodiment compounds of formula (I) or salts thereof are provided which have higher affinity for dopamine $D_3$ than dopamine $D_2$ receptors.

In the table below a list of examples is provided that show at least 100 fold selectivity for D3 over D2 receptors.

| Example | Selectivity |
|---------|-------------|
| E8 | 100 fold |
| E9 | 199 fold |
| E16 | 100 fold |
| E28 | 316 fold |
| E27 | 251 fold |
| E30 | 199 fold |
| E43 | 100 fold |

Here below a list of examples is provided which showed no activity in the D2 GTPS-SPA assay up to the highest concentration tested in the assay (3 µM) and thus considered to be selective for D3 over D2 receptors:

E5, E12, E13, E17, E18, E19, E20, E23, E24, E25, E26, E29, E31, E32, E33, E35, E36, E38, E39, E40, E41, E42, E44, E45, E47, E48, E50, E51, E53, E59, E61, E63, E64.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

All temperatures refer to ° C.

Proton Magnetic Resonance (NMR) spectra may be typically recorded either on Varian instruments at 300, 400 or 500 MHz, or on a Bruker instrument at 300 and 400 MHz. Chemical shifts are expressed in parts of million (ppm, α units). Coupling constants are in units of hertz (Hz) chemical shifts are reported in ppm downfield (d) from $Me_4Si$, used as internal standard, and are typically assigned as singlets (s), broad singlets (bs), doublets (d), doublets of doublets (dd), triplets (t), quartets (q) or multiplets (m).

Mass spectra (MS) may be typically taken on a 4 II triple quadrupole Mass Spectrometer (Micromass UK) or on a Agilent MSD 1100 Mass Spectrometer, operating in ES (+) and ES (−) ionization mode or on an Agilent LC/MSD 1100 Mass Spectrometer, operating in ES (+) and ES (−) ionization mode coupled with HPLC instrument Agilent 1100 Series. In the mass spectra only one peak in the molecular ion cluster is typically reported.

LCMS may be recorded under the following conditions:

DAD chromatographic traces, mass chromatograms and mass spectrums may be taken on a UPLC/MS Acquity™ system coupled with a Micromass ZQTM mass spectrometer operating in ESI positive. The phases used are: A) H2O/ACN 95/5+0.1% TFA; B) H2O/ACN 5/95+0.1% TFA. The gradient is: t=0 min) 95% A 5% B, t=0.25) 95% A 5% B, t=3,30) 100% B, t=4,0) 100% B, followed by 1 min of reconditioning Column: Acquity BEH C18 2.1×50 mm 1.7 um 35° C. Flow: 600 uL/min.

Mass tune: Capillary 3.25 kV, cone 20V, source temperature 115° C. desolvation T 350° C.

Preparative LC-MS purifications may be performed under the following conditions:

Instrument: HPLC-MS preparative system Waters (2767 and 2525) coupled with photodiode array detector and Micromass ZQ. Column: Waters XTerra MS C18 (19×300 mm, 10 um). Flow rate 20 ml/min. Mobile phase: A phase=water+ 0.1% TFA, B phase=acetonitrile+0.1% TFA. 0-3.0 min (A: 90%, B: 10%), 3.0 min (A: 90%, B: 10%), 3.0-26.0 min (A: 5%, B: 95%), 26.0 min (A: 5%, B: 95%), 26.0-30.0 min (A: 5%, B: 95%), 30.0 min (A: 5%, B: 95%), 30.0-30.5 min (A: 90%, B: 10%), 30.5 min (A: 90%, B: 10%), 30.5-31.5 min (A: 90%, B: 10%). The fractions containing the pure material are typically collected and the solvents evaporated. The so obtained trifluoroacetate salts are typically neutralized by passing over SCX cartridge.

Preparative HPLC purifications may be performed under the following conditions:

Instrument: Shimadzu (LC/8A and SCL/10A) coupled with UV spectrophotometric dector (SPD/6A). Column: Waters SymmetryPrep C18 19×30 mm×7 um; flow rate: 20 ml/min; mobile phase: A phase=water/acetonitrile 9/1+0.5% TFA, B phase=water/acetonitrile 5/95+0.5% TFA using a 30 min gradient of 5-100% solvent B.

The fractions containing the pure material are typically collected and the solvents evaporated. The so obtained trifluoroacetate salts are typically neutralized by passing over SCX cartridge.

Optical rotations may be typically measured using a (Perkin Elmer Model 341) polarimeter operating at 589 nm (Sodium source) [Measurements are made using a 1 decimeter microcell thermostated at 23° C. Concentrations are typically 10 mg/ml (c=1)] or using a (Perkin Elmer Model 241) polarimeter operating at 589 nm (Sodium source) [Measurements are made using a 1 decimeter microcell thermostated at 23° C. Concentrations are typically 10 mg/mL (c=0.01)]. For ab initio OR assignments, the Dalton Quantum Chemistry Program are used.

Melting point determination may be performed on a Buchi B-540 apparatus.

Compounds may be named using ACD/Name PRO6.02 chemical naming software (Advanced Chemistry Development Inc., Toronto, Ontario, M5H2L3, Canada) or ISIS/Draw 2.5 SR 2 Autonom (MDL Information System, Inc)

For reactions involving microwave irradiation, a Personal Chemistry Emrys™ Optimizer may be used.

Flash silica gel chromatography may be carried out on silica gel 230-400 mesh (supplied by Merck AG Darmstadt, Germany) or over pre-packed Biotage silica cartridges.

Purification may also be performed using either Biotage manual flash chromatography (Flash+). All these instruments work with Biotage Silica cartridges.

Unless otherwise stated, all reaction are typically performed under inert atmosphere (for example under Nitrogen).

The following abbreviations are used in the text: EtOAc=ethyl acetate, Et$_2$O=dietyl ether, MeOH=methanol; NaBH(AcO)$_3$=sodium triacetoxyboron hydride, THF=tetrahydrofuran, Tlc refers to thin layer chromatography on silica plates, and dried refers to a solution dried over anhydrous sodium sulphate, r.t. (RT) refers to room temperature, DMSO=dimethyl sulfoxide; DMF=N,N'-dimethylformamide, DCM=dichloromethane, TEA=triethylamine, DIPEA=diisopropylethylamine, DEAD=diethylazodicarboxylate, TFA=trifluoroacetic acid, n-PrOH=normal propanol, i-PrOH=isopropanol, i-Pr$_2$O or DIPE=diisopropylether, DME=dimethoxyethane, EtOH=ethanol, AcOH=Acetic acid, DCE=dichloroethane, IPA=isopropyl alcohol, Pd(OAc)$_2$=Palladium diacetate, SPE Cartridge=Solid Phase Extraction Cartridge; SCX Cartridge=Strong Cation Exchange Cartridge.

Preparation 1

3-[4-(trifluoromethyl)phenyl]-1H-pyrrole-2,5-dione (Prep1)

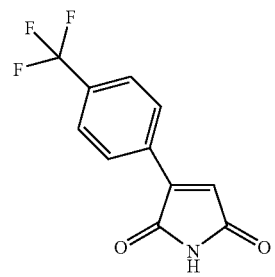

A mixture of hydrochloric acid (37% in water, 285 mL) and water (190 mL) was added to 4-(trifluoromethyl)aniline (150 g, 116 mL) at room temperature with vigorous stirring and the formed precipitate was allowed to stir for further 30 minutes. Temperature was reduced to 0° C. and sodium nitrite (70.6 g) in 180 mL of water was added dropwise to the stirred suspension. At the end of diazotisation, a clear yellow solution was obtained. Maleimide (180 g) in acetone (1.1 L) was added dropwise at 0° C. and then the pH of the solution was adjusted to 3-3.5 by adding sodium acetate. Copper (II) chloride (18.8 g) was added to the vigorously stirred mixture. After a few minutes a gas started to develop (conspicuous foaming). The reaction mixture was allowed to stir at 0° C. for 1 h and overnight at room temperature. Acetone was removed in vacuo, the residue was filtered and dried overnight in vacuo to give the title compound (155 g) as a light brown solid.

MS (ES) (m/z): 242.2 [MH]$^+$.

Preparation 2

(1R,5S/1S,5R)-1-[4-(trifluoromethyl)phenyl]-3-azabicyclo[3.1.0]-hexane-2,4-dione (Prep2)

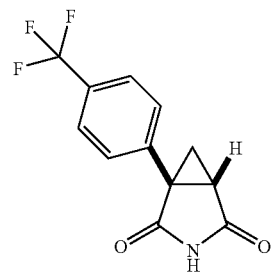

Milled sodium hydroxide (40 g) was added in small portions to a stirred solution of trimethylsulfoxonium iodide (219 g) in DMSO (anhydrous, 2 L). The resulting mixture was allowed to stir at room temperature for 1.5 h. 3-[4-(Trifluoromethyl)phenyl]-1H-pyrrole-2,5-dione (Prep, 120 g) dissolved in DMSO (anhydrous, 0.5 L) was then added dropwise and the resulting mixture was allowed to stir at room temperature for 20 minutes. Temperature was then reduced to 0° C. and aqueous saturated NH$_4$Cl (2 L) was slowly added, followed by Et₂O (1 L). After separation of the two phases, the aqueous layer was repeatedly extracted with Et₂O (3×1 L). Combined organic layers were washed with brine (2×1 L) and then dried over Na₂SO₄. Evaporation of the solvent gave a light brown solid which was suspended in 1 L of dichloromethane and 1 L of cyclohexane. The mixture was allowed to stir at room temperature for 45 minutes and then filtered to give the title compound (116 g) as white solid.

MS (ES) (m/z): 256.1 [MH]⁺.

Preparation 3

(1R,5S/1S,5R)-1-[4-(trifluoromethyl)phenyl]-3-azabicyclo[3.1.0]hexane (Prep3)

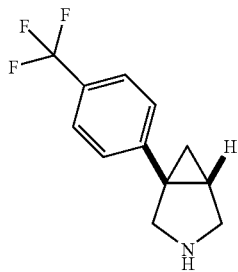

Borane (1M in tetrahydrofuran, 1.4 l) was charged into a 5 l reactor under N₂ and cooled at 0° C. (1R,5S/1S,5R)-1-[4-(trifluoromethyl)phenyl]-3-azabicyclo[3.1.0]hexane-2,4-dione (Prep2, 101 g) dissolved in anhydrous THF (1 L) was then added dropwise with vigorous stirring whereby the temperature was constantly kept below 5° C. and gas evolution was monitored. At the end of the addition the resulting mixture was allowed to stir at 0° C. for 1 h and then at room temperature overnight. The mixture was then cooled to 0° C. and methanol (200 mL) followed aqueous 6 M hydrochloric acid solution (0.8 L) were cautiously added monitoring gas evolution. THF was then removed in vacuo, the residue was cooled to 0° C. and an aqueous 5M sodium hydroxide solution was added until pH 9-10 had been reached. The aqueous layer was extracted with Et₂O (3×1 L). Removal of solvent in vacuo gave the title compound (140 g) as colorless oil.

MS (ES) (m/z): 228.1 [MH]⁺.

Preparation 4

(1S,5R)-1-[4-(trifluoromethyl)phenyl]-3-azabicyclo[3.1.0]hexane (Prep4)

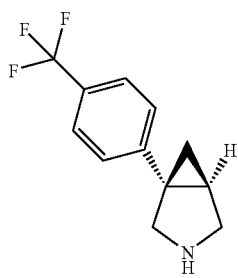

(S)-(+)-Mandelic acid (94 g) was added in portions to a stirred solution of (1R,5S/1S,5R)-1-[4-(trifluoromethyl)phenyl]-3-azabicyclo[3.1.0]hexane (Prep3, 140 g) in 1.4 L of THF. The resulting mixture was stirred at room temperature for 2 h until a white precipitate was formed. The mixture was then warmed up to reflux temperature, stirred for 45 minutes and then slowly cooled down to room temperature. The white solid was collected by filtration and dried in vacuo. This material was recrystallised 4 times from THF (10 volumes) to give 32.5 g of a white solid. This material was then suspended in sodium hydroxide (1M solution, 400 mL) and Et₂O (400 mL) and allowed to stir at room temperature until complete dissolution. After separation of the two phases, the aqueous layer was extracted again with Et₂O (3×250 mL). Combined organic layers were washed with aqueous 1M sodium hydroxide solution (3×200 mL) and then dried over Na₂SO₄. Evaporation of solvent in vacuo gave the title compound (19 g) as white solid. The absolute configuration of the optical isomers was assigned as described in PCT International Publication WO2005/080382.

¹H-NMR (CDCl₃): δ 7.51 (d, 2H), 7.25 (d, 2H), 3.20 (d, 1H), 3.0-3.1 (m, 3H), 1.69 (m, 1H), 0.8-1.0 (m, 2H), NH not observed. MS (ES) (m/z): 228.1 [MH]⁺.

| Analytical chromatography | |
|---|---|
| Column: | chiralcel OD 10 um, 250 × 4.6 mm |
| Mobile phase: | A: n-Hexane; B: Isopropanol + 0.1% Isopropyl amine |
| Gradient: | isocratic 2% B |
| Flow rate: | 1 mL/min |
| UV wavelengh range: | 200-400 nm |
| Analysis time: | 25 min |
| ret. time (min) | % a/a |
| 16.5 | 0.4 (1R,5S)-1-[4-(trifluoromethyl)phenyl]-3-azabicyclo[3.1.0]hexane |
| 21.7 | 99.6 title compound |
| Specific Optical Rotation: | [α]_D = −10° (CDCl₃, T = 20° C., c ≅ 0.004 g/0.8 ml). |

Preparation 5

3-{(1S,5R)-1-[4-(trifluoromethyl)phenyl]-3-azabicyclo[3.1.0]hex-3-yl}-1-propanol (Prep5)

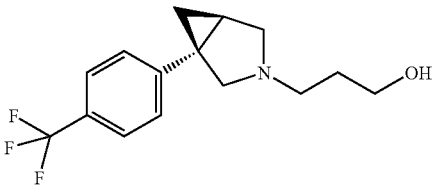

To a solution of (1S,5R)-1-[4-(trifluoromethyl)phenyl]-3-azabicyclo[3.1.0]hexane (Prep4, 151 mg) in dry THF (3.3 mL), TEA (0.112 mL) and 3-bromo-1-propanol (0.073 mL) were added and the resulting mixture was heated at reflux for 4 hours. After cooling at room temperature it was diluted with EtAcO (20 mL), washed with water, dried over anhydrous Na₂SO₄ and concentrated under reduced pressure. The crude product was purified by a silica SPE cartridge (10 g) eluting with DCM/MeOH from 99/1 to 96/4 to give the title compound as a colourless oil (143 mg).

¹H-NMR (CDCl₃): δ 7.50 (d, 2H), 7.19 (d, 2H), 4.85 (bs, 1H), 3.85 (t, 2H), 3.58 (d, 1H), 3.33 (d, 1H), 2.80 (m, 2H), 2.62 (dd, 1H), 2.50 (dd, 1H), 1.82 (m, 2H), 1.72 (m, 1H), 1.38 (t, 1H), 0.91 (dd, 1H). MS (ES) (m/z): 286 [MH]⁺.

Preparation 6

1-(4-chlorobutyl)-5-methyl-2,4(1H,3H)-pyrimidinedione (Prep6)

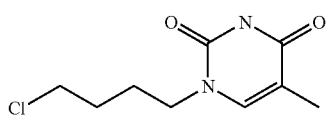

A mixture of 5-methyl-2,4(1H,3H)-pyrimidinedione (thimine, 500 mg, commercially available from Aldrich) and $K_2CO_3$ (546 mg) in dry DMSO (15 mL) was stirred for 1 hour at room temperature. 1-bromo-4-chlorobutane (0.46 mL) was then added and the mixture was stirred at room temperature for 20 hours. Water was then added and the resulting mixture was extracted with EtAcO. The aqueous phase was acidified to pH 7 with aqueous 2% HCl solution and extracted with DCM. The organic phases were washed with brine, dried over $Na_2SO_4$ and concentrated in vacuo. The crude product was purified by a silica SPE cartridge (25 g) eluting with toluene/acetone from 95/5 to 75/25 to give the title compound as a colourless oil (250 mg).

$^1$H-NMR (CDCl$_3$): δ 8.32 (bs, 1H), 7.02 (s, 1H), 3.74 (t, 2H), 3.55 (t, 2H), 1.95 (s, 3H), 1.97-1.75 (m, 4H). MS (ES) (m/z): 217 [MH]$^+$.

Preparation 7

3-(phenylcarbonyl)-1-(3-{(1S,5R)-1-[4-(trifluoromethyl)phenyl]-3-azabicyclo[3.1.0]hex-3-yl}propyl)-2,4(1H,3H)-pyrimidinedione (Prep7)

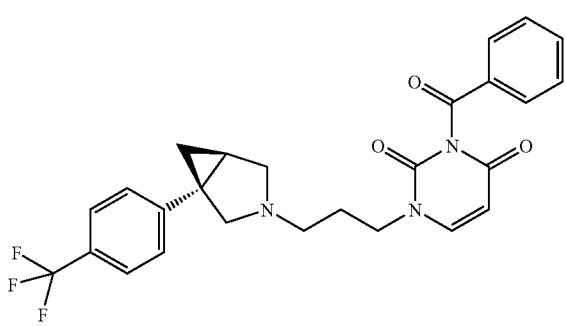

To a solution of 3-{(1S,5R)-1-[4-(trifluoromethyl)phenyl]-3-azabicyclo[3.1.0]hex-3-yl}-1-propanol (Prep5, 51 mg), 3-(phenylcarbonyl)-2,4(1H,3H)-pyrimidinedione (39 mg, prepared according to the procedure reported in J. Chem. Soc., Perkin Trans. 1, 2827 (1998)) and PPh$_3$ (140 mg) in dry dioxane at 110° C., DEAD (40% solution in toluene, 0.243 mL) was added dropwise. After 3 hours the mixture was concentrated under reduced pressure. The crude product was purified by a silica SPE cartridge (10 g) eluting with DCM/MeOH from 100/0 to 95/5 followed by a SCX cartridge (eluting with MeOH and then NH$_3$ 0.3M in methanol) to give the title compound as a colourless oil (35 mg).

MS (ES) (m/z): 484 [MH]$^+$.

Preparation 8

1-(4-chlorobutyl)-2,4(1H,3H)-pyrimidinedione (Prep8)

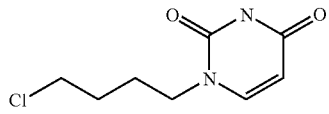

A mixture of 1-(4-chlorobutyl)-2,4(1H,3H)-pyrimidinedione (uracil, 500 mg, commercially available from Aldrich) and $K_2CO_3$ (1.23 g) in dry DMF (20 mL) was stirred for 30 min at room temperature. 1-bromo-4-chlorobutane (0.4 mL) was then added and the mixture was stirred at room temperature for 20 hours. Water was then added and the resulting mixture was extracted with EtOAc. The aqueous phase was acidified to pH 7 with an aqueous 2% HCl solution and extracted with DCM. The organic phases were washed with brine, dried over $Na_2SO_4$ and concentrated in vacuo. The crude product was purified by a silica SPE cartridge (10 g) eluting with DCM/MeOH from 100/0 to 99/1 to give the title compound as a colourless oil (141 mg).

NMR ($^1$H, CDCl$_3$): δ 9.6 (bs, 1H), 7.18 (d, 1H), 5.72 (d, 1H), 3.79 (t, 2H), 3.58 (t, 2H), 1.95-1.75 (m, 4H). MS (ES) (m/z): 203 [MH]$^+$.

Preparation 9

1-(4-chlorobutyl)-4-phenyl-2(1H)-pyrimidinone (Prep9)

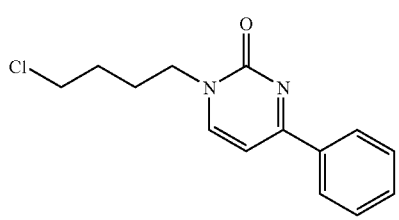

The title compound was prepared according to a similar procedure to that described in PCT Publication WO2004/080981.

MS (ES) (m/z): 207 [MH]+.

Preparation 10

1-(3-chloropropyl)-5-fluoro-2,4(1H,3H)-pyrimidinedione (Prep10)

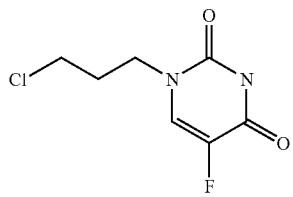

A mixture of 5-fluoro-2,4-bis[(trimethylsilyl)oxy]pyrimidine (1 g, commercially available from Lancaster), 1-bromo- 3-chloropropane (0.44 mL) and I₂ (10 mg) in 1,2-dichloroethane (10 mL) was heated to reflux for 30 h. Then the reaction mixture was treated with water and the pH was brought to 7 using aqueous 6N NaOH solution, the mixture was extracted twice with DCM, the organic phase dried over Na₂SO₄ and the solvent evaporated under reduced pressure. The crude product was purified by flash chromatography on silica gel eluting with DCM/MeOH 95/5 to give 35 mg of the title compound.

MS (ES) (m/z): 264 [MH]+.

Preparation 11

1-(4-chloropentyl)-5-methyl-2,4(1H,3H)-pyrimidinedione (Prep11)

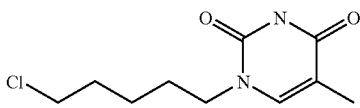

A mixture of 5-methyl-2,4(1H,3H)-pyrimidinedione (thimine, 500 mg) and K₂CO₃ (548 g) in dry DMF (15 mL) was stirred for 1 hour at room temperature. 1-bromo-4-chloropentane (0.548 mL) was then added and the mixture was stirred at room temperature for 4 hours. Water was then added and the resulting mixture was extracted with dichloromethane. The aqueous phase was acidified to pH 7 with aqueous 2% HCl solution and extracted with DCM. The organic phases were dried and concentrated in vacuo. The crude product was purified by a silica SPE cartridge eluting with DCM/MeOH from 98/2 to 95/5 to give the title compound (100 mg).

¹H-NMR (CDCl₃): δ 8.03 (bs, 1H), 6.99 (s, 1H), 3.72 (t, 2H), 3.56 (t, 2H), 1.94 (s, 3H), 1.93-1.40 (m, 6H). MS (ES) (m/z): 231 [MH]⁺.

Preparation 12

1-(4-chlorobutyl)-4-methyl-2(1H)-pyrimidinone (Prep12)

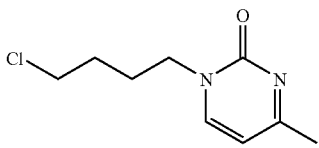

The title compound was prepared according to a similar procedure to that described in the patent WO2004/080981.

MS (ES) (m/z): 201 [MH]+.

Preparation 13

(1S,5R)-3-(3-Chloropropyl)-1-[4-(trifluoromethyl)phenyl]-3-azabicyclo[3.1.0]hexane (Prep13)

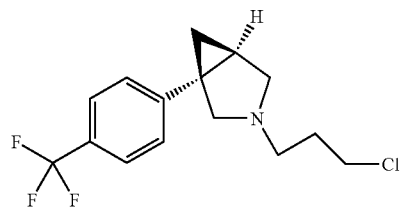

To a solution of (1S,5R)-1-[4-(trifluoromethyl)phenyl]-3-azabicyclo[3.1.0]hexane (P4, 1.00 g) in dry THF (5 mL), DIPEA (2.4 mL) and 1-bromo-3-chloropropane (3.7 mL) were added and the resulting mixture was heated at reflux for 3 hours. After cooling at room temperature it was diluted with EtOAc (30 mL) washed twice with a saturated solution of NH₄Cl in water (20 mL) and once with a saturated aqueous NaHCO₃ solution (20 mL), dried over anhydrous Na₂SO₄ and concentrated under reduced pressure. The crude product was purified by silica gel chromatography eluting with cyclohexane/EtOAc 7:3 to give the title compound as a colourless oil (1.26 g).

NMR (¹H, CDCl₃): δ 7.50 (d, 2H) 7.19 (d, 2H), 3.59 (t, 2H), 3.33 (d, 1H), 3.09 (d, 1H), 2.58 (m, 2H), 2.66 (dd, 1H), 2.46 (dd, 1H), 1.92 (m, 2H), 1.74 (m, 1H), 1.67 (t, 1H), 0.81 (dd, 1H). MS (ES) (m/z): 304 [MH]⁺.

Preparation 14

1-(3-chloropropyl)-5-phenyl-2,4(1H,3H)-pyrimidinedione (Prep14)

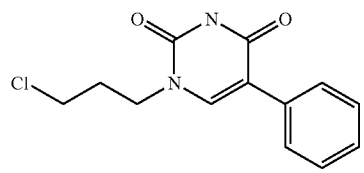

A mixture of 5-phenyl-2,4(1H,3H)-pyrimidinedione (527 mg, commercially available from Akos) and K₂CO₃ (386 mg) in dry DMF (10 mL) was stirred for 1 hour at room temperature. 1-Bromo-3-chloropropane (0.28 mL) was added and the mixture was stirred at room temperature for 20 hours. One more portion of 1-bromo-3-chloropropane (0.14 mL) was added and the mixture was stirred at room temperature for 20 hours. Water was added and the resulting mixture was extracted with ethyl acetate. The organic phases were washed with brine, dried over Na₂SO₄ and concentrated in vacuo. The crude product was purified by a silica flash chromatography (eluting with A: dichloromethane, B: dichloromethane/methanol=9/1 at ratio A:B=6:4) to give the title compound as a colourless oil (150 mg).

MS (m/z): 265 [MH]⁺.

Preparation 15

1-(3-chloropropyl)-5-(2-thienyl)-2,4(1H,3H)-pyrimidinedione (Prep15)

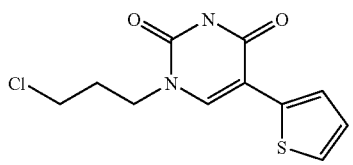

The title compound was prepared with a similar procedure to that set out earlier in Preparation 14 in 120 mg yield as colourless oil from 5-(2-thienyl)-2,4(1H,3H)-pyrimidinedione (400 mg, commercially available from Building Blocks for Combinatorial Chemistry and Other Synthesis)

MS (ES) (m/z): 271 [MH]$^+$.

Preparation 16

1-(3-chloropropyl)-5-cyclopropyl-2,4(1H,3H)-pyrimidinedione (Prep16)

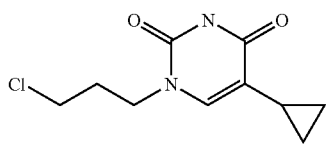

The title compound was prepared with a similar procedure to that set out earlier in Preparation 14 in 120 mg yield as colourless oil from 5-cyclopropyl-2,4(1H,3H)-pyrimidinedione (426 mg, commercially available from AKos Building Blocks)

MS (ES) (m/z): 4229 [MH]$^+$.

Preparation 17

1-(3-chloropropyl)-5-(1-pyrrolidinyl)-2,4(1H,3H)-pyrimidinedione (Prep17)

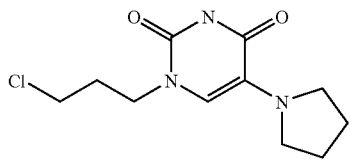

A mixture of 5-(1-pyrrolidinyl)-2,4(1H,3H)-pyrimidinedione (507 mg, commercially available from Interchim Intermediates) and K$_2$CO$_3$ (386 mg) in dry DMF (10 mL) was stirred for 1 hour at room temperature. 1-Bromo-3-chloropropane (0.28 mL) was added and the mixture was stirred at room temperature for 20 hours. Water was added and the resulting mixture was extracted with ethyl acetate. The organic phases were washed with brine, dried over Na$_2$SO$_4$ and concentrated in vacuo. The crude product was purified by a silica flash chromatography (eluting with A: dichloromethane, B: dichloromethane/methanol=9/1 at ratio A:B=6:4) to give the title compound as a colourless oil (150 mg).

MS (ES) (m/z): 258 [MH]$^+$.

Preparation 19

1-[3-(tert-Butyl-dimethyl-silanyloxy)-propyl]-5-trifluoromethyl-1H-pyrimidine-2,4-dione (Prep19)

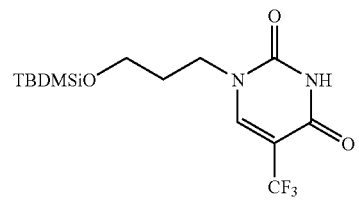

To a suspension of 50% NaH (0.42 g, 8.7 mmol) in DMF (5 mL), a solution of 5-trifluoromethyl-1H-pyrimidine-2,4-dione (1.2 g, 6.66 mmol) was added drop wise maintaining the temperature at 0° C. The mixture was then heated at 100° C. for 1 hour. After cooling to room temperature, (3-bromopropoxy)-tert-butyl-dimethyl-silane (2 mL, 8.7 mmol) was added and the reaction was stirred overnight. The solvent was evaporated and the crude was dissolved in a 25%$_{aq}$ solution of citric acid and extracted with Et$_2$O. The organic phase was dried (Na$_2$SO$_4$) and evaporated. The crude was purified by flash chromatography with ethyl acetate-petroleum ether (2-8) to give 0.87 g of 1-[3-(tert-butyl-dimethyl-silanyloxy)-propyl]-5-trifluoromethyl-1H-pyrimidine-2,4-dione (37% yield).

MS (ES) (m/z) 353.4 [M+H]$^+$.

$^1$H-NMR (CDCl$_3$) δ: 8.75 (br. s., 1 H), 7.75-7.78 (m, 1 H), 3.96 (dd, 2 H), 3.67 (t, 2 H), 1.93 (ddd, 2 H), 0.91 (s, 9 H), 0.08 (s, 6 H).

Preparation 20

1-(3-Hydroxy-propyl)-5-trifluoromethyl-1H-pyrimidine-2,4-dione (Prep20)

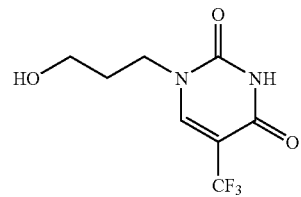

A solution of 1-[3-(tert-butyl-dimethyl-silanyloxy)-propyl]-5-trifluoromethyl-1H-pyrimidine-2, 4-dione (Prep 19, 0.86 g, 2.4 mmol) in DCM (10 mL) was cooled at 0° C. and then TFA (2.8 mL, 36 mmol) was added. The mixture was stirred for 1 hour at room temperature and then the solvent was evaporated. The crude was purified by flash chromatography with ethyl acetate-petroleum ether (7-3) to afford the title compound (0.33 g, 57% yield).

MS (ES) (m/z): 239.1 [M+H]$^+$.

$^1$H-NMR (DMSO-d$_6$) δ: 11.76 (br. s., 1 H), 8.26-8.38 (m, 1 H), 4.56 (t, 1 H), 3.82 (dd, 2 H), 3.40-3.47 (m, 2 H), 1.71-1.81 (m, 2 H).

Preparation 21

3-(5-Trifluoromethyl-2,4-dioxo-3,4-dihydro-2H-pyrimidin-1-yl)-propionaldehyde (Prep21)

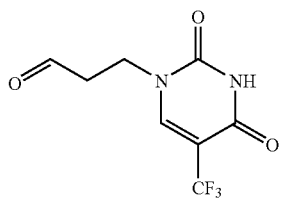

1-(3-Hydroxy-propyl)-5-trifluoromethyl-1H-pyrimidine-2,4-dione (Prep20, 100 mg, 0.42 mmol) was dissolved in dry THF (5 mL), the solution was then cooled to 0° C. and Dess-Martin periodinane (300 mg, 0.71 mmol) was added. The mixture was stirred at 0° C. for 1.5 hours. Et$_2$O was added and the mixture washed with aqueous saturated NaHCO$_3$ solution. The organic phase was dried (Na$_2$SO$_4$) and evaporated. The crude was purified by flash chromatography with ethyl acetate-petroleum ether (1-1) to give 50 mg of title compound (68% yield).

MS (ES) (m/z): 237.2 [M+H]$^+$.

Preparation 22

1-[4-(tert-Butyl-dimethyl-silanyloxy)-butyl]-5-trifluoromethyl-1H-pyrimidine-2, 4-dione (Prep22)

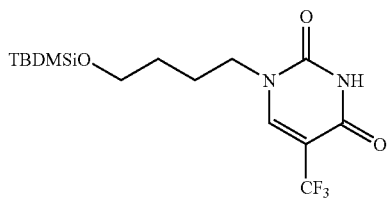

To a solution of 5-trifluoromethyl-1H-pyrimidine-2,4-dione (commercially available from Matrix, 1.07 g, 5.95 mmol) in dry DMF (10 mL), 50% NaH (371 mg, 7.7 mmol) was added The reaction mixture was then heated at 100° C. and stirred at this temperature for 1 hour. After cooling at room temperature, (3-iodo-botoxy)-tert-butyl-dimethyl-silane (2 mL, 7.7 mmol) was added and the reaction was stirred at room temperature overnight. The solvent was evaporated and the crude was dissolved in a 25%$_{aq}$ solution of citric acid and extracted with Et$_2$O. The organic phase was dried (Na$_2$SO$_4$) and evaporated. The crude was purified by flash chromatography with ethyl acetate-petroleum ether (2-8) to give 0.78 g of the title compound as a white solid (36% yield).

MS (ES) (m/z): 367.5 [M+H]$^+$.

$^1$H-NMR (CDCl$_3$) δ: 8.11 (br. s., 1 H), 7.67-7.76 (m, 1 H), 3.87 (dd, 2 H), 3.69 (dd, 2 H), 1.75-1.89 (m, 2 H), 1.52-1.62 (m, 2 H), 0.91 (s, 9 H), 0.07 (s, 6 H)

Preparation 23

1-(4-Hydroxy-butyl)-5-trifluoromethyl-1H-pyrimidine-2,4-dione (Prep23)

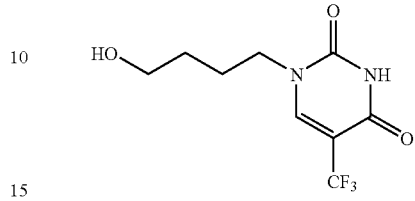

A solution of 1-[4-(tert-butyl-dimethyl-silanyloxy)-butyl]-5-trifluoromethyl-1H-pyrimidine-2,4-dione (Prep22, 260 mg, 0.71 mmol) in DCM (15 mL) was cooled at 0° C. and then TFA (820 µl, 1.1 mmol) was added. The mixture was stirred for 1 hour at room temperature and the solvent was evaporated. The crude was purified by flash chromatography with ethyl acetate-petroleum ether (7-3) to afford the title compound (132 mg, 74% yield).

MS (ES) (m/z): 253.1 [M+H]$^+$.

$^1$H-NMR (DMSO-d6) δ: 11.77 (br. s., 1 H), 8.39 (s, 1 H), 4.42 (t, 1 H), 3.75 (dd, 2 H), 3.35-3.45 (m, 2 H), 1.54-1.72 (m, 2 H), 1.33-1.46 (m, 2 H).

Preparation 24

4-(5-Trifluoromethyl-2,4-dioxo-3,4-dihydro-2H-pyrimidin-1-yl)-butyraldehyde (Prep24)

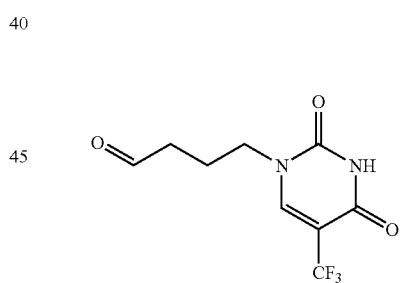

1-(4-Hydroxy-butyl)-5-trifluoromethyl-1H-pyrimidine-2,4-dione (Prep 23, 44 mg, 0.17 mmol) was dissolved in dry THF (5 mL), the solution was cooled to 0° C. and Dess-Martin periodinane (127 mg, 0.28 mmol) was added. The mixture was stirred at 0° C. for 1.5 hours. Et$_2$O was added and the solution washed with aqueous saturated NaHCO$_3$. The organic phase was dried (Na$_2$SO$_4$) and evaporated. The crude was purified by flash chromatography with ethyl acetate-petroleum ether (1-1) to give 22 mg of the title compound (50% yield).

MS (ES) m/z 251.1 [M+H]$^+$.

Preparation 25

2,4-Di-tert-butoxy-5-(3-methyl-thiophen-2-yl)-pyrimidine (Prep25)

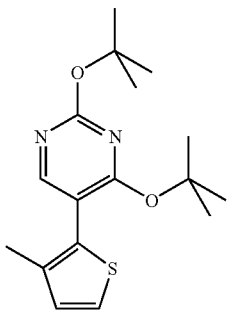

2,4-Di-tert-butoxy-pyrimidine-5-boronic acid (500 mg, 1.75 mmol) was dissolved in n-PrOH (5 mL) and then 2-bromo-3-methylthiophene (236 μl, 2.1 mmol), Na$_2$CO$_3$ (556 mg, 5.25 mmol), PPh$_3$ (133 mg, 0.52 mmol) and Pd(OAc)$_2$ (40 mg, 0.17 mmol) were added. The suspension was stirred at reflux for 2.5 hours. The solvent was evaporated and the crude was dissolved in water and extracted with Et$_2$O. The organic phase was dried (Na$_2$SO$_4$) and evaporated. The crude was purified by flash chromatography with ethyl acetate-petroleum ether (1-99) to give 170 mg of the title compound as a white solid (32% yield).

MS (ES) (m/z): 321.5 [M+H]$^+$.

$^1$H-NMR (CDCl$_3$) δ: 8.20 (s, 1 H), 7.48 (d, 1 H), 6.95 (d, 1 H), 2.14 (s, 3 H), 1.59 (s, 9 H), 1.56 (s, 9 H)

Preparation 26

5-(3-Methyl-thiophen-2-yl)-1H-pyrimidine-2,4-dione (Prep26)

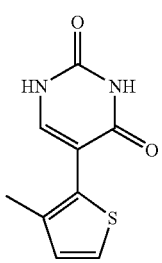

To a solution of 2,4-di-tert-butoxy-5-(3-methyl-thiophen-2-yl)-pyrimidine (Prep 25, 165 mg, 0.52 mmol) in dioxane (5 mL) 4N HCl$_{aq}$ in dioxane (1 mL) was added at 0° C. After stirring for 8 hours, the mixture was evaporated to give 110 mg of the title compound as white solid (quantitative yield)

MS (ES) (m/z): 209.2 [M+H]$^+$.

$^1$H-NMR (DMSO-d$_6$) δ: 11.27 (br. s., 1 H), 7.50 (s, 1 H), 7.40 (d, 1 H), 6.91 (d, 1 H), 2.13 (s, 3 H)

Preparation 27

1-[3-(tert-Butyl-dimethyl-silanyloxy)-propyl]-5-(3-methyl-thiophen-2-yl)-1H-pyrimidine-2,4-dione (Prep27)

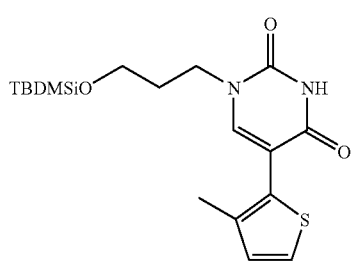

To a suspension of 5-(3-methyl-thiophen-2-yl)-1H-pyrimidine-2,4-dione (Prep26, 110 mg, 0.52 mmol) in dry DMF (10 mL), 60% NaH (31 mg, 0.78 mmol) was added. The mixture was then heated at 100° C. for 1 hour. (3-bromopropoxy)-tert-butyl-dimethyl-silane (180 μl, 0.7 mmol) was then added at room temperature and the reaction was stirred overnight. The solvent was evaporated and the crude was partitioned between NaHCO3 and Et$_2$O. The organic phase was dried (Na$_2$SO$_4$) and evaporated. The crude was purified by flash chromatography with ethyl acetate-petroleum ether (2-8) to give the title compound as a white solid (73 mg, 37% yield).

MS (ES) (m/z): 381.6 [M+H]$^+$.

$^1$H-NMR (DMSO-d$_6$) δ: 11.45 (br. s., 1 H), 7.72 (s, 1 H), 7.41 (d, 1 H), 6.92 (d, 1 H), 3.74-3.88 (m, 2 H), 3.65 (t, 2 H), 2.15 (d, 3 H), 1.82 (t, 2 H), 0.84 (s, 9 H), 0.01 (s, 6 H).

Preparation 28

1-(3-Hydroxy-propyl)-5-(3-methyl-thiophen-2-yl)-1H-pyrimidine-2,4-dione (Prep28)

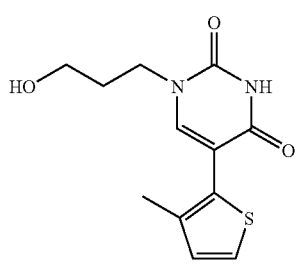

A solution of 1-[3-(tert-butyl-dimethyl-silanyloxy)-propyl]-5-(3-methyl-thiophen-2-yl)-1H-pyrimidine-2,4-dione (Prep 27, 73 mg, 0.2 mmol) in dioxane (8 mL) was cooled at 0° C. and then 4N HCl in dioxane (0.5 mL) was added. The mixture was stirred for 1 hour at room temperature and then the solvent was evaporated. The crude was purified by trituration with diisopropylether to afford the title compound as a white solid (36 mg, 72% yield).

MS (ES) (m/z): 267.3 [M+H]$^+$.

$^1$H-NMR (DMSO-d$_6$) δ: 11.48 (s, 1 H), 7.76 (s, 1 H), 7.42 (d, 1 H), 6.92 (d, 1 H), 4.47 (br. s., 1 H), 3.80 (dd, 2 H), 3.45 (dd, 2 H), 2.16 (s, 3 H), 1.77 (dt, 2 H)

Preparation 29

3-[5-(3-Methyl-thiophen-2-yl)-2,4-dioxo-3,4-dihydro-2H-pyrimidin-1-yl]-propionaldehyde (Prep29)

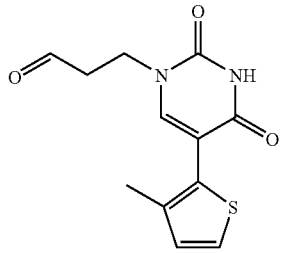

1-(3-Hydroxy-propyl)-5-(3-methyl-thiophen-2-yl)-1H-pyrimidine-2,4-dione (Prep 28.36 mg, 0.13 mmol) was dissolved in dry THF (5 mL), the solution was cooled to 0° C. and then Dess-Martin periodinane (97 mg, 0.22 mmol) was added under nitrogen. The mixture was stirred at room temperature for 1.5 hours. Ethyl acetate was added and the solution was washed with aqueous saturated NaHCO$_3$ solution. The organic phase was dried (Na$_2$SO$_4$) and evaporated. The crude was purified by flash chromatography with ethyl acetate-petroleum ether (7-3) to give 17 mg of the title compound (50% yield).

MS (ES) (m/z): 265.3 [M+H]$^+$.

Preparation 30: 1-[4-(tert-Butyl-dimethyl-silanyloxy)-butyl]-5-(3-methyl-thiophen-2-yl)-1H-pyrimidine-2,4-dione (Prep30)

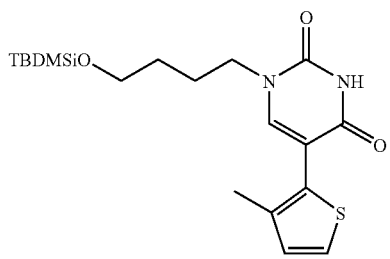

To a solution of 5-(3-methyl-thiophen-2-yl)-1H-pyrimidine-2,4-dione (Prep 26, 250 mg, 1.2 mmol) in DMF (10 mL), 60% NaH (58 mg, 1.44 mmol) was added portionwise. The reaction was then heated to 70° C. and this temperature was maintained for 1.5 hour. After cooling to room temperature, (4-iodo-butoxy)-tert-butyl-dimethyl-silane (452 mg, 1.44 mmol) was then added dropwise and the reaction was stirred for 24 hours. Water (30 mL) was added and the product was extracted with Et$_2$O. The organic phase was dried (Na$_2$SO$_4$) and evaporated. The crude was purified by flash chromatography with ethyl acetate-petroleum ether (15-85) followed by DCM/MeOH (70:30) to give the title compound as a yellow oil (110 mg, 23% yield).

MS (ES) (m/z): 395.6 [M+H]$^+$.

Preparation 31

1-(4-Hydroxy-butyl)-5-(3-methyl-thiophen-2-yl)-1H-pyrimidine-2,4-dione (Prep31)

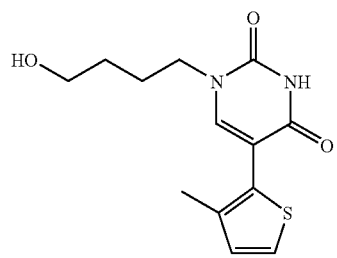

A solution of 1-[4-(tert-Butyl-dimethyl-silanyloxy)-butyl]-5-(3-methyl-thiophen-2-yl)-H-pyrimidine-2,4-dione (P30, 110 mg, 0.27 mmol) in dioxane (2 mL) was cooled at 0° C. and then 4N HCl in dioxane (1 mL) was added dropwise. The mixture was stirred for 30 minutes at room temperature and then the solvent was evaporated. The crude was purified by flash chromatography with DCM-MeOH (95-5) to afford the title compound (31 mg, 41% yield).

MS (ES) (m/z): 281.3 [M+H]$^+$.

$^1$H-NMR (DMSO-d$_6$) δ: 11.46 (br. s., 1 H), 7.83 (s, 1 H), 7.43 (d, 1 H), 6.93 (d, 1 H), 4.42 (t, 1 H), 3.75 (t, 2 H), 3.36-3.45 (m, 2 H), 2.16 (s, 3 H), 1.53-1.71 (m, 2 H), 1.37-1.48 (m, 2 H)

Preparation 32

4-[5-(3-Methyl-thiophen-2-yl)-2,4-dioxo-3,4-dihydro-2H-pyrimidin-1-yl]-butyraldehyde (Prep32)

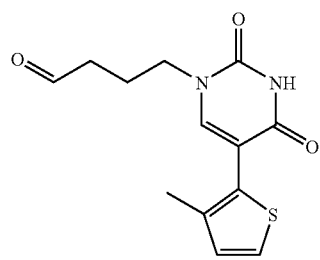

1-(4-Hydroxy-butyl)-5-(3-methyl-thiophen-2-yl)-1H-pyrimidine-2,4-dione (Prep 31, 30 mg, 0.11 mmol) was dissolved in dry DCM (2 mL), the solution was cooled to 0° C. and Dess-Martin periodinane (113 mg, 0.26 mmol) was added portionwise under nitrogen. The mixture was stirred at room temperature for 1.5 hours. Ethyl acetate was added and the solution washed with aqueous saturated Na$_2$S$_2$O$_3$ (3 mL) and NaHCO$_3$ (3 mL). The organic phase was dried (Na$_2$SO$_4$) and evaporated to give 30 mg of the title compound that was used in the next step without further purification (98% yield).

MS (ES) (m/z): 279.3 [M+H]$^+$.

Preparation 33

(2-Cyano-3-ethoxy-acryloyl)-carbamic acid ethyl ester (Prep33)

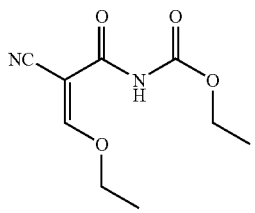

N-(Cyanoacethyl)uretane (5 g, 32 mmol), ethylortoformiate (4.74 g, 32 mmol) and acetic anhydride (8 mL, 85 mmol) were boiled under reflux at 160 C for 1 hour. The crystalline product separated on cooling washed with petroleum ether and crystallized from benzene to give the title compound as a pink solid (4.35 g, 62% yield)

MS (ES) (m/z): 213.2 [M+H]$^+$.

$^1$H-NMR (DMSO-d$_6$) δ: 8.17 (s, 1 H), 7.82 (br. s., 1 H), 4.41 (q, 2 H), 4.28 (q, 2 H), 1.47 (t, 3 H), 1.34 (t, 3 H).

Preparation 34

1-(3,3-Diethoxy-propyl)-2,4-dioxo-1,2,3,4-tetrahydro-pyrimidine-5-carbonitrile (Prep34)

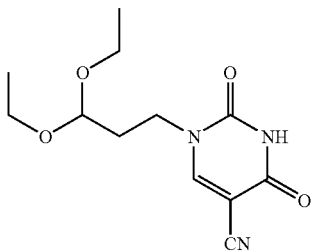

(2-Cyano-3-ethoxy-acryloyl)-carbamic acid ethyl ester (Prep 33, 300 mg, 1.42 mmol) was suspended in water (20 mL); 3,3-diethoxypropylamine (460 μl, 2.84 mmol) was added and the mixture warmed at 80° C. for 10 minutes. The reaction mixture was lyophilized and the residue was purified by flash chromatography with petroleum ether-ethyl acetate (1-1) to give 350 mg of the title compound (91% yield)

MS (ES) (m/z): 268.3 [M+H]$^+$.

$^1$H-NMR (DMSO-d$_6$) δ: 11.93 (br. s., 1 H), 8.63 (s, 1 H), 4.55 (t, 1 H), 3.79 (t, 2 H), 3.49-3.60 (m, 2 H), 3.35-3.46 (m, 2 H), 1.86-1.99 (m, 2 H), 1.09 (t, 6 H).

Preparation 35

2,4-Dioxo-1-(3-oxo-propyl)-1,2,3,4-tetrahydro-pyrimidine-5-carbonitrile (Prep35)

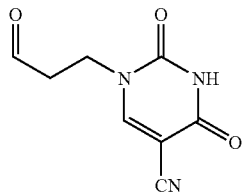

1-(3,3-diethoxy-propyl)-2,4-dioxo-1,2,3,4-tetrahydro-pyrimidine-5-carbonitrile (Prep 34, 50 mg, 0.21 mmol) was dissolved in dioxane (5 mL) and 1N HCl$_{aq}$ (500 μl) was added. The mixture was warmed at 60° C. for 15 minutes. The solvents were evaporated and the residue submitted to liophilization to give 53 mg of the title compound (quantitative yield).

MS (ES) (m/z): 194.2 [M+H]$^+$.

$^1$H-NMR (DMSO-d$_6$) δ: 11.96 (s, 1 H), 9.63 (t, 1 H), 8.66 (s, 1 H), 3.97 (t, 2 H), 2.90 (t, 2 H).

Preparation 36

3-Benzoyl-5-iodo-1H-pyrimidine-2,4-dione (Prep36)

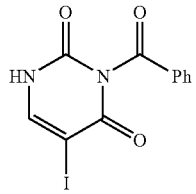

A solution of 5-iodouracil (commercially available from Aldrich, 2 g, 8.4 mmol) in dry pyridine (20 mL) was added dropwise to a solution of benzoyl chloride (3.5 g, 25.3 mmol) in pyridine (10 mL). The mixture was stirred at room temperature for 3 hours. Water (70 mL) was added and the product extracted with ethyl acetate. The organic phase was washed with a saturated solution of NH$_4$Cl and then with 2% HCl$_{aq}$ (40 mL×4 times) The solvent was removed under vacuum and the residue was triturated with i-Pr$_2$O to give the title compound as white solid (2.6 g, 90% yield).

MS (ES) (m/z): 343.2 [M+H]$^+$.

$^1$H-NMR (DMSO-d$_6$) δ: 11.90 (br. s., 1 H), 8.13 (s, 1 H), 7.95-8.01 (m, 2 H), 7.75-7.82 (m, 1 H), 7.57-7.63 (m, 2 H)

Preparation 37

3-Benzoyl-1-(3,3-dimethoxy-propyl)-5-iodo-1H-pyrimidine-2,4-dione (Prep37)

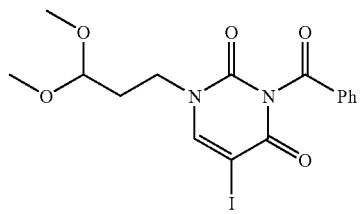

3-Benzoyl-5-iodo-1H-pyrimidine-2,4-dione (Prep 36, 2.1 g, 6.13 mmol), $K_2CO_3$ (846 mg, 6.13 mmol) and 3-bromo-1,1dimethoxy-propane (1 mL, 7.4 mmol) were dissolved in dry DMF under Nitrogen (8 mL). After stirring the reaction at room temperature for 48 h, water was added and the product extracted with diethylether. The organic phase was dried ($Na_2SO_4$) and evaporated. The crude was purified by flash chromatography with ethyl acetate-petroleum ether (35-65) to give 2.5 g of the title compound (91% yield).

MS (ES) (m/z): 445.2 $[M+H]^+$.

Preparation 38

3-(3-Benzoyl-5-iodo-2,4-dioxo-3,4-dihydro-2H-pyrimidin-1-yl)-propionaldehyde (Prep38)

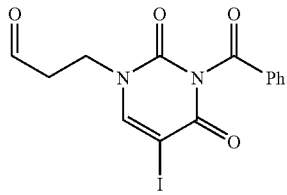

Method a)

3-Benzoyl-1-(3,3-dimethoxy-propyl)-5-iodo-1H-pyrimidine-2,4-dione (Prep 37, 2.6 g, 5.63 mmol) was dissolved in dioxane (10 mL) and 1N $HCl_{aq}$ (22.5 mL) was added. The mixture was stirred at room temperature for 4.5 h. Water was added and the product extracted with ethyl acetate, the organic phase washed with a 5% solution of $NaHCO_3$. The organic phase was dried ($Na_2SO_4$), evaporated and the crude was redissolved in dioxane (10 mL) and treated with a 2M solution of HCl. After work-up as above described, the crude was purified by flash chromatography with ethyl acetate-petroleum ether (3-7) to give the title compound as a white solid (1.48 g, 66% yield).

MS (ES) (m/z): 399.2 $[M+H]^+$.

$^1$H-NMR (DMSO-$d_6$) δ: 9.65 (d, 1 H), 8.40 (s, 1 H), 7.97-8.02 (m, 2 H), 7.75-7.82 (m, 1 H), 7.57-7.63 (m, 2 H), 4.01 (t, 2 H), 2.91 (td, 2 H)

Method b)

1-[3,3-bis(methyloxy)propyl]-5-iodo-3-(phenylcarbonyl)-2,4(1H,3H)-pyrimidinedione (5.77 g, 12.99 mmol) was dissolved in 1,4-dioxane (33 ml), then 1N $HCl_{aq}$ (26.0 ml, 26.0 mmol) was added and the mixture was stirred at 60° C. for 1 hour 30 minutes. 5 mL of 6N $HCl_{aq}$ (30 mmol) were added and the mixture was stirred at 60° C. After 2 hours further 5 mL of 6N $HCl_{aq}$ (30 mmol) were added and the solution stirred for further 1.5 hour (a white precipitate was formed). The reaction mixture was then concentrated under reduced pressure and partitioned between water and AcOEt. Organic phase washed with a saturated solution of $NaHCO_3$, dried over $Na_2SO_4$ and solvent was eliminated under reduced pressure giving the title compound (4.85 g, 12.20 mmol, 94% yield) as a white solid.

MS (ES) (m/z): 398.95 $[M+H]^+$.

$^1$H-NMR (DMSO-$d_6$) δ: 9.65 (s, 1 H), 8.42 (s, 1 H), 8.05 (d, 2 H), 7.78-7.82 (m, 1 H), 7.59-7.63 (m, 2 H), 4.02 (t, 2 H), 2.92 (t, 2 H)

Preparation 39

3-Benzoyl-5-iodo-1-{3-[(1S,5R)-1-(4-trifluoromethyl-phenyl)-3-aza-bicyclo[3.1.0]hex-3-yl]-propyl}-1H-pyrimidine-2,4-dione (Prep39)

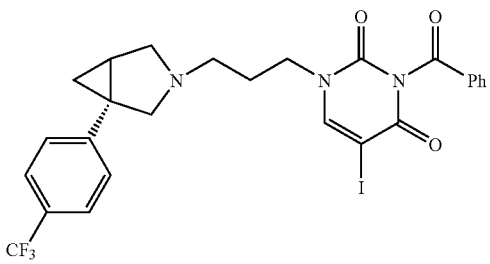

To a solution of 3-(3-benzoyl-5-iodo-2,4-dioxo-3,4-dihydro-2H-pyrimidin-1-yl)-propionaldehyde (Prep 38, 700 mg, 1.7 mmol) in dichloromethane (20 mL), (1S,5R)-1-(4-trifluoromethyl-phenyl)-3-aza-bicyclo[3.1.0]hexane (Prep 4, 399 mg, 1.7 mmol), AcOH (158 mg, 2.5 mmol) and $NaBH(AcO)_3$ (410 mg, 1.9 mmol) were added at 0° C. The mixture was stirred at 0° C. for further 1 hours. Water was added and the solvent was evaporated under vacuum, the residue re-dissolved in ethyl acetate and the mixture washed with a 5% solution of aqueous $NaHCO_3$. The organic phase was dried ($Na_2SO_4$) and evaporated. The crude was purified by flash chromatography with DCM-MeOH—$NH_4OH$ (97-3-1) to give the title compound as a white solid (880 mg, 83% yield).

MS (ES) (m/z): 610.2 $[M+H]^+$.

$^1$H-NMR (DMSO-$d_6$) δ: 8.42 (s, 1 H), 7.92-8.01 (m, 2 H), 7.73-7.83 (m, 1 H), 7.56-7.67 (m, 4 H), 7.30-7.39 (m, 2 H), 3.83 (t, 2 H), 3.33-3.49 (m, 2 H), 3.06 (d, 1 H), 2.54 (t, 2 H), 2.41 (dd, 1 H), 1.93 (dt, 1 H), 1.76-1.87 (m, 2 H), 1.43 (dd, 1 H), 0.87 (dd, 1 H)

Preparation 40

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40)

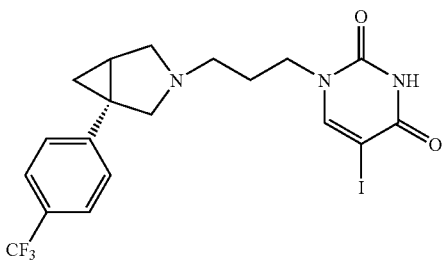

3-Benzoyl-5-iodo-1-{3-[(1S,5R)-1-(4-trifluoromethyl-phenyl)-3-aza-bicyclo[3.1.0]hex-3-yl]-propyl}-1H-pyrimidine-2,4-dione (Prep 39, 840 mg, 1.38 mmol) was dissolved in 10% $NH_3$ in MeOH solution (5 mL). The mixture was stirred at room temperature for 1 hour, the solvent was then evaporated under vacuum and the crude purified by flash chromatography with DCM-MeOH—NH₄OH (98-2-1) to give the title compound as a white solid (515 mg, 74% yield).

MS (ES) (m/z): 506.3 [M+H]⁺.

¹H-NMR (DMSO-d₆) δ: 11.56 (s, 1 H), 8.16 (s, 1 H), 7.58-7.65 (m, 2 H), 7.30-7.37 (m, 2 H), 3.73 (t, 2 H), 3.34 (d, 1 H), 3.02 (d, 1 H), 2.51-2.54 (m, 1 H), 2.46 (t, 2 H), 2.38 (dd, 1 H), 1.91 (ddd, 1 H), 1.70-1.82 (m, 2 H), 1.42 (dd, 1 H), 0.85 (dd, 1 H)

Preparation 41

3-Benzoyl-1-(3-chloro-propyl)-5-iodo-1H-pyrimidine-2,4-dione (Prep41)

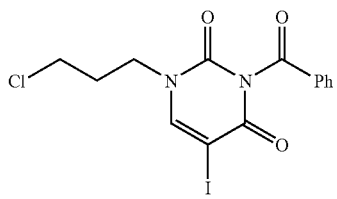

3-Benzoyl-5-iodo-1H-pyrimidine-2,4-dione (Prep36, 3 g, 8.77 mmol) and K₂CO₃ (1.2 g, 8.77 mmol) were suspended in dry DMF (45 mL) and stirred at room temperature for 1 h. Then, bromo-chloro-propane (2.7 mL, 17.5 mmol) was added dropwise and the mixture stirred at room temperature overnight. Water was added and the mixture was extracted with ethyl acetate. The organic phase was dried (Na₂SO₄), filtered and evaporated to give the title compound as a pale yellow oil (3.6 g, 98% yield).

MS (ES) (m/z): 418.6 [M+H]⁺.

Preparation 42

3-Benzoyl-1-(3-chloro-propyl)-5-pyridin-3-yl-1H-pyrimidine-2,4-dione (Prep42)

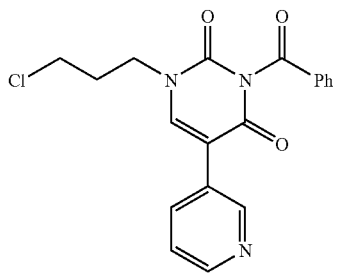

3-Benzoyl-1-(3-chloro-propyl)-5-iodo-1H-pyrimidine-2,4-dione (Prep 41,500 mg, 1.2 mmol) was dissolved in degassed DME-water solution (5-1, 35 mL). Pyridine-3-boronic acid (629 mg, 1.8 mmol), Na₂CO₃ (380 mg, 3.6 mmol), 2-(dicyclohexylphosphino)biphenyl (84 mg, 0.24 mmol) and Pd(PPh₃)₄ (250 mg, 0.24 mmol) were added and the mixture was refluxed for 3 hours. The solvents were evaporated under vacuum and the residue was filtered over a SCX cartridge washing with MeOH and eluting with MeOH/NH3 95:5. The crude was purified by flash chromatography with DCM-MeOH—NH₄OH (from 98-2-0.2 to 95:5:05) to give the title compound (90 mg, 20% yield)

MS (ES) (m/z): 370.8 [M+H]⁺..

Preparation 43

1-(3-Chloro-propyl)-5-pyridin-3-yl-1H-pyrimidine-2,4-dione (Prep43)

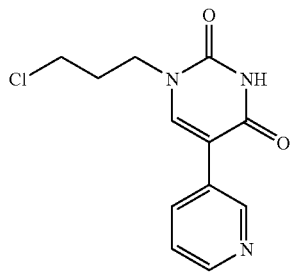

3-Benzoyl-1-(3-Chloro-propyl)-5-pyridin-3-yl-1H-pyrimidine-2,4-dione (Prep42, 90 mg, 0.24 mmol) was dissolved in a solution of 3% NH₃ in MeOH (5 mL). The mixture was stirred at room temperature over night, the solvent was then evaporated under vacuum and the residue was passed over a SCX cartridge to give 42 mg of the title compound that was used in the next step without further purification (66% yield)

MS (ES) (m/z): 266.7 [M+H]⁺.

Preparation 44

3-Benzoyl-1-(4-chloro-butyl)-5-iodo-1H-pyrimidine-2,4-dione (Prep44)

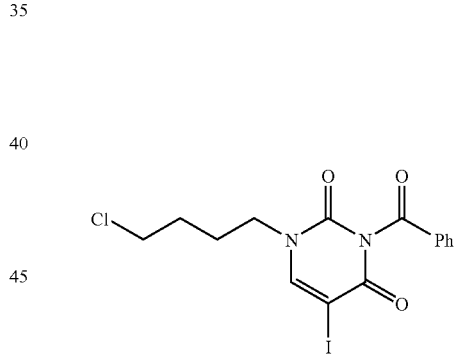

3-Benzoyl-5-iodo-1H-pyrimidine-2,4-dione (Prep36, 2.5 g, 7.3 mmol), K₂CO₃ (1 g, 7.3 mmol) and 1-bromo-4-chlorobutane (2.10 mL, 18 mmol) were suspended in dry DMF (10 mL). After stirring the reaction at room temperature overnight, water was added and the mixture was extracted with ethyl acetate. The organic phase was dried (Na₂SO₄), filtered and evaporated; the crude was purified by flash chromatography with petroleum ether-ethyl acetate (7-3) to give the title compound as a white solid (3 g, 98% yield).

MS (ES) (m/z): 433.6 [M+H]⁺.

¹H-NMR (CDCl₃) δ: 7.89-7.93 (m, 2 H), 7.73 (s, 1 H), 7.64-7.70 (m, 1 H), 7.48-7.54 (m, 2 H), 3.84 (t, 2 H), 3.60 (t, 2 H), 1.81-1.98 (m, 4 H)

Preparation 45

3-Benzoyl-1-(4-chloro-butyl)-5-(2-methyl-pyridin-4-yl)-1H-pyrimidine-2,4-dione (Prep45)

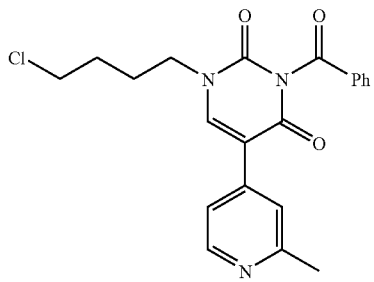

3-Benzoyl-1-(4-chloro-butyl)-5-iodo-1H-pyrimidine-2,4-dione (Prep 44, 433 mg, 1 mmol) was dissolved in degassed DME-water solution (5-1, 30 mL). 2-methyl-pyridine 4-boronic acid (205 mg, 1.5 mmol), $Na_2CO_3$ (212 mg, 2 mmol), 2-(dicyclohexylphosphino)biphenyl (70 mg, 0.2 mmol) and $Pd(PPh_3)_4$ (231 mg, 0.2 mmol) were added and the mixture was refluxed for 6 hours. The solvents were evaporated under vacuum and the crude was partitioned between ethyl acetate and water. The organic phase was dried ($Na_2SO_4$) and evaporated; the crude was purified by flash chromatography with DCM-MeOH—$NH_4OH$ (98-2-0.2) and SCX cartridge washing with MeOH and eluting with MeOH/NH3 95:5 to give the title compound (100 mg, 25% yield).

MS (ES) (m/z): 398.5 $[M+H]^+$.

Preparation 46

1-(4-Chloro-butyl)-5-(2-methyl-pyridin-4-yl)-1H-pyrimidine-2,4-dione (Prep46)

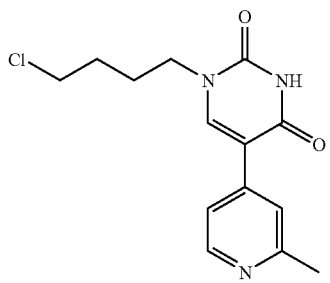

3-Benzoyl-1-(4-chloro-butyl)-5-(2-methyl-pyridin-4-yl)-1H-pyrimidine-2,4-dione (Prep 45, 100 mg, 0.25 mmol) was dissolved in a solution of 3% $NH_3$ in MeOH (5 mL). The mixture was stirred at room temperature for 3 hours, the solvent was then evaporated under vacuum to give the title compound that was used in the next step without further purification.

MS (ES) (m/z): 294.7 $[M+H]^+$.

Preparation 47

3-Benzoyl-1-(4-chloro-butyl)-5-(2-methyl-pyridin-3-yl)-1H-pyrimidine-2,4-dione (Prep47)

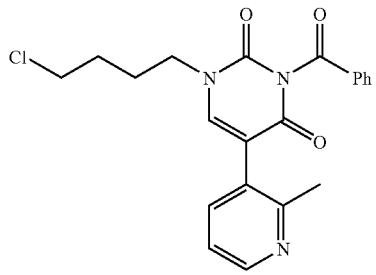

3-Benzoyl-1-(4-chloro-butyl)-5-iodo-1H-pyrimidine-2,4-dione (Prep 44, 541 mg, 1.25 mmol) was dissolved in degassed DME-water solution (5-1, 37.5 mL). 2-Methyl-pyridine 3-boronic acid (325 mg, 1.9 mmol), $Na_2CO_3$ (265 mg, 2.5 mmol), 2-(dicyclohexylphosphino)biphenyl (52 mg, 0.15 mmol) and $Pd(PPh_3)_4$ (288 mg, 0.25 mmol) were added and the mixture was refluxed for 3 hours. A second batch was run in parallel in the same reaction conditions on 3-Benzoyl-1-(4-chloro-butyl)-5-iodo-1H-pyrimidine-2,4-dione (Prep 44, 108 mg, 0.25 mmol) using 2-Methyl-pyridine 3-boronic acid (65 mg, 0.375 mmol), $Na_2CO_3$ (53 mg, 0.5 mmol), 2-(dicyclohexylphosphino)biphenyl (17.5 mg, 0.05 mmol) and $Pd(PPh_3)_4$ (57.75 mg, 0.05 mmol) dissolved in degassed DME-water solution (5-1, 7.5 mL). The crudes were then mixed and the solvents were evaporated under vacuum and the residue was partitioned between ethyl acetate and water. The organic phase was dried ($Na_2SO_4$) and evaporated; the crude was purified by flash chromatography with DCM-MeOH—$NH_4OH$ (98-2-0.2) and then loaded on SCX cartridge washing with MeOH and eluting with MeOH/NH3 95:5 to give the title compound (330 mg, 56% yield).

MS (ES) (m/z): 398.5 $[M+H]^+$.

Preparation 48

1-(4-Chloro-butyl)-5-(2-methyl-pyridin-3-yl)-1H-pyrimidine-2,4-dione (Prep48)

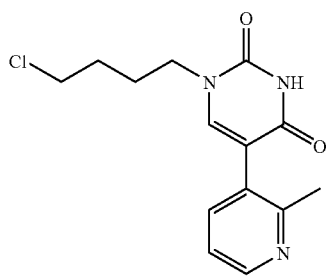

3-Benzoyl-1-(4-chloro-butyl)-5-(2-methyl-pyridin-3-yl)-1H-pyrimidine-2,4-dione (Prep 47, 330 mg, 0.8 mmol) was dissolved in a solution of 3% $NH_3$ in MeOH (15 mL). The mixture was stirred at room temperature for 3 hours, the solvent was then evaporated under vacuum. The residue was redissolved in MeOH and filtered on a SCX cartridge to give 220 mg of the title compound as a yellow oil (90% yield).

MS (ES) (m/z): 294.7 $[M+H]^+$.

Preparation 49

2,4-Dimethoxy-5-(6-methyl-pyridin-2-yl)-pyrimidine (Prep49)

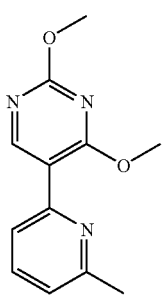

2,4-Di-methoxy-pyrimidine-5-boronic acid (500 mg, 2.72 mmol) was dissolved in degassed n-PrOH (40 mL) and then 2-bromo-6-methylpyridine (660 mg, 3.8 mmol), $Na_2CO_3$ (865 mg, 8.16 mmol), $PPh_3$ (215 mg, 0.8 mmol) and $Pd(OAc)_2$ (50 mg, 0.22 mmol) were added. The suspension was stirred at reflux for 4 hours. The solvent was evaporated and the crude was partitioned between water and $Et_2O$. The organic phase was dried ($Na_2SO_4$) and evaporated. The crude was purified by flash chromatography with ethyl acetate-petroleum ether (2-8) to give 300 mg of the title compound (47% yield).

MS (ES) (m/z): 232.3 [M+H]$^+$.

$^1$H-NMR (DMSO-$d_6$) δ: 8.83 (s, 1 H), 7.62-7.78 (m, 2 H), 7.21 (d, 1 H), 4.02 (s, 3 H), 3.97 (s, 3 H), 2.52 (s, 3 H).

Preparation 50

5-(6-Methyl-pyridin-2-yl)-1H-pyrimidine-2,4-dione hydrochloride (Prep50)

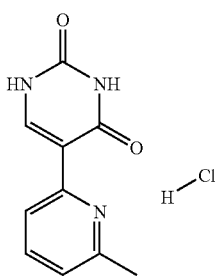

To a solution of 2,4-dimethoxy-5-(6-methyl-pyridin-2-yl)-pyrimidine (Prep49, 300 mg, 1.3 mmol) in MeOH (8 mL) 2N $HCl_{aq}$ (2 mL) was added. After stirring for 8 hours at room temperature, the solvents were evaporated. The crude was triturated with ethyl acetate to give 195 mg of the title compound (74% yield)

MS (ES) (m/z): 205.2 [M+H]$^+$.

$^1$H-NMR (CDCl$_3$) δ: 11.28 (br. s., 2 H), 8.24 (s, 1 H), 8.05 (d, 1 H), 7.65 (t, 1 H), 7.11 (d, 1 H), 2.47 (s, 3 H).

Preparation 51

1-(4-Chloro-butyl)-5-(6-methyl-pyridin-2-yl)-1H-pyrimidine-2,4-dione (Prep51)

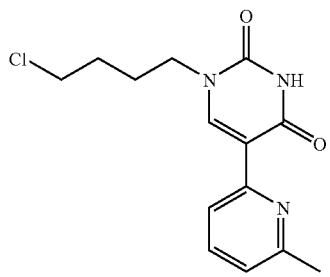

5-(6-Methyl-pyridin-2-yl)-1H-pyrimidine-2,4-dione hydrochloride (Prep 50, 50 mg, 0.208 mmol) and $K_2CO_3$ (43 mg, 0.312 mmol) were suspended in dry DMF (2 mL) and stirred for 1 h at room temperature. Then a solution of bromo-chloro-butane (71.3 mg, 0.416 mmol) in dry DMF (0.5 mL) was added dropwise and the mixture stirred for 48 hrs at room temperature. A second run of reaction was performed using 5-(6-Methyl-pyridin-2-yl)-1H-pyrimidine-2,4-dione (135 mg, 0.563 mmol), $K_2CO_3$ (116 mg, 0.8445 mmol) and bromo-chloro-butane (193 mg, 1.126 mmol). After stirring the reactions at room temperature for 48 hours, the two mixtures were mixed. Water was added and the mixture was extracted with ethyl acetate. The organic phase was dried ($Na_2SO_4$), filtered and evaporated; the crude was purified by flash chromatography with DCM-MeOH—NH$_4$OH (98-2-0.2) to give the title compound as a pale yellow solid (96 mg, 43% yield).

MS (ES) (m/z): 294.7 [M+H]$^+$.

$^1$H-NMR (DMSO-$d_6$) δ: 11.50 (br. s., 1 H), 8.47 (s, 1 H), 8.03 (d, 1 H), 7.67 (dd, 1 H), 7.13 (d, 1 H), 3.83-3.93 (m, 2 H), 3.63-3.73 (m, 2 H), 2.50 (s, 3 H), 1.72-1.82 (m, 4 H).

Preparation 52

2,4-Dimethoxy-5-o-tolyl-pyrimidine (Prep52)

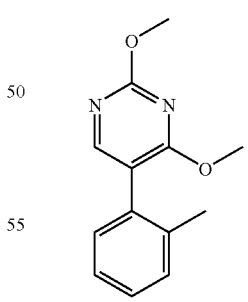

5-Iodo-2,4-dimethoxy-pyrimidine (1 g, 3.75 mmol) was dissolved in degassed n-PrOH (25 mL) and then 2-methylphenyl boronic acid (766 mg, 3.8 mmol), $Na_2CO_3$ (865 mg, 8.16 mmol), $PPh_3$ (215 mg, 0.8 mmol) and $Pd(OAc)_2$ (50 mg, 5.67 mmol) were added. The suspension was stirred at reflux for 3 hours. The solvent was evaporated and the crude was partitioned between water and DCM. The organic phase was dried ($Na_2SO_4$) and evaporated. The crude was purified by flash chromatography with ethyl acetate-petroleum ether (1-9) to give 400 mg of the title compound (46% yield).

MS (ES) m/z 231.2 [M+H]+.

Preparation 53

5-o-Tolyl-1H-pyrimidine-2,4-dione (Prep53)

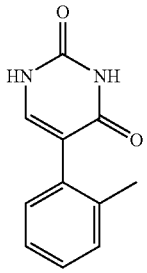

To a solution of 2,4-dimethoxy-5-o-tolyl-pyrimidine (Prep52, 400 mg, 1.7 mmol) in MeOH (10 mL) 2N HCl$_{aq}$ (3 mL) was added. After refluxing for 48 hours, the solvents were evaporated. The crude was triturated with ethyl acetate to give 310 mg of the desired product (90% yield) that was used in the next step without further purification.

MS (ES) (m/z): 203.2 [M+H]+.

Preparation 54

1-(3,3-Diethoxy-butyl)-2,4-dioxo-1,2,3,4-tetrahydro-pyrimidine-5-carbonitrile (Prep54)

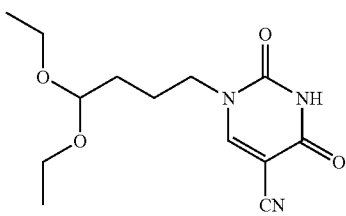

(2-Cyano-3-ethoxy-acryloyl)-carbamic acid ethyl ester (Prep32, 500 mg, 2.3 mmol) was suspended in water (20 mL) and 3,3-diethoxybutylamine (816 µl, 4.7) was added and the mixture warmed at 80° C. for 10 minutes. The reaction mixture was lyophilized and the residue was purified by flash chromatography with petroleum ether-ethyl acetate (1-1) to give 553 mg of the title compound as a white solid (83% yield).

MS (ES) (m/z): 282.3 [M+H]+.

$^1$H-NMR (DMSO-d$_6$) δ: 11.92 (s, 1 H), 8.68 (s, 1 H), 4.45 (t, 1 H), 3.71 (t, 2 H), 3.37-3.60 (m, 4 H), 1.57-1.70 (m, 2 H), 1.46-1.56 (m, 2 H), 1.10 (t, 6 H)

Preparation 55

2,4-Dioxo-1-(4-oxo-butyl)-1,2,3,4-tetrahydro-pyrimidine-5-carbonitrile (Prep55)

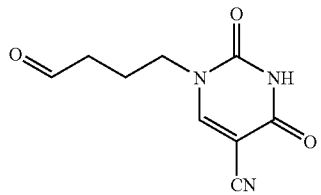

1-(3,3-Diethoxy-butyl)-2,4-dioxo-1,2,3,4-tetrahydro-pyrimidine-5-carbonitrile (Prep 54, 200 mg, 0.71 mmol) was dissolved in dioxane (8 mL) and 1N HCl$_{aq}$ (1 mL) was added. The mixture was warmed at 60° C. for 20 minutes. The solvents were evaporated, the residue was submitted to lyophilization, to give 150 mg of the title compound that was used in the next step without further purification (quantitative yield).

MS (ES) (m/z): 207.2 [M+H]+.

$^1$H-NMR (DMSO-d$_6$) δ: 11.93 (s, 1 H), 9.64 (t, 1 H), 8.67 (s, 1 H), 3.73 (t, 2 H), 2.53-2.56 (m, 2 H), 1.79-1.92 (m, 2 H).

Preparation 56

2,4-Dimethoxy-5-(6-methyl-pyridin-3-yl)-pyrimidine (Prep56)

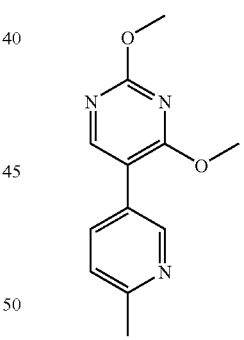

2,4-Dimethoxy-pyrimidine-5-boronic acid (commercially available from Aldrich, 830 mg, 4.5 mmol) was dissolved in degassed n-PrOH (10 mL) and then 3-bromo-6-methylpyridine (600 mg, 3.5 mmol), Na$_2$CO$_3$ (956 mg, 9 mmol), PPh$_3$ (90 mg, 0.35 mmol) and Pd(OAc)$_2$ (78 mg, 0.35 mmol) were added. The suspension was stirred at reflux for 1.5 hours. The solvent was evaporated under vacuum and the crude was partitioned between water and ethyl acetate. The organic phase was dried (Na$_2$SO$_4$) and evaporated. The crude was purified by SCX cartridge washing with MeOH and then collecting the product with MeOH—NH$_4$OH (95-5) to give 500 mg of the title compound (62% yield).

MS (ES) (m/z): 232.3 [M+H]+.

Preparation 57

5-(6-Methyl-pyridin-3-yl)-1H-pyrimidine-2,4-dione hydrochloride (Prep57)

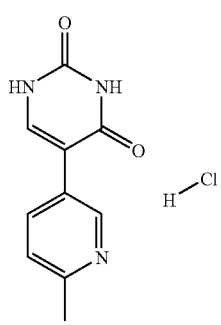

To a solution of 2,4-dimethoxy-5-(6-methyl-pyridin-3-yl)-pyrimidine (Prep56, 500 mg, 2.1 mmol) in MeOH (8 mL), 1N HCl$_{aq}$ (6 mL) was added. After refluxing the mixture for 6 hours, the solvents were evaporated to give 400 mg of the title compound (90% yield)

MS (ES) (m/z): 205.2 [M+H]$^+$.

Preparation 58

1-(3,3-Dimethoxy-propyl)-5-(6-methyl-pyridin-3-yl)-1H-pyrimidine-2,4-dione (Prep58)

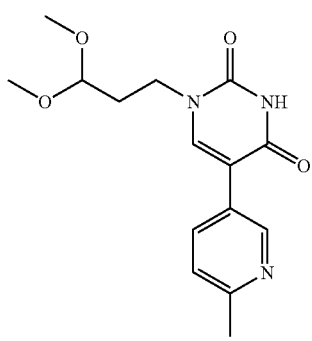

5-(6-methyl-pyridin-3-yl)-1H-pyrimidine-2,4-dione hydrochloride (Prep57, 385 mg, 1.62 mmol), K$_2$CO$_3$ (224 mg, 1.62 mmol) and 3-bromo-1,1dimethoxy-propane (commercially available from Aldrich, 183 mg, 1.0 mmol) were suspended in dry DMF (8 mL). After stirring the reaction at room temperature for 24 hours, additional 3-bromo-1,1dimethoxy-propane (180 mg, 0.98 mmol) was added portionwise over a period of 96 h. Water was added and the mixture washed with diethyl ether. The aqueous layer was then extracted with ethyl acetate. The organic phase was dried (Na$_2$SO$_4$) and evaporated to give 320 mg of the final compound that was used without further purification in the next step (48% yield).

MS (ES) (m/z): 410.4 [M+H]$^+$.

Preparation 59

3-[5-(6-Methyl-pyridin-3-yl)-2,4-dioxo-3,4-dihydro-2H-pyrimidin-1-yl]-propionaldehyde (Prep59)

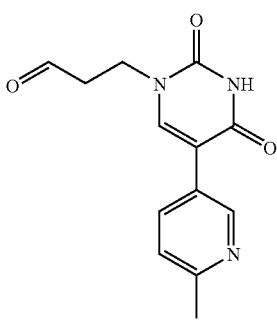

1-(3,3-Dimethoxy-propyl)-5-(6-methyl-pyridin-3-yl)-1H-pyrimidine-2,4-dione (Prep 58, 240 mg, 0.78 mmol) was dissolved in THF (4 mL) and 1N solution of HCl$_{aq}$ (1.5 mL) was added. The mixture was stirred at room temperature for 2 hours and then warmed at 45° C. and stirred for an additional hour at this temperature. After neutralization with a 5% solution of NaHCO$_3$ the mixture was extracted with ethyl acetate. The organic phase was dried (Na$_2$SO$_4$) and evaporated to give the title compound as foam (90 mg, 45% yield).

MS (ES) (m/z): 260.3 [M+H]$^+$.

Preparation 60

5-iodo-2,4-diethyl oxazole (Prep60)

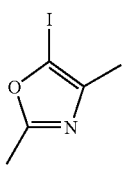

To a solution of 2,4-dimethyl-oxazole (commercially available from Aldrich, 1 g, 0.01 mol) in dry DMSO (10 mL) cooled to 0° C., iodine (3.8 g, 0.015 mol) was added portionwise. The mixture was stirred at room temperature for 4 days then a 10% solution of Na$_2$S$_2$O$_5$ was added. The mixture was basified with a saturated solution of NaHCO3, extracted with diethylether and evaporated under vacuum to obtain 850 mg of the title compound as yellow solid. (38%)

MS (ES) (m/z): 224.2 [M+H]$^+$.

Preparation 61

5-(2,4-Dimethyl-oxazol-5-yl)-2,4-dimethoxy-pyrimidine (Prep61)

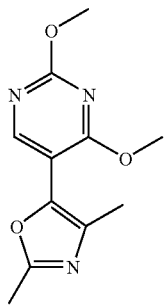

2,4-Dimethoxy-pyrimidine-5-boronic acid (840 mg, 4.6 mmol) was dissolved in degassed n-PrOH (40 mL) and then 5-iodo-2,4-dimethyl-oxazole (Prep60, 850 mg, 3.8 mmol), $Na_2CO_3$ (848 mg, 8 mmol), $PPh_3$ (332 mg, 1.3 mmol) and $Pd(OAc)_2$ (85 mg, 0.38 mmol) were added. The suspension was stirred at reflux for 4 hours. The solvent was evaporated under vacuum and the crude was partitioned between water and ethyl acetate. The organic phase was dried ($Na_2SO_4$) and evaporated. The crude was purified by SCX cartridge to give 600 mg of the title compound (66% yield).

MS (ES) (m/z): 236.2 $[M+H]^+$.

Preparation 62

5-(2,4-Dimethyl-oxazol-5-yl)-1H-pyrimidine-2,4-dione (Prep62)

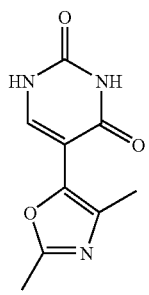

To a solution of 5-(2,4-Dimethyl-oxazol-5-yl)-2,4-dimethoxy-pyrimidine (Prep61, 600 mg, 2.5 mmol) in MeOH (40 mL) 2N $HCl_{aq}$ (10 mL) was added. After refluxing the mixture for 3 hours, the solvents were evaporated. The crude was triturated with acetone and filtered to give 480 mg of 5-(2,4-Dimethyl-oxazol-5-yl)-1H-pyrimidine-2,4-dione as a light brown powder (92% yield)

MS (ES) (m/z): 208.2 $[M+H]^+$.

Preparation 63

1-(3,3-Dimethoxy-propyl)-5-(2,4-dimethyl-oxazol-5-yl)-1H-pyrimidine-2,4-dione (Prep63)

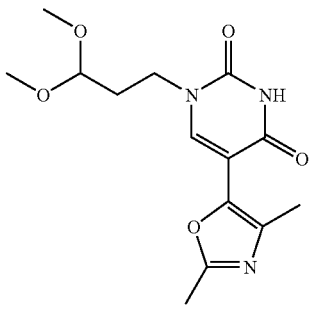

5-(2,4-Dimethyl-oxazol-5-yl)-1H-pyrimidine-2,4-dione (Prep62, 480 mg, 2.32 mmol) and $K_2CO_3$ (320 mg, 2.32 mmol) were suspended in dry DMF (6 ml) and stirred at room temperature for 1 h. A solution of 3-bromo-1,1dimethoxypropane (467 mg, 2.55 mmol) in dry DMF (2 mL) was added dropwise and the mixture stirred at room temperature for 72 hours. Water (80 mL) was added and the product extracted with ethyl acetate. The organic phase was dried ($Na_2SO_4$) and evaporated to give 377 mg of the final compound that was used without any other purification in the next step (53% yield).

MS (ES) (m/z): 310.3 $[M+H]^+$.

Preparation 64

3-[5-(2,4-Dimethyl-oxazol-5-yl)-2,4-dioxo-3,4-dihydro-2H-pyrimidin-1-yl]-propionaldehyde (Prep64)

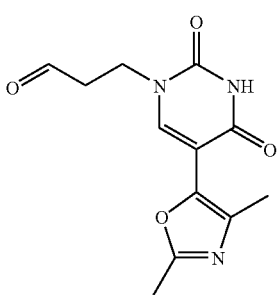

1-(3,3-Dimethoxy-propyl)-5-(2,4-dimethyl-oxazol-5-yl)-1H-pyrimidine-2,4-dione (Prep63, 150 mg, 0.49 mmol) was dissolved in THF (10 mL) and 1N $HCl_{aq}$ (3 mL) was added. The mixture was stirred at 45° C. for 1 hour. After cooling and neutralization with a saturated solution of $NaHCO_3$ the product was extracted with DCM. The organic phase was dried ($Na_2SO_4$) and evaporated to give 74 mg of the title compound (58% yield).

MS (ES) (m/z): 264.3 $[M+H]^+$.

Preparation 65

1-(4-Chloro-butyl)-5-(2,4-dimethyl-oxazol-5-yl)-1H-pyrimidine-2,4-dione (Prep65)

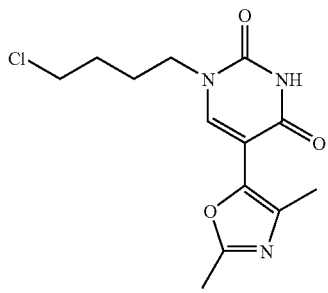

5-(2,4-Dimethyl-oxazol-5-yl)-1H-pyrimidine-2,4-dione (Prep61, 300 mg, 1.45 mmol) was dissolved in dry DMF (4 ml) and $K_2CO_3$ (300 mg, 2.17 mmol) was added. The mixture was stirred at room temperature for 1 h, then a solution of 1-bromo-4-chloro-butane (commercially available from Aldrich, 496 mg, 2.9 mmol) in dry DMF (1 ml) was added. After stirring the reaction at room temperature for 48 hours, water was added and the mixture was extracted with diethylether. The aqueous layer was then extracted with ethyl acetate. The organic phase was dried ($Na_2SO_4$), filtered and evaporated; the crude was used without further purification in the next step (200 mg, 47% yield).

MS (ES) (m/z): 298.2 $[M+H]^+$.

Preparation 66

5-(3-Fluoro-pyridin-4-yl)-2,4-dimethoxy-pyrimidine (Prep66)

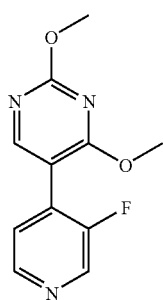

5-Iodo-2,4-dimethoxy-pyrimidine (commercially available from Matrix, 905 mg, 3.4 mmol) was dissolved in degassed n-PrOH (24 ml) and then 3-fluoropyridine-4-boronic acid (715 mg, 5.1 mmol), $Na_2CO_3$ (721 mg, 6.8 mmol), $PPh_3$ (84 mg, 0.34 mmol) and $Pd(OAc)_2$ (40 mg) were added. The suspension was stirred at reflux for 1.5 hours. The solvent was evaporated under vacuum and the crude was partitioned between water and ethyl acetate. The organic phase was dried ($Na_2SO_4$) and evaporated. The crude was purified by flash chromatography with DCM-MeOH 98-2 and by SCX cartridge washing with MeOH and then collecting the product with MeOH—$NH_4OH$ (95-5) to give 750 mg of the title compound (93% yield).

MS (ES) (m/z): 236.2 $[M+H]^+$.

Preparation 67

5-(3-Fluoro-pyridin-4-yl)-1H-pyrimidine-2,4-dione hydrochloride (Prep67)

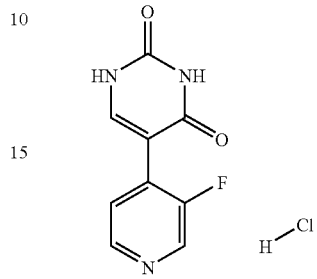

To a solution of 5-(3-Fluoro-pyridin-4-yl)-2,4-dimethoxy-pyrimidine (Prep 66, 725 mg, 3.1 mmol) in MeOH (50 ml) 2N $HCl_{aq}$ (20 ml) was added. After refluxing the mixture for 1 hour, the solvents were evaporated and the crude was tritured with hexane then with iPrOH and finally with DCM to give 550 mg of the title compound (85% yield)

MS (ES) (m/z): 208.2 $[M+H]^+$.

Preparation 68

1-(3,3-Dimethoxy-propyl)-5-(3-fluoro-pyridin-4-yl)-1H-pyrimidine-2,4-dione (Prep68)

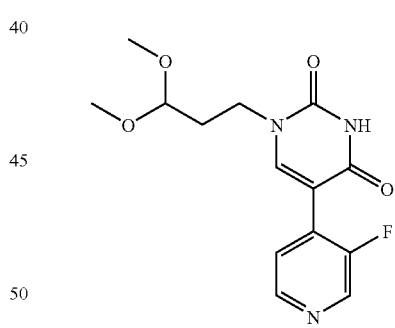

5-(3-Fluoro-pyridin-4-yl)-1H-pyrimidine-2,4-dione hydrochloride (Prep 67, 243 mg, 1.1 mmol) was dissolved in DMF (2 ml). $K_2CO_3$ (153 mg, 1.1 mmol) was added and the mixture was stirred at room temperature for 1 hour. 3-Bromo-1,1dimethoxy-propane (225 mg, 1.11 mmol) was then added and after stirring the reaction at room temperature for 48 hours, the reaction was left at 4° C. for 17 days. Ethyl acetate was then added and the mixture washed with water and brine. The organic phase was dried ($Na_2SO_4$) and evaporated. The residue was purified by flash chromatography with DCM-MeOH—$NH_4OH$ 98-2-0.2 to afford 75 mg of the title compound (22% yield).

MS (ES) (m/z): 310 $[M+H]^+$.

Preparation 69

3-[5-(3-Fluoro-pyridin-4-yl)-2,4-dioxo-3,4-dihydro-2H-pyrimidin-1-yl]-propionaldehyde (Prep69)

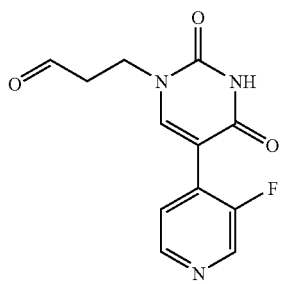

1-(3,3-Dimethoxy-propyl)-5-(3-fluoro-pyridin-4-yl)-1H-pyrimidine-2,4-dione (Prep 68, 75 mg, 0.24 mmol) was dissolved in MeOH (2 ml) and 1N HCl$_{aq}$ (500 µl) was added. The mixture was stirred at room temperature for 16 hours. MeOH was evaporated under vacuum and dioxane was added. After heating the mixture at 60° C. for 6 hours the solvents were evaporated to give the title compound that was used in the next step without further purification (63 mg, quantitative yield).

MS (ES) (m/z): 264 [M+H]$^+$.

Preparation 70

5-(2-Chloro-5-fluoro-pyridin-3-yl)-2,4-dimethoxy-pyrimidine (Prep70)

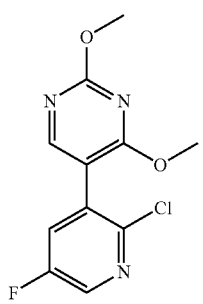

5-Iodo-2,4-dimethoxy-pyrimidine (868 mg, 3.3 mmol) was dissolved in degassed n-PrOH (30 ml) and then 2-chloro-5-fluoropyridine-3-boronic acid (858 mg, 4.9 mmol), Na$_2$CO$_3$ (700 mg, 6.6 mmol), PPh$_3$ (88 mg, 0.33 mmol) and Pd(OAc)$_2$ (90 mg) were added. The suspension was stirred at reflux for 4 hours. The solvent was evaporated under vacuum and the crude was partitioned between brine and ethyl acetate. The organic phase was dried (Na$_2$SO$_4$) and evaporated. The crude was purified by flash chromatography with ethyl acetate-petroleum ether 2-8 affording 240 mg of the title compound (27% yield).

MS (ES) (m/z): 270 [M+H]$^+$.

Preparation 71

5-(2-Chloro-5-fluoro-pyridin-3-yl)-1H-pyrimidine-2,4-dione hydrochloride (Prep71)

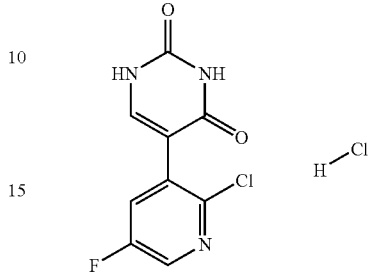

To a solution of 5-(2-chloro-5-fluoro-pyridin-3-yl)-2,4-dimethoxy-pyrimidine (Prep 70, 240 mg, 0.89 mmol) in MeOH (20 ml) 10% HCl$_{aq}$ (15 ml) was added. After refluxing the mixture for 8 hours, the solvents were evaporated and the crude was triturated with ethyl acetate to give 249 mg of the title compound (97% yield)

MS (ES) (m/z): 242 [M+H]$^+$.

Preparation 72

1-(3,3-Dimethoxy-propyl)-5-(2-chloro-5-fluoro-pyridin-3-yl)-1H-pyrimidine-2,4-dione (Prep72)

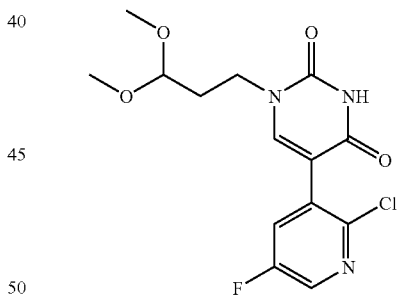

5-(2-Chloro-5-fluoro-pyridin-3-yl)-1H-pyrimidine-2,4-dione hydrochloride (Prep71, 249 mg, 0.9 mmol), K$_2$CO$_3$ (124 mg, 0.9 mmol) and 3-bromo-1,1dimethoxy-propane (205 mg, 1.1 mmol) were suspended in DMF (3 ml). After stirring the reaction at room temperature for 18 hours, water was added. The aqueous layer washed with diethylether and then the product was extracted with ethyl acetate. The organic phase was dried (Na$_2$SO$_4$) and evaporated to give 150 mg of the final compound that was used without further purification in the next step (48% yield).

MS (ES) (m/z): 344 [M+H]$^+$.

Preparation 73

3-[5-(2-Chloro-5-fluoro-pyridin-3-yl)-2,4-dioxo-3,4-dihydro-2H-pyrimidin-1-yl]-propionaldehyde (Prep73)

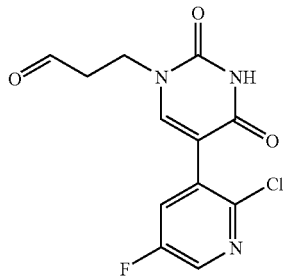

1-(3,3-Dimethoxy-propyl)-5-(2-chloro-5-fluoro-pyridin-3-yl)-1H-pyrimidine-2,4-dione (Prep72, 100 mg, 0.29 mmol) was dissolved in THF (3 ml) and 2N HCl$_{aq}$ (0.5 ml) was added. The solution was stirred at room temperature for 1 hour. THF was evaporated under vacuum and the aqueous residue was lyophilized to give 90 mg of a yellow solid that was used in the next step without further purification (93% yield).

MS (ES) (m/z): 298 [M+H]$^+$.

Preparation 74

5-(6-Fluoro-pyridin-2-yl)-2,4-dimethoxy-pyrimidine (Prep74)

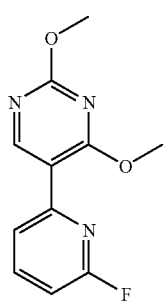

2,4-Dimethoxy-pyrimidine-5-boronic acid (966 mg, 5.3 mmol) was dissolved in degassed n-PrOH (60 ml) and then 2-bromo-6-fluoropyridine (850 mg, 4.8 mmol), Na$_2$CO$_3$ (1.676 g, 15.8 mmol), PPh$_3$ (400 mg, 1.52 mmol) and Pd(OAc)$_2$ (116 mg) were added. The suspension was stirred at reflux for 3 hours. The solvent was evaporated under vacuum and the crude was partitioned between water and ethyl acetate. The organic phase was dried (Na$_2$SO$_4$) and evaporated. The crude was triturated with iPrOH to give 650 mg of the title compound as a white powder (52% yield).

MS (ES) (m/z): 236.2 [M+H]$^+$.

Preparation 75

5-(6-Fluoro-pyridin-2-yl)-1H-pyrimidine-2,4-dione hydrochloride (Prep75)

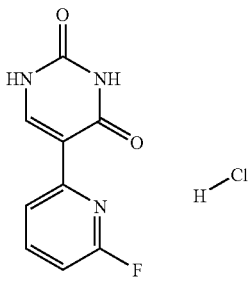

5-(6-Fluoro-pyridin-2-yl)-2,4-dimethoxy-pyrimidine (Prep74, 230 mg, 0.98 mmol) was dissolved in a solution of 4N HCl in dioxane (4 ml). After refluxing the reaction mixture for 1 hour, the solvent was removed under vacuum to give 200 mg of the title compound (84% yield)

MS (ES) (m/z): 208.2 [M+H]$^+$.

Preparation 76

1-(3,3-Dimethoxy-propyl)-5-(6-fluoro-pyridin-2-yl)-1H-pyrimidine-2,4-dione (Prep76)

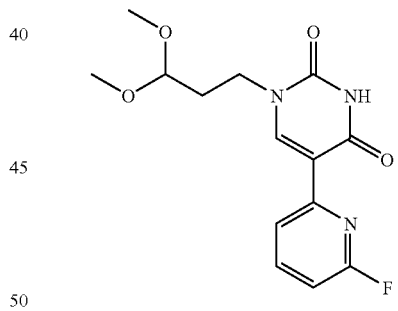

A mixture of 5-(6-Fluoro-pyridin-2-yl)-1H-pyrimidine-2,4-dione hydrochloride (Prep75, 200 mg, 0.82 mmol), and K$_2$CO$_3$ (169 mg, 1.23 mmol) in DMF (4 ml) was stirred 1 hour at room temperature. 3-Bromo-1,1dimethoxy-propane (165 mg, 0.90 mmol) was added and stirring was continued for 48 hours. Water (50 ml) was added and the product was extracted with ethyl acetate. The organic phase was dried (Na$_2$SO$_4$) and evaporated. The crude was triturated with iPr$_2$O to give 179 mg of the final compound as a white solid (70% yield).

MS (ES) (m/z): 310.3 [M+H]$^+$.

Preparation 77

3-[5-(6-Fluoro-pyridin-2-yl)-2,4-dioxo-3,4-dihydro-2H-pyrimidin-1-yl]-propionaldehyde (Prep77)

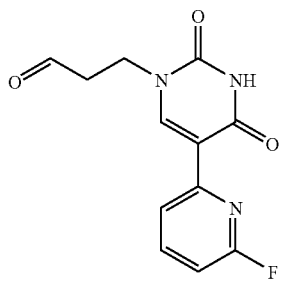

1-(3,3-Dimethoxy-propyl)-5-(6-fluoro-pyridin-2-yl)-1H-pyrimidine-2,4-dione (Prep76, 179 mg, 0.58 mmol) was dissolved in THF (4 ml) and 2N HCl$_{aq}$ (0.5 ml) was added. The solution was then stirred at room temperature for 2 hours. THF was evaporated under vacuum and the aqueous residue was lyophilized to give 170 mg of a yellow powder that was used in the next step without further purification (quantitative yield).

MS (ES) (m/z): 264.2 [M+H]$^+$.

Preparation 78

6-(2,4-Dimethoxy-pyrimidin-5-yl)-pyridine-2-carbonitrile (Prep78)

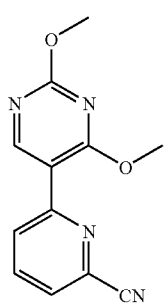

5-Iodo-2,4-dimethoxy-pyrimidine (500 mg, 1.88 mmol) was dissolved in degassed n-PrOH (40 ml) and then 6-cyano-pyridine-2-boronic acid pinacol ester (650 mg, 2.82 mmol), Na$_2$CO$_3$ (598 mg, 5.64 mmol), PPh$_3$ (164 mg, 0.62 mmol) and Pd(OAc)$_2$ (42 mg, 0.19 mmol) were added. The suspension was stirred at reflux for 3 hours. The solvent was evaporated and the crude was partitioned between water and ethyl acetate. The organic phase was dried (Na$_2$SO$_4$) and evaporated. The crude was triturated with iPrOH to give 200 mg of the title compound (44% yield).

MS (ES) (m/z): 243 [M+H]$^+$.

Preparation 79

6-(2,4-Dioxo-1,2,3,4-tetrahydro-pyrimidin-5-yl)-pyridine-2-carbonitrile hydrochloride (Prep79)

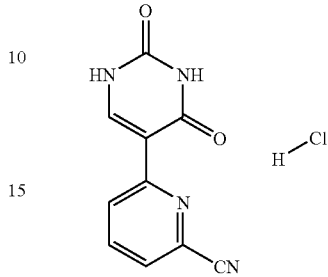

To a solution of 6-(2,4-Dimethoxy-pyrimidin-5-yl)-pyridine-2-carbonitrile (Prep78, 200 mg, 0.82 mmol) in MeOH (30 ml), 10% HCl$_{aq}$ (15 ml) was added. After stirring for 2 hours at reflux, the solvents were evaporated. The crude was triturated with ethyl acetate to give 200 mg of the title compound (97% yield)

MS (ES) (m/z): 215 [M+H]$^+$.

Preparation 80

(1R,5S/1S,5R) 1-{3-[1-(4-chlorophenyl)-3-azabicyclo[3.1.0]hex-3-yl]propyl}-5-iodo-3-(phenylcarbonyl)-2,4(1H,3H)-pyrimidinedione (Prep 80)

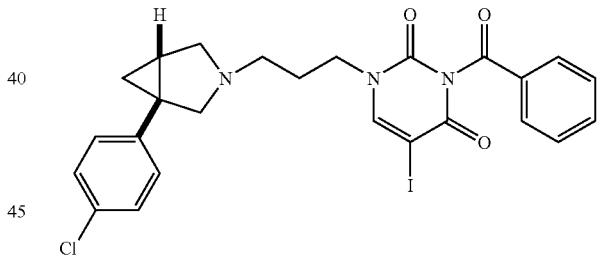

1-(4-chlorophenyl)-3-azabicyclo[3.1.0]hexane (racemate, reference procedure for preparation reported in WO2005/080382, 136 mg, 0.703 mmol), acetic acid (0.060 mL, 1.055 mmol), and sodium triacetoxyborohydride (164 mg, 0.774 mmol) were added at 0° C. to a solution of 3-[5-iodo-2,4-dioxo-3-(phenylcarbonyl)-3,4-dihydro-1(2H)-pyrimidinyl]propanal (P38, 280 mg, 0.703 mmol) in 1,2-Dichloroethane (DCE) (8.7 ml). The mixture was stirred at 0° C. for further 4 hours. Water was added and the reaction mixture was concentrated removing the solvent under vacuum. The residue was re-dissolved in ethyl acetate and the organic layer washed with aqueous saturated NaHCO3 solution. The aqueous solution was extracted with ethyl acetate (3×20 ml). The organic layers were collected, dried over Na$_2$SO$_4$, filtrated and evaporated. The crude was purified by chromatography (SPE Si 10 g) with toluene/acetone 8/2. The title compound was recovered as a light yellow oil (190 mg).

MS (ES) (m/z): 576.2 [M+H]$^+$.

Preparation 81

(1R,5S/1S,5R) 1-{3-[1-(4-chlorophenyl)-3-azabicyclo[3.1.0]hex-3-yl]propyl}-5-iodo-2,4(1H,3H)-pyrimidinedione (Prep81)

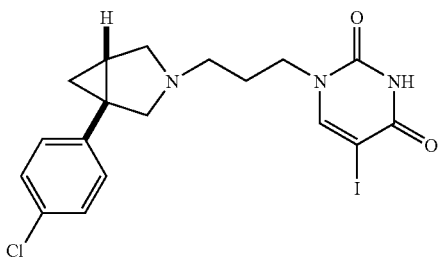

(1R,5S/1S,5R)-(1-{3-[1-(4-chlorophenyl)-3-azabicyclo[3.1.0]hex-3-yl]propyl}-5-iodo-3-(phenylcarbonyl)-2,4(1H,3H)-pyrimidinedione (Prep 80, 190 mg, 0.330 mmol) was dissolved in 3% ammonia in MeOH (4 ml, 5.55 mmol). The mixture was stirred at room temperature for 3 hours the solvent was then evaporated under vacuum and the crude purified by SPE Si cartridge (20 g) eluting with Toluene/acetone 80/20 to give an oil that was then loaded through SCX (5 g) cartridge to recover the title compound (130 mg, 0.276 mmol, 4.97% yield) as a light yellow oil.

MS (ES) (m/z): 472.2 [M+H]+.

$^1$H-NMR (DMSO-d$_6$) δ ppm 11.54 (br. s., 1 H) 8.13 (br. s., 1 H) 7.21-7.48 (m, 2 H) 7.11-7.19 (m, 2 H) 3.67-3.77 (m, 2 H) 3.22-3.33 (m, 2 H) 2.95-3.04 (m, 1 H) 2.27-2.46 (m, 3 H) 1.65-1.85 (m, 3 H) 1.27-1.38 (m, 1 H) 0.68-0.78 (m, 1 H)

Preparation 82

(1R,5S/1S,5R) 5-iodo-3-(phenylcarbonyl)-1-(3-{1-[3-(trifluoromethyl)phenyl]-3-azabicyclo[3.1.0]hex-3-yl}propyl)-2,4(1H,3H)-pyrimidinedione (Prep82)

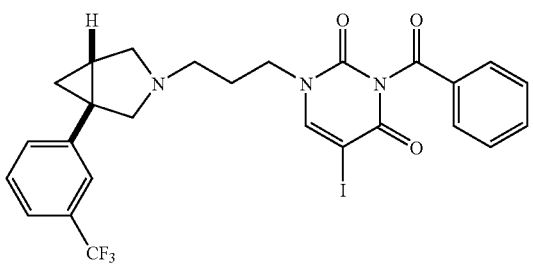

To a solution of 3-[5-iodo-2,4-dioxo-3-(phenylcarbonyl)-3,4-dihydro-1(2H)-pyrimidinyl]propanal (P38, 350 mg, 0.88 mmol) and (1-[3-(trifluoromethyl)phenyl]-3-azabicyclo[3.1.0]hexane (racemate, reference procedure for preparation reported in WO2005/080382, 200 mg, 0.88 mmol) in dry DCE (10 ml), AcOH was added and the reaction mixture cooled to 0° C. Sodiumtriacetoxyborohydride (224 mg, 1.055 mmol) was added and the reaction left at 0° C. for 4 hrs. Reaction monitored by LC/MS. The mixture was diluted with a saturated solution of NaHCO$_3$ and extracted with DCM. The solvent was evaporated and the crude purified by silica SPE column (20 g) eluting with acetone/toluene 20:80. After evaporation, 250 mg of the title compound were obtained.

MS (ES) (m/z): 610.01 [M+H]+.

Preparation 83

(1R,5S/1S,5R) 5-iodo-1-(3-{1-[3-(trifluoromethyl)phenyl]-3-azabicyclo[3.1.0]hex-3-yl}propyl)-2,4(1H,3H)-pyrimidinedione (Prep83)

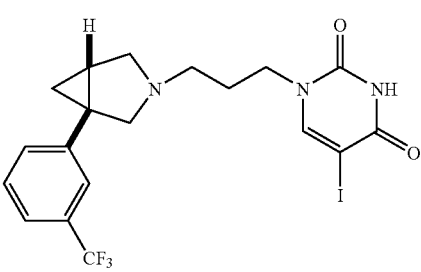

(1R,5S/1S,5R) 5-iodo-3-(phenylcarbonyl)-1-(3-{1-[3-(trifluoromethyl)phenyl]-3-azabicyclo[3.1.0]hex-3-yl}propyl)-2,4(1H,3H)-pyrimidinedione (Prep82, 250 mg, 0.410 mmol) was dissolved in 3% ammonia in MeOH, (4 mL, 5.55 mmol). The mixture was stirred at room temperature for 3 hours, the solvent was then evaporated under vacuum and the crude purified by SPE Si (20 g) with Toluene/acetone 80/20 to give a solid that was then loaded through a SCX (5 g) cartridge in order to recover the title compound (168 mg, 0.332 mmol, 81% yield) as a white solid.

MS (ES) (m/z): 506.2 [M+H]+.

$^1$H-NMR (DMSO-d$_6$) δ ppm 11.61 (br. s., 1 H) 8.07-8.24 (m, 1 H) 7.50-7.55 (m, 2 H) 7.36-7.48 (m, 2 H) 3.66-3.81 (m, 2 H) 3.23-3.40 (m, 2 H) 2.93-3.05 (m, 1 H) 2.26-2.49 (m, 3 H) 1.83-1.97 (m, 1 H) 1.69-1.83 (m, 2 H) 1.35-1.46 (m, 1 H) 0.75-0.88 (m, 1 H)

Preparation 84

1-(3-{(1S,5R)-1-[2-fluoro-4-(trifluoromethyl)phenyl]-3-azabicyclo[3.1.0]hex-3-yl}propyl)-5-iodo-3-(phenylcarbonyl)-2,4(1H,3H)-pyrimidinedione (Prep 84)

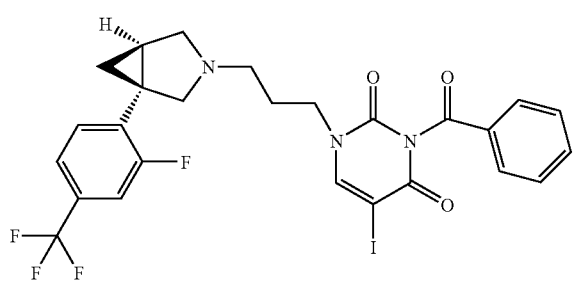

The title compound was prepared using a similar procedure to that set out earlier in Preparation 82, starting from (1S,5R)-1-[2-fluoro-4-(trifluoromethyl)phenyl]-3-azabicyclo[3.1.0]hexane (reference procedure for preparation reported in WO2005/080382, 200 mg, 0.88 mmol).

MS (ES) (m/z): 628 [M+H]+.

$^1$H-NMR (CDCl$_3$) δ ppm 7.90-7.96 (m, 2 H) 7.88-7.91 (m, 1 H) 7.65-7.71 (m, 1 H) 7.48-7.56 (m, 2 H) 7.15-7.40 (m, 3 H)

3.90 (t, 2 H) 3.30 (dd, 1 H) 3.15 (d, 1 H) 2.63 (dd, 1 H) 2.50-2.61 (m, 3 H) 1.82-1.95 (m, 3 H) 1.38-1.44 (m, 1 H) 0.87-0.95 (m, 1 H)

Preparation 85

1-(3-{(1S,5R)-1-[2-fluoro-4-(trifluoromethyl)phenyl]-3-azabicyclo[3.1.0]hex-3-yl}propyl)-5-iodo-2,4(1H,3H)-pyrimidinedione (Prep85)

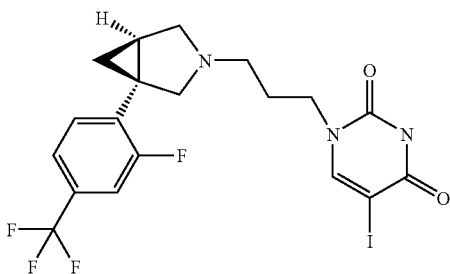

The title compound was prepared using a similar procedure to that set out earlier in Preparation 83, starting from 1-(3-{(1S,5R)-1-[2-fluoro-4-(trifluoromethyl)phenyl]-3-azabicyclo[3.1.0]hex-3-yl}propyl)-5-iodo-3-(phenylcarbonyl)-2,4(1H,3H)-pyrimidinedione (Prep 84).

MS (ES) (m/z): 524 [M+H]$^+$.

$^1$H-NMR (CDCl$_3$) δ ppm 8.37 (br. s., 1 H) 7.72-7.81 (m, 1 H) 7.33-7.39 (m, 2 H) 7.26-7.32 (m, 1 H) 3.85 (t, 2 H) 3.28 (dd, 1 H) 3.12 (d, 1 H) 2.61 (dd, 1 H) 2.48-2.56 (m, 3 H) 1.81-1.91 (m, 3 H) 1.36-1.42 (m, 1 H) 0.90 (dd, 1 H)

Preparation 86

5-bromo-2,4-bis(methyloxy)pyrimidine (Prep86)

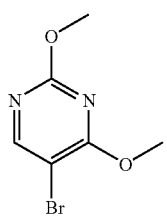

To a solution of 5-bromo-2,4-dichloropyrimidine (5 g, 21.94 mmol) in dry Tetrahydrofuran (THF) (100 ml) cooled at 0° C., sodium methoxide (2.96 g, 54.9 mmol) was added portionwise.

Dry Methanol (8 ml) was added and the slurry was left to reach room temperature and stirred at ambient temperature overnight.

Then NaHCO$_3$ saturated solution (50 mL) was cautiously added and the mixture concentrated under reduced pressure to a small volume. The residual mixture was taken up with water (30 mL) and extracted with DCM (2×100 mL). Combined organics were dried over Na2SO4 and evaporated to dryness, taken up with pentane and re-evaporated to dryness to get the title compound as an off white solid (4 g).

MS (ES) (m/z): 219; 221 [M+H]$^+$.

Preparation 87

5-(2-fluoro-3-pyridinyl)-2,4-bis(methyloxy)pyrimidine (Prep87)

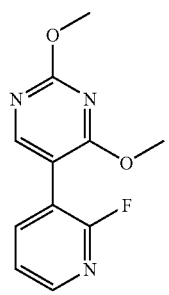

To a mixture of 5-bromo-2,4-bis(methyloxy)pyrimidine (Prep86, 3 g, 13.70 mmol), 2-fluoropyridine-3-boronic acid (1.930 g, 13.70 mmol) and Pd(PPh$_3$)$_4$ (0.791 g, 0.685 mmol), dry 1,4-Dioxane (45 ml) was added followed by potassium carbonate 1M solution (27.4 ml, 27.4 mmol). The mixture was degassed with Argon and then heated at 100° C. for 1 h (internal T~90° C.). Then the mixture was cooled down to ambient, further 1 eq of boronic acid (1.930 g, 13.70 mmol) followed by 5 mol % of PdTetrakis (0.791 g, 0.685 mmol) were added and the mixture heated at 100° C. for two 2 h. The reaction mixture was cooled down to room temperature, taken up with water and AcOEt. The aqueous layer was back extracted with AcOEt. The combined organics were dried over Na$_2$SO$_4$ and evaporated to dryness. The crude material was purified by SiO$_2$ flash chromatography eluting with Cy/EA 8/2 to get the title compound as white solid (3 g).

MS (ES) (m/z): 236.0 [M+H]$^+$.

Preparation 88

5-(2-fluoro-3-pyridinyl)-2,4(1H,3H)-pyrimidinedione hydrochloride (Prep88)

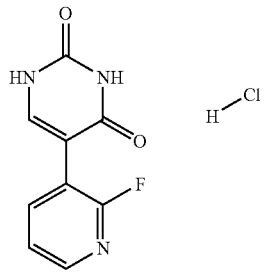

A solution of 5-(2-fluoro-3-pyridinyl)-2,4-bis(methyloxy)pyrimidine (Prep87, 2.8 g, 11.90 mmol) in HCl 4M in 1,4dioxane (42 mL, 168 mmol) was heated at 90° C. for 1 h. A white precipitate crashed out of the solution. Volatiles were evaporated under reduced pressure to give title compound, pale yellow solid (2.75 g).

MS (ES) (m/z): 208 [M+H]$^+$.

Preparation 89

1-[3,3-bis(methyloxy)propyl]-5-(2-fluoro-3-pyridinyl)-2,4(1H,3H)-pyrimidinedione (Prep89)

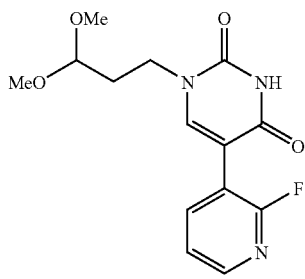

A mixture of 5-(2-fluoro-3-pyridinyl)-2,4(1H,3H)-pyrimidinedione hydrochloride (Prep88, 1 g, 4.10 mmol) and potassium carbonate (0.851 g, 6.16 mmol) in dry N,N-Dimethylformamide (DMF) (20 ml) was stirred 1 h at ambient temperature under an Argon atmosphere.

3Br-1,1-dimethoxy-propane (0.826 g, 4.52 mmol) was added and stirring was continued for 20 h. Water (100 mL) was added and the product was extracted with AcOEt (2×100 mL). The organic phase was dried over $Na_2SO_4$ and evaporated to dryness. Crude material was triturated with IPA (5 vol) to get title compound as white solid (630 mg).

MS (ES) (m/z): 310 [M+H]$^+$.

Preparation 90

5-(6-Chloro-pyridin-3-yl)-2,4-dimethoxy-pyrimidine (Prep90)

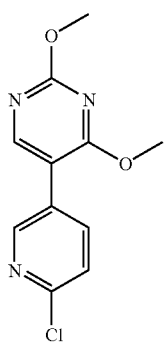

2,4-Dimethoxy-pyrimidine-5-boronic acid (1.14 g, 6.26 mmol) was dissolved in degassed n-PrOH (20 ml) and then 2-chloro-5-iodopyridine (1 g, 4.2 mmol), $Na_2CO_3$ (884 mg, 15.8 mmol), $PPh_3$ (109 mg, 0.42 mmol) and $Pd(OAc)_2$ (46 mg) were added. The suspension was stirred at reflux for 2.5 hours. The solvent was evaporated under vacuum and the crude was partitioned between water and DCM. The organic phase was dried ($Na_2SO_4$) and evaporated to give the title compound that was used in the next step without further purification (quantitative yield).

MS (ES) (m/z): 252.2 [M+H]$^+$.

Preparation 91

5-(6-Chloro-pyridin-3-yl)-1H-pyrimidine-2,4-dione hydrochloride (Prep91)

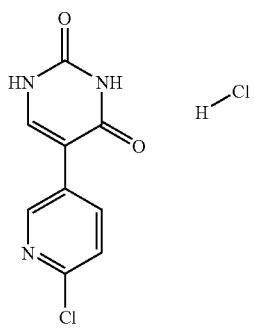

5-(6-Chloro-pyridin-3-yl)-2,4-dimethoxy-pyrimidine (Prep90, 4.17 mmol) was dissolved in MeOH (30 ml) and then 2N $HCl_{aq}$ (10 ml) was added. After refluxing the reaction mixture for 4 hours, the solvent was removed under vacuum to give 1.05 g of the title compound (quantitative yield).

MS (ES) (m/z): 224.1 [M+H]$^+$.

Preparation 92

5-(6-Chloro-pyridin-3-yl)-1-(3,3-dimethoxy-propyl)-1H-pyrimidine-2,4-dione (Prep92)

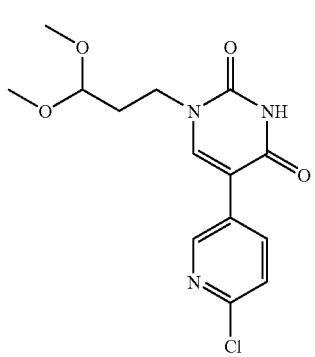

A mixture of 5-(6-chloro-pyridin-3-yl)-1H-pyrimidine-2,4-dione hydrochloride (Prep91, 1.05 g, 4.10 mmol), and $K_2CO_3$ (565 mg, 4.10 mmol) in DMF (20 ml) was stirred 20 minutes at room temperature. 3-Bromo-1,1dimethoxy-propane (635 μl, 4.65 mmol) was added in three portions over 6 days. Solvent was then removed under vacuum at 40° C. and the residue washed once with petroleum ether and twice with ethyl acetate. Ethyl acetate phase was dried ($Na_2SO_4$), filtered and evaporated. The crude was purified by flash chromatography eluting with DCM-MeOH—$NH_4OH$ (98:2:0.2) to give 534 mg of the title compound as a white solid (40% yield).

MS (ES) (m/z): 326.3 [M+H]$^+$.

Preparation 93

3-[5-(6-Chloro-pyridin-3-yl)-2,4-dioxo-3,4-dihydro-2H-pyrimidin-1-yl]-propionaldehyde (Prep93)

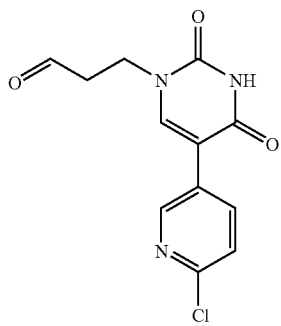

5-(6-Chloro-pyridin-3-yl)-1-(3,3-dimethoxy-propyl)-1H-pyrimidine-2,4-dione (Prep92, 267 mg, 0.82 mmol) was dissolved in THF (10 ml) and then 1N HCl$_{aq}$ (0.82 ml) was added. The solution was stirred at 40° C. for 1.5 hours. TEA (116 µl, 0.83 mmol) was added and the solvent was removed in vacuum at room temperature. Residue was freeze dried to give a white powder that was used in the next step without further purification (quantitative yield).

MS (ES) (m/z): 280.2 [M+H]$^+$.

Preparation 94

5-(2-Chloro-pyridin-3-yl)-2,4-dimethoxy-pyrimidine (Prep94)

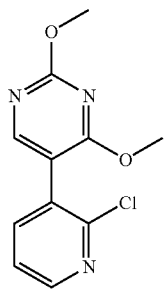

2,4-Dimethoxy-5-iodo-pyrimidine (1 g, 3.76 mmol) was dissolved in degassed n-PrOH (20 ml) and then 2-chloropyridine-3-boronic acid (882 mg, 5.61 mmol), Na$_2$CO$_3$ (800 mg, 7.6 mmol), PPh$_3$ (98 mg, 0.37 mmol) and Pd(OAc)$_2$ (40 mg, 0.19 mmol) were added. The suspension was stirred at reflux for 4 hours. The solvent was evaporated under vacuum and the crude was partitioned between water and DCM. The organic phase was dried (Na$_2$SO$_4$) and evaporated to give the title compound that was used without further purification in the next step (quantitative yield).

MS (ES) (m/z): 252.2 [M+H]$^+$.

Preparation 95

5-(2-Chloro-pyridin-3-yl)-1H-pyrimidine-2,4-dione hydrochloride (Prep95)

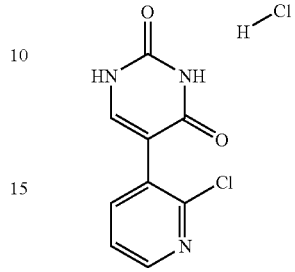

5-(2-Chloro-pyridin-3-yl)-2,4-dimethoxy-pyrimidine (Prep94, 3.76 mmol) was dissolved in MeOH (10 ml), then 2N HCl$_{aq}$ (8 ml) was added. After refluxing the reaction mixture for 4 hours, the solvent was removed under vacuum to give the title compound (quantitative yield)

MS (ES) (m/z): 224.1 [M+H]$^+$.

Preparation 96

5-(2-Chloro-pyridin-3-yl)-1-(3,3-dimethoxy-propyl)-1H-pyrimidine-2,4-dione (Prep96)

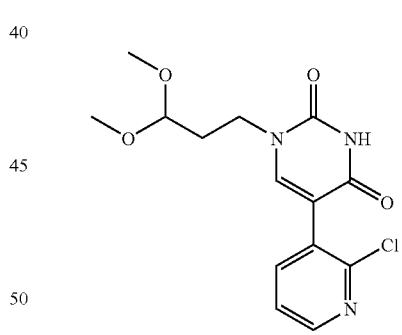

To a suspension of 5-(2-chloro-pyridin-3-yl)-1H-pyrimidine-2,4-dione hydrochloride salt (Prep95, 803 mg, 3.10 mmol) and K$_2$CO$_3$ (428 mg, 3.10 mmol) in DMF (15 ml), 90% 3-bromo-1,1dimethoxy-propane (516 µl, 3.41 mmol) was added in three portions over 5 days. The mixture was contemporarily stirred at room temperature. Solvent was then removed in vacuum at 40° C. The residue washed with petroleum ether and then with ethyl acetate. Ethyl acetate phase was dried (Na$_2$SO$_4$), filtered and evaporated. The crude was purified by flash chromatography eluting with DCM-MeOH—NH$_4$OH (98:2:0.2) to give 400 mg of the final compound as a white solid (40% yield)

MS (ES) (m/z): 326.3 [M+H]$^+$.

Preparation 97

3-[5-(2-Chloro-pyridin-3-yl)-2,4-dioxo-3,4-dihydro-2H-pyrimidin-1-yl]-propionaldehyde (Prep97)

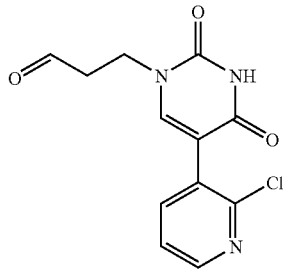

5-(2-Chloro-pyridin-3-yl)-1-(3,3-dimethoxy-propyl)-1H-pyrimidine-2,4-dione (Prep96, 150 mg, 0.46 mmol) was dissolved in THF (5.6 ml) and 1N $HCl_{aq}$ (0.46 ml) was added. The solution was then stirred at 40° C. for 1.5 hours. TEA (0.067 ml, 0.48 mmol) was added and the solvent was carefully removed in vacuum at room temperature. Residue was freeze dried to give a white powder that was used in the next step without further purification (quantitative yield).

MS (ES) (m/z): 280.2 [M+H]$^+$.

Preparation 98

5-(2-Fluoro-5-methylpyridin-3-yl)-2,4-dimethoxy-pyrimidine (Prep98)

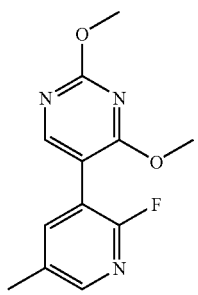

2,4-Dimethoxy-pyrimidine-5-boronic acid (842 mg, 4.60 mmol) was dissolved in degassed n-PrOH (55 ml) and then 2-fluoro-3-bromo-5-methylpyridine (800 mg, 4.21 mmol), $Na_2CO_3$ (1.46 g, 13.77 mmol), $PPh_3$ (348 mg, 1.33 mmol) and $Pd(OAc)_2$ (101 mg, 0.45 mmol) were added. The suspension was stirred at reflux for 2 hours. After cooling, the solvent was evaporated under vacuum and the crude was partitioned between water and ethyl acetate. The organic phase was dried ($Na_2SO_4$) and evaporated. The residue was triturated with $Et_2O$ to give 350 mg of the title compound as a gray powder (31% yield).

MS (ES) (m/z): 250.2 [M+H]$^+$.

Preparation 99

5-(2-Fluoro-5-methyl-pyridin-3-yl)-1H-pyrimidine-2,4-dione hydrochloride (Prep99)

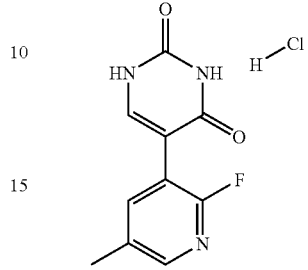

5-(2-Fluoro-5-methylpyridin-3-yl)-2,4-dimethoxy-pyrimidine (Prep98, 350 mg, 1.4 mmol) was dissolved in a solution of 4N HCl in dioxane solution (5 ml). After refluxing the solution for 30 minutes, the solvent was removed under vacuum to give 300 mg of the title compound as a white powder (83% yield).

MS (ES) (m/z): 222.1 [M+H]$^+$.

Preparation 100

5-(2-Fluoro-5-methyl-pyridin-3-yl)-1-(3,3-dimethoxy-propyl)-1H-pyrimidine-2,4-dione (Prep100)

A mixture of 5-(2-fluoro-5-methyl-pyridin-3-yl)-1H-pyrimidine-2,4-dione hydrochloride (Prep99, 300 mg, 1.16 mmol), and $K_2CO_3$ (241 mg, 1.7 mmol) in DMF (5 ml) was stirred for one hour at room temperature. 3-Bromo-1,1dimethoxy-propane (234 mg, 1.3 mmol) was added and stirring was continued for three days. Water was added and the product was extracted with ethyl acetate. The organic phase was dried ($Na_2SO_4$), filtered and evaporated. The crude was purified by flash chromatography eluting with DCM-MeOH—$NH_4OH$ (95:5:0.5) to give 200 mg of the final compound as oil (53% yield).

MS (ES) (m/z): 324.2 [M+H]$^+$.

Preparation 101

3-[5-(2-Fluoro-5-methylpyridin-3-yl)-2,4-dioxo-3,4-dihydro-2H-pyrimidin-1-yl]-propionaldehyde (Prep101)

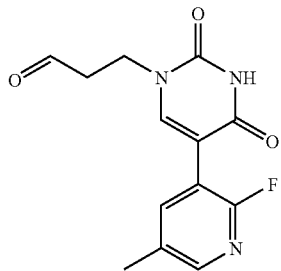

5-(2-Fluoro-5-methyl-pyridin-3-yl)-1-(3,3-dimethoxypropyl)-1H-pyrimidine-2,4-dione (Prep100, 200 mg, 0.62 mmol) was dissolved in THF (5 ml) and 2N $HCl_{aq}$ (1 ml) was added. The solution was stirred at room temperature for 3 hours. The reaction mixture was neutralized with TEA (278 µl, 2 mmol). Water was added and the product extracted with ethyl acetate. The organic phase was dried ($Na_2SO_4$), filtered and evaporated to give 150 mg of a colorless oil (88% yield).

MS (ES) (m/z): 278.2 $[M+H]^+$.

Preparation 102

3-(2,4-Dimethoxy-pyrimidin-5-yl)-pyridine-2-carbonitrile (Prep102)

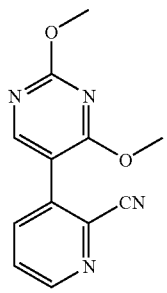

2,4-Dimethoxy-pyrimidine-5-boronic acid (1 g, 5.46 mmol) was dissolved in degassed n-PrOH (30 ml) and then 2-cyano-3-bromopyridine (950 mg, 5.19 mmol), $Na_2CO_3$ (1.65 g, 15.56 mmol), $PPh_3$ (393 mg, 1.5 mmol) and $Pd(OAc)_2$ (114 mg, 0.51 mmol) were added. The suspension was stirred at reflux for 3 hours. After cooling, the solvent was evaporated under vacuum and the crude was partitioned between water and ethyl acetate. The organic phase washed with brine, dried ($Na_2SO_4$) and evaporated. The residue was triturated with iPrOH to give 1 g of the title compound as a white powder (76% yield).

MS (ES) (m/z): 243.2 $[M+H]^+$.

Preparation 103

3-(2,4-Dioxo-1,2,3,4-tetrahydro-pyrimidin-5-yl)-pyridine-2-carbonitrile hydrochloride (Prep103)

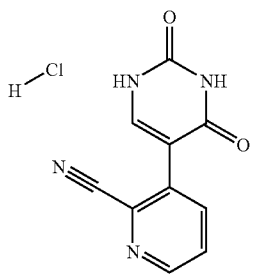

3-(2,4-Dimethoxy-pyrimidin-5-yl)-pyridine-2-carbonitrile (Prep102, 1 g, 4.13 mmol) was dissolved in a solution of 4N HCl in dioxane (20 ml). The mixture was refluxed for 45 minutes. The solvent was removed under vacuum to give 1 g of the title compound (97% yield).

MS (ES) (m/z): 215.1 $[M+H]^+$.

Preparation 104

3-[1-(3,3-Dimethoxy-propyl)-2,4-dioxo-1,2,3,4-tetrahydro-pyrimidin-5-yl]-pyridine-2-carbonitrile (Prep104)

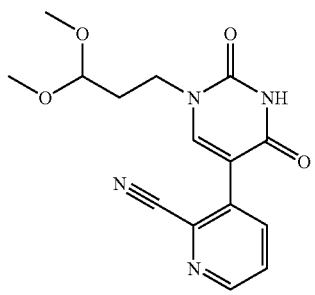

A mixture of 3-(2,4-dioxo-1,2,3,4-tetrahydro-pyrimidin-5-yl)-pyridine-2-carbonitrile hydrochloride (Prep103, 500 mg, 2 mmol), and $K_2CO_3$ (413 mg, 3 mmol) in DMF (7 ml) was stirred for one hour at room temperature. 3-Bromo-1,1dimethoxy-propane (402 mg, 2.2 mmol) was added and stirring continued for 48 hours. Water was added and the product was extracted with ethyl acetate. The organic phase was dried ($Na_2SO_4$) and evaporated to give 210 mg of a yellow oil (33% yield).

MS (ES) (m/z): 317.1 $[M+H]^+$.

Preparation 105

3-[2,4-Dioxo-1-(3-oxo-propyl)-1,2,3,4-tetrahydro-pyrimidin-5-yl]-pyridine-2-carbonitrile (Prep105)

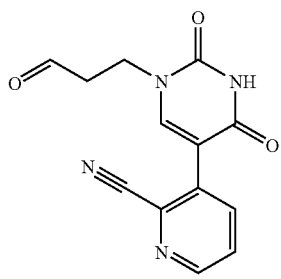

3-[1-(3,3-Dimethoxy-propyl)-2,4-dioxo-1,2,3,4-tetrahydro-pyrimidin-5-yl]-pyridine-2-carbonitrile (Prep104, 210 mg, 0.66 mmol) was dissolved in THF (5 ml) and 2N HCl$_{aq}$ (1 ml) was added. The solution was stirred at room temperature for 2 hours. The reaction mixture was neutralized with TEA. Water was added (1 ml) and the product extracted with ethyl acetate. The organic phase was dried (Na$_2$SO$_4$) and evaporated to give 130 mg of a yellow oil (73% yield)

MS (ES) (m/z): 271.2 [M+H]$^+$.

Preparation 106

5-(2-Chloro-6-methyl-pyridin-3-yl)-2,4-dimethoxy-pyrimidine (Prep106)

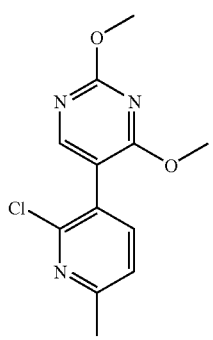

2,4-Dimethoxy-5-iodopyrimidine (957 mg, 3.59 mmol) was dissolved in degassed n-PrOH (18 ml) and then 2-chloro-6-methylpyridine-3-boronic acid (923 mg, 5.39 mmol), Na$_2$CO$_3$ (761 mg, 7.2 mmol), PPh$_3$ (94 mg, 0.35 mmol) and Pd(OAc)$_2$ (40 mg) were added. The suspension was stirred at reflux for 3 hours. The solvent was evaporated under vacuum and the crude was partitioned between water and DCM. The organic phase was dried (Na$_2$SO$_4$) and evaporated to give the title compound that was used without further purification in the next step (quantitative yield).

MS (ES) (m/z): 266.2 [M+H]$^+$.

Preparation 107

5-(2-Chloro-6-methyl-pyridin-3-yl)-1H-pyrimidine-2,4-dione hydrochloride (Prep107)

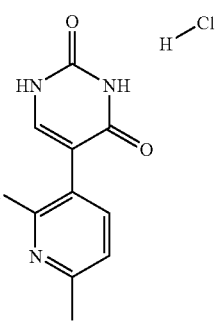

5-(6-Chloro-pyridin-3-yl)-2,4-dimethoxy-pyrimidine (Prep106, 3.59 mmol) was dissolved in MeOH (10 ml); and 2N HCl$_{aq}$ (8 ml) was added. After refluxing the reaction mixture for 4 hours, the solvent was removed under vacuum to give the title compound in quantitative yield.

MS (ES) (m/z): 238.1 [M+H]$^+$.

Preparation 108

5-(2-Chloro-6-methyl-pyridin-3-yl)-1-(3,3-dimethoxy-propyl)-1H-pyrimidine-2,4-dione (Prep108)

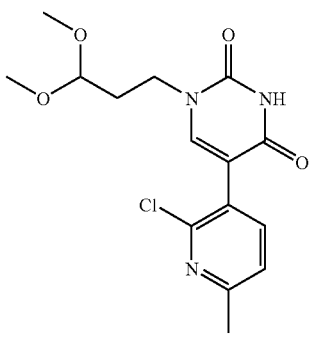

A mixture of 5-(2-Chloro-6-methyl-pyridin-3-yl)-1H-pyrimidine-2,4-dione hydrochloride (Prep107, 345 mg, 1.27 mmol), K$_2$CO$_3$ (174 mg, 1.27 mmol) and 3-bromo-1,1dimethoxy-propane (86 µl, 0.63 mmol) in DMF (3 ml) was stirred at room temperature overnight. 3-Bromo-1,1dimethoxy-propane (86 µl, 0.63 mmol) was then added and the reaction mixture stirred for additional 2 days. Water was added and the aqueous layer washed with diethylether and then the product extracted with ethyl acetate. The organic phase was dried (Na$_2$SO$_4$), filtered and evaporated. The crude was purified by flash chromatography eluting with ethyl acetate-NH$_4$OH (100-0.25) to give 90 mg of the title compound (21% yield).

MS (ES) (m/z): 340.3 [M+H]$^+$.

Preparation 109

3-[5-(2-Chloro-6-methyl-pyridin-3-yl)-2,4-dioxo-3,4-dihydro-2H-pyrimidin-1-yl]-propionaldehyde (Prep109)

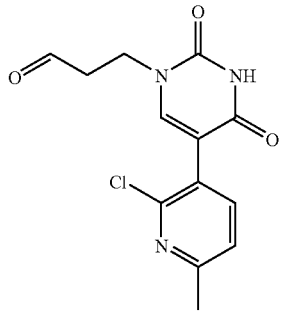

5-(2-Chloro-6-methyl-pyridin-3-yl)-1-(3,3-dimethoxy-propyl)-1H-pyrimidine-2,4-dione (Prep108, 90 mg, 0.26 mmol) was dissolved in THF (4 ml) and 1N $HCl_{aq}$ (265 μl) was added. The solution was then stirred at room temperature for one hour and then warmed at 40° C. for 2.5 hours. TEA (45 μl) was added and the solvent was carefully removed in vacuum at room temperature. Residue was freeze dried to give a white powder that was used in the next step without further purification (quantitative yield).

MS (ES) (m/z): 294.2 $[M+H]^+$.

Preparation 110

5-(4-Methyl-pyridin-3-yl)-2,4-dimethoxy-pyrimidine (Prep10)

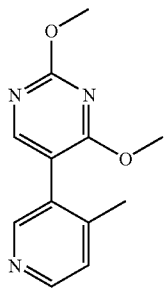

2,4-Dimethoxypyrimidine-5-boronic acid (1.3 g, 7.23 mmol) was dissolved in degassed n-PrOH (20 ml) and then 4-methyl-3-bromo-pyridine (830 g, 4.82 mmol), $Na_2CO_3$ (1.02 g, 9.64 mmol), $PPh_3$ (126 mg, 0.48 mmol) and $Pd(OAc)_2$ (40 mg) were added. The suspension was stirred at reflux for 3 hours. The solvent was evaporated under vacuum and the crude was partitioned between water and DCM. The organic phase was dried ($Na_2SO_4$) and evaporated to give the title compound that was used without further purification in the next step (quantitative yield).

MS (ES) (m/z): 232.2 $[M+H]^+$.

Preparation 111

5-(4-Methyl-pyridin-3-yl)-1H-pyrimidine-2,4-dione hydrochloride (Prep111)

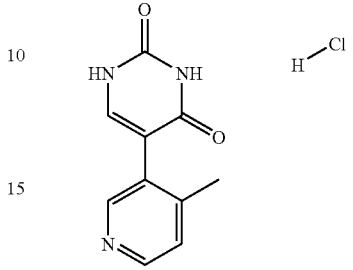

5-(4-Methyl-pyridin-3-yl)-2,4-dimethoxy-pyrimidine (Prep 10, 4.82 mmol) was dissolved in MeOH (10 ml) and then 2N $HCl_{aq}$ (8 ml) was added. After refluxing the reaction mixture for 4 hours, the solvents were removed under vacuum to give the title compound in quantitative yield.

MS (ES) (m/z): 204.1 $[M+H]^+$.

Preparation 112

1-(3,3-Dimethoxy-propyl)-5-(4-methyl-pyridin-3-yl)-1H-pyrimidine-2,4-dione (Prep112)

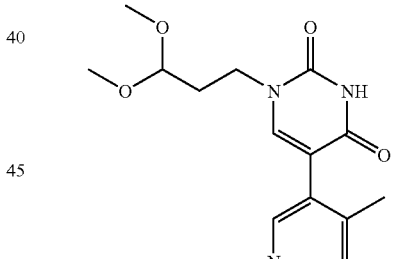

To a mixture of 5-(4-methyl-pyridin-3-yl)-1H-pyrimidine-2,4-dione hydrochloride (Prep 11, 605 mg, 2.53 mmol) and $K_2CO_3$ (349 mg, 2.53 mmol) in DMF (10 ml), 3-bromo-1,1dimethoxy-propane (399 μl, 2.78 mmol) was added in two portions over 2 days and the mixture was contemporarily stirred at room temperature. Water was then added and washed with $Et_2O$, the product was extracted with ethyl acetate. The organic phase was dried ($Na_2SO_4$), filtered and evaporated. The crude was purified by flash chromatography eluting with DCM-MeOH—$NH_4OH$ (98-2-02) to give 100 mg of the title compound (27% yield).

MS (ES) (m/z): 306.3 $[M+H]^+$.

Preparation 113

3-[5-(4-Methyl-pyridin-3-yl)-2,4-dioxo-3,4-dihydro-2H-pyrimidin-1-yl]-propionaldehyde (Prep113)

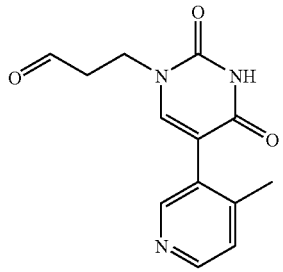

1-(3,3-Dimethoxy-propyl)-5-(4-methyl-pyridin-3-yl)-1H-pyrimidine-2,4-dione (Pre112, 100 mg, 0.32 mmol) was dissolved in THF (5 ml) and 1N HCl$_{aq}$ (327 μl) was added. The solution was then stirred at 40° C. for 1.5 hours. TEA (45 μl) was added and the solvent was carefully removed in vacuum at room temperature. Residue was freeze dried to give the title compound that was used in the next step without further purification (quantitative yield).

MS (ES) (m/z): 260.2 [M+H]$^+$.

Preparation 114

5-(2-Fluoro-6-methyl-pyridin-3-yl)-2,4-dimethoxy-pyrimidine (Prep114)

2,4-Dimethoxy-pyrimidine-5-boronic acid (1.16 g, 6.32 mmol) was dissolved in degassed n-PrOH (22 ml) and then 2-fluoro-6-methyl-3-iodopyridine (870 mg, 3.67 mmol), Na$_2$CO$_3$ (778 mg, 7.34 mmol), PPh$_3$ (96 mg, 0.37 mmol) and Pd(OAc)$_2$ (41 mg added in three portions) were added. The suspension was stirred at reflux for 2.5 hours. The solvent was evaporated under vacuum and the crude was partitioned between water and DCM. The organic phase was dried (Na$_2$SO$_4$) and evaporated. The crude was triturated with iPrOH to give 691 mg of the title compound (75% yield).

MS (ES) (m/z): 250.1 [M+H]$^+$.

Preparation 115

5-(2-Fluoro-6-methyl-pyridin-3-yl)-1H-pyrimidine-2,4-dione hydrochloride (Prep115)

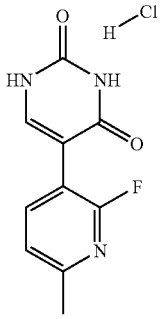

5-(2-Fluoro-6-methyl-pyridin-3-yl)-2,4-dimethoxy-pyrimidine (Prep114, 691 mg, 2.76 mmol) was dissolved in 4M HCl in dioxane solution (7 ml). After refluxing the reaction mixture for 45 minutes, the solvent was removed under vacuum to give 667 mg of the title compound (93% yield)

MS (ES) (m/z): 222.1 [M+H]$^+$.

Preparation 116

1-(3,3-Dimethoxy-propyl)-5-(2-fluoro-6-methyl-pyridin-3-yl)-1H-pyrimidine-2,4-dione (Prep116)

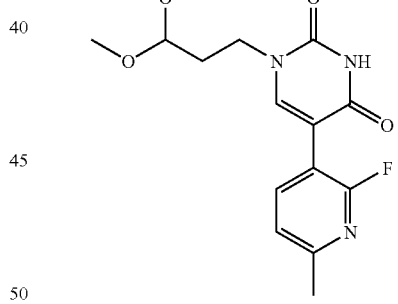

A mixture of 5-(2-fluoro-6-methyl-pyridin-3-yl)-1H-pyrimidine-2,4-dione hydrochloride (Prep 15, 667 mg, 2.59 mmol), and K$_2$CO$_3$ (358 mg, 2.59 mmol) in DMF (25 ml) was stirred 30 minutes at room temperature. Then 90% 3-Bromo-1,1dimethoxy-propane (432 μl, 2.85 mmol) was added in three portions during 3 days. Solvent was then removed under vacuum at 40° C. and the residue washed with ethyl acetate. The organic phase was dried (Na$_2$SO$_4$), filtered and evaporated. The crude was purified by flash chromatography eluting with DCM-MeOH—NH$_4$OH (98-2-0.2) to give 291 mg of the title compound as a white solid (35% yield).

MS (ES) (m/z): 324.3 [M+H]$^+$.

Preparation 117

3-[5-(2-Fluoro-6-methyl-pyridin-3-yl)-2,4-dioxo-3,4-dihydro-2H-pyrimidin-1-yl]-propionaldehyde (Prep117)

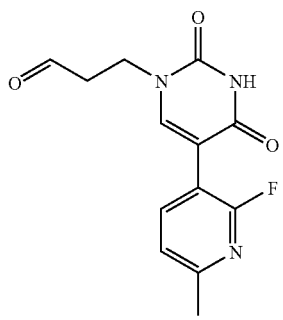

1-(3,3-Dimethoxy-propyl)-5-(2-fluoro-6-methyl-pyridin-3-yl)-1H-pyrimidine-2,4-dione (Prep16, 150 mg, 0.46 mmol) was dissolved in THF (4 ml) and then 1N HCl$_{aq}$ (0.46 ml) was added. The solution was stirred at 40° C. for 1 hour. TEA (65 μl, 0.47 mmol) was added and the solvent was removed in vacuum at room temperature. Residue was freeze dried to give a white powder that was used in the next step without further purification (quantitative yield).

MS (ES) (m/z): 278.2 [M+H]$^+$.

Preparation 118

3-Chloro-pyridazine (Prep118)

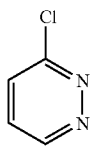

A mixture of pyridazin-3-ol (1.9 g, 19.8 mmol) in POCl$_3$ (19 ml) was heated to 60° C. for 90 minutes. After cooling to room temperature, the reaction was quenched in ice/water and neutralized with solid NaHCO$_3$. The product was extracted with ethyl acetate, the organic phase washed with brine, dried (Na$_2$SO$_4$) and evaporated to give 2.1 g of the title compound as a brown solid (92% yield).

MS (ES) (m/z): 115.1 [M+H]$^+$.

Preparation 119

3-Iodo-pyridazine (Prep119)

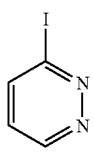

A mixture of 3-chloro-pyridazine (Prep 118, 2.1 g, 18.4 mmol) and NaI, (4 g, 26.8 mmol) in 57% HI$_{aq}$ (16 ml) was warmed at 50° C. for 24 hours. After cooling the solution was basified with solid NaHCO$_3$ and extracted with ethyl acetate. The organic phase was dried (Na$_2$SO$_4$) and evaporated to give 2.1 g of the title compound as a light brown powder (55% yield).

MS (ES) (m/z): 207.2 [M+H]$^+$.

Preparation 120

3-(2,4-Dimethoxy-pyrimidin-5-yl)-pyridazine (Prep120)

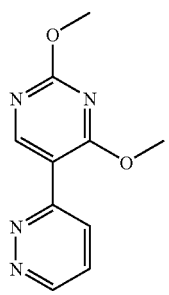

2,4-Dimethoxy-pyrimidine-5-boronic acid (2.05 g, 11.21 mmol) was dissolved in degassed n-PrOH (80 ml) and then 3-iodo-pyridazine (Prep 119, 2.1 g, 10.19 mmol), Na$_2$CO$_3$ (3.24 g, 30.57 mmol), PPh$_3$ (890 mg, 3.40 mmol) and Pd(OAc)$_2$ (180 mg, 0.8 mmol) were added. The suspension was stirred at reflux for 5 hours. The solvent was evaporated under vacuum and the crude was partitioned between water and ethyl acetate. The organic phase washed with brine, dried (Na$_2$SO$_4$) and evaporated. The residue was triturated with iPrOH to afford 750 mg of the title compound as a white powder (34% yield).

MS (ES) (m/z): 219.2 [M+H]$^+$.

Preparation 121

5-Pyridazin-3-yl-1H-pyrimidine-2,4-dione hydrochloride (Prep121)

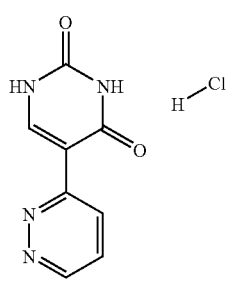

3-(2,4-Dimethoxy-pyrimidin-5-yl)-pyridazine (Prep120, 0.75 g, 3.44 mmol) was dissolved in MeOH (40 ml) and then 10% HCl$_{aq}$ (18 ml) was added. After refluxing the reaction mixture for 30 minutes, the solvent was removed under vacuum and the crude was triturated with MeOH to give 0.6 g of the title compound (77% yield)

MS (ES) (m/z): 191.2 [M+H]$^+$.

Preparation 122

1-(3,3-Dimethoxy-propyl)-5-pyridazin-3-yl-1H-pyrimidine-2,4-dione (Prep122)

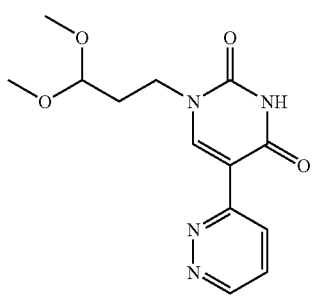

A mixture of 5-pyridazin-3-yl-1H-pyrimidine-2,4-dione hydrochloride (Prep121, 656 mg, 2.89 mmol), 3-bromo-1,1dimethoxy-propane (609 mg, 3.33 mmol) and $K_2CO_3$ (400 mg, 2.89 mmol) in DMSO (10 ml) was stirred for 24 hours at room temperature. 3-Bromo-1, 1dimethoxy-propane (100 mg, 0.55 mmol) was then added and the reaction was left for 11 days at room temperature. 3-Bromo-1,1dimethoxy-propane (100 mg, 0.55 mmol) was further added and stirring continued for additional 6 days. The mixture was lyophilized and the residue washed with diethyl ether and filtrate. The solid washed with ethyl acetate. After evaporation of the organic phase, 200 mg of the title compound as a light brown powder was obtained (24% yield).

MS (ES) (m/z): 293.2 $[M+H]^+$.

Preparation 123

3-(2,4-Dioxo-5-pyridazin-3-yl-3,4-dihydro-2H-pyrimidin-1-yl)-propionaldehyde (Prep123)

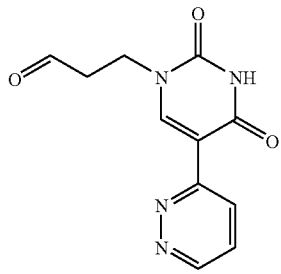

1-(3,3-Dimethoxy-propyl)-5-pyridazin-3-yl-1H-pyrimidine-2,4-dione (Prep122, 200 mg, 0.68 mmol) was dissolved in THF (5 ml) and then 2N $HCl_{aq}$ (1 ml) was added. The solution was stirred at room temperature for 1 hour. The solvent was removed under vacuum at room temperature and the residue was lyophilized to give 185 mg of the title compound as hydrochloride salt (95% yield).

MS (ES) (m/z): 247.2 $[M+H]^+$.

Preparation 124

2,4-Dimethoxy-5-pyrazin-2-yl-pyrimidine (Prep124)

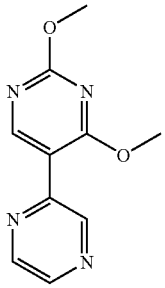

2,4-Dimethoxy-pyrimidine-5-boronic acid (1.33 g, 7.27 mmol) was dissolved in degassed n-PrOH (20 ml) and then 2-iodo-pyrazine (1.0 g, 4.85 mmol), $Na_2CO_3$ (1.02 g, 9.70 mmol), $PPh_3$ (127 mg, 0.48 mmol) and $Pd(OAc)_2$ (54 mg) were added. The suspension was stirred at reflux for 4 hours. The solvent was evaporated under vacuum and the crude was partitioned between water and DCM. The organic phase was dried ($Na_2SO_4$) and evaporated. The crude was purified by flash chromatography eluting with DCM-MeOH—$NH_4OH$ (99-1-0.1) to give 481 mg of the title compound (45% yield).

MS (ES) (m/z): 219.1 $[M+H]^+$.

Preparation 125

5-Pyrazin-2-yl-1H-pyrimidine-2,4-dione hydrochloride (Prep125)

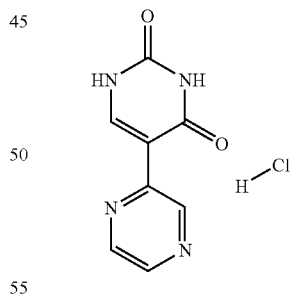

2,4-Dimethoxy-5-pyrazin-2-yl-pyrimidine (Prep124, 481 mg, 2.19 mmol) was dissolved in 4M HCl in dioxane solution (7 ml). After refluxing the reaction mixture for 1 hour, the solvent was removed under vacuum to give the title compound (quantitative yield)

MS (ES) (m/z): 191.1 $[M+H]^+$.

Preparation 126

1-(3,3-Dimethoxy-propyl)-5-pyrazin-2-yl-1H-pyrimidine-2,4-dione (Prep126)

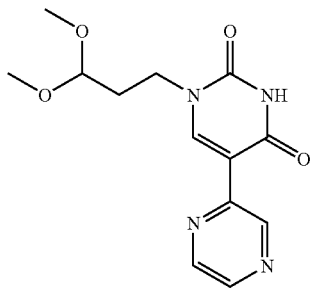

A mixture of 5-pyrazin-2-yl-1H-pyrimidine-2,4-dione hydrochloride (Prep125, 2.19 mmol), and $K_2CO_3$ (302 mg, 2.19 mmol) in DMF (20 ml) was stirred 30 minutes at room temperature. 90% 3-Bromo-1,1dimethoxy-propane (365 µl, 2.41 mmol) was added in two portions during 2 days. Water was added and the mixture was extracted with ethyl acetate. The organic phase was dried ($Na_2SO_4$), filtered and evaporated. The crude was purified by flash chromatography eluting with DCM-MeOH—$NH_4OH$ (98-2-0.2) to give 221 mg of the title compound (35% yield).

MS (ES) (m/z): 293.2 $[M+H]^+$.

Preparation 127

3-(2,4-Dioxo-5-pyrazin-2-yl-3,4-dihydro-2H-pyrimidin-1-yl)-propionaldehyde (Prep127)

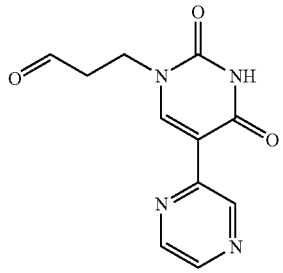

1-(3,3-Dimethoxy-propyl)-5-pyrazin-2-yl-1H-pyrimidine-2,4-dione (Prep126, 111 mg, 0.38 mmol) was dissolved in THF (4 ml) and then 1N $HCl_{aq}$ (0.38 ml) was added. The solution was stirred at 40° C. for 4 hours. TEA (55 µl, 0.39 mmol) was added and the solvent was removed in vacuum at room temperature. Residue was freeze dried to give a white powder that was used in the next step without further purification (quantitative yield).

MS (ES) (m/z): 247.2 $[M+H]^+$.

Preparation 128

3-Benzoyl-5-iodo-1H-pyrimidine-2,4-dione (Prep128)

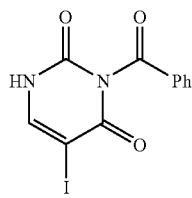

A solution of 5-iodouracil (2 g, 8.4 mmol) in dry pyridine (20 ml) was added dropwise to a solution of benzoyl chloride (3.5 g, 25.3 mmol) in pyridine (10 ml). The mixture was stirred at room temperature for 3 hours. Water (70 ml) was added and extracted with ethyl acetate. The organic phase washed with a saturated solution of $NH_4Cl$ and then with 2% HCl (40 ml×4). The solvent was removed under vacuum and the residue was triturated with i-$Pr_2O$ to give the title compound as a white solid (2.6 g, 90% yield).

MS (ES) (m/z): 342.2 $[M+H]^+$.

Preparation 129

3-Benzoyl-1-(4-chloro-butyl)-5-iodo-1H-pyrimidine-2,4-dione (Prep129)

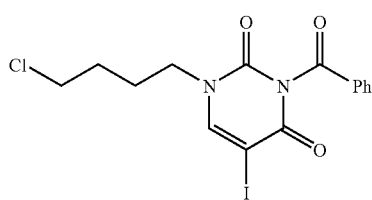

3-Benzoyl-5-iodo-1H-pyrimidine-2,4-dione (Prep128, 2.5 g, 7.3 mmol), $K_2CO_3$ (1 g, 7.3 mmol) and 1-bromo-4-chloro-butane (1.26 ml, 10.95 mmol) were suspended in dry DMF (10 ml). After stirring the reaction at room temperature overnight, further 1-bromo-4-chloro-butane (840 µl, 7.3 mmol) was added. Water was added and the mixture was extracted with ethyl ether. The organic phase was dried ($Na_2SO_4$), filtered and evaporated; the crude was purified by flash chromatography with petroleum ether-ethyl acetate (7-3) to give the title compound as a white solid (3 g, 98% yield).

MS (ES) (m/z): 433.6 $[M+H]^+$. $^1$H-NMR ($CDCl_3$) δ: 7.89-7.93 (m, 2 H), 7.73 (s, 1 H), 7.64-7.70 (m, 1 H), 7.48-7.54 (m, 2 H), 3.84 (t, 2 H), 3.60 (t, 2 H), 1.81-1.98 (m, 4H)

Preparation 130

3-Benzoyl-1-(4-chloro-butyl)-5-(2-fluoro-pyridin-3-yl)-1H-pyrimidine-2,4-dione (Prep130)

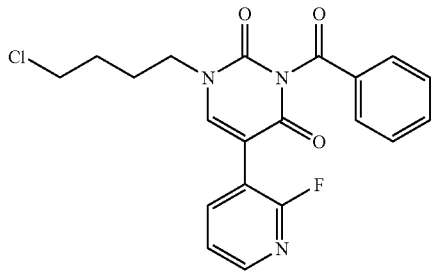

3-Benzoyl-1-(4-chloro-butyl)-5-iodo-1H-pyrimidine-2,4-dione (Prep129, 614 mg, 1.42 mmol) was dissolved in degassed DME-water solution (5-1, 35 ml). 2-Fluoro-pyridine 3-boronic acid (250 mg, 1.77 mmol), Na$_2$CO$_3$ (301 mg, 2.84 mmol), 2-(dicyclohexylphosphino)biphenyl (99 mg, 0.28 mmol) and Pd(PPh$_3$)$_4$ (328 mg, 0.28 mmol) were added and the mixture was refluxed for 3 hours. The solvents were evaporated under vacuum and the crude was partitioned between ethyl acetate and water. The organic phase was dried (Na$_2$SO$_4$) and evaporated; the crude (0.9 g, yellow oil) was purified by flash chromatography with ethyl acetate-petroleum ether (1-1) to give the title compound as yellow oil (310 mg, 54% yield).

MS (ES) (m/z): 402.1 [M+H]$^+$.

Preparation 131

1-(4-Chloro-butyl)-5-(2-fluoro-pyridin-3-yl)-1H-pyrimidine-2,4-dione (Prep131)

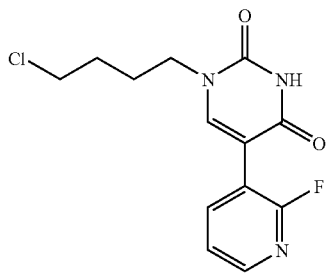

3-Benzoyl-1-(4-chloro-butyl)-5-(2-fluoro-pyridin-3-yl)-1H-pyrimidine-2,4-dione (310 mg, 0.77 mmol) was dissolved in a solution of 3% NH$_3$ in MeOH (10 ml). The mixture was stirred at room temperature for 3 hours, the solvent was then evaporated under vacuum to give 260 mg of a crude that was used without further purification in the next step.

MS (ES) (m/z): 298.2 [M+H]$^+$.

Example 1

1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E1)

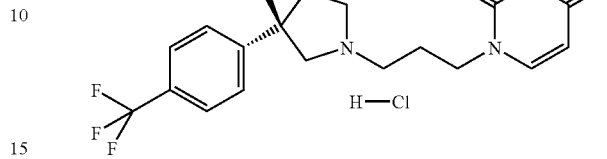

To a solution of 3-(phenylcarbonyl)-1-(3-{(1S,5R)-1-[4-(trifluoromethyl)phenyl]-3-azabicyclo[3.1.0]hex-3-yl}propyl)-2,4(1H,3H)-pyrimidinedione (Prep7, 35 mg) in MeOH (3 mL), ammonium hydroxide (28% in water, 0.75 mL) was added. After 2 hours the reaction mixture was concentrated in vacuo. The crude product was purified by a silica SPE cartridge (1 g) eluting with DCM/MeOH from 100/0 to 98/2 to give 17 mg of the free base of the title compound. To a solution of this material in DCM (1 mL) 0.045 mL of HCl (1M solution in Et$_2$O) were added, the solvent was evaporated in vacuo and the material thus obtained triturated with Et$_2$O to give 15 mg of the title compound as a white slightly hygroscopic solid.

$^1$H NMR (DMSO-d$_6$) (free base of the title compound): δ 11.05 (bs, 1 H), 7.55 (m, 3 H), 7.25 (m, 2 H), 5.49 (m, 1 H), 3.64 (m, 2 H), 3.27 (m, 1 H), 2.97 (m, 2 H), 2.36-2.55 (m, 2 H), 2.32 (m, 1 H), 1.86 (m, 1 H), 1.69 (m, 2 H), 1.37 (m, 1 H), 0.78 (m, 1 H). MS (ES) (m/z): 380 [MH]$^+$.

Example 2

5-methyl-1-(3-{(1S,5R)-1-[4-(trifluoromethyl)phenyl]-3-azabicyclo-[3.1.0]hex-3-yl}propyl)-2,4(1H,3H)-pyrimidinedione hydrochloride (E2)

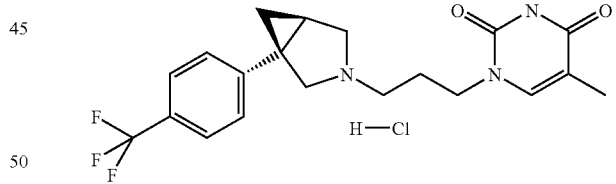

A mixture of 5-methyl-2,4(1H,3H)-pyrimidinedione (thimine, 29 mg) and K$_2$CO$_3$ (32 mg) in dry DMSO (0.45 mL) was stirred for 1 hour at room temperature. A solution of (1S,5R)-3-(3-chloropropyl)-1-[4-(trifluoromethyl)phenyl]-3-azabicyclo[3.1.0]hexane (Prep13, 70 mg) in 0.8 mL of DMSO was then added and the mixture was stirred at 60° C. for 18 hours. Water was then added and the resulting mixture was extracted with EtOAc and DCM. The organic phases were dried over Na$_2$SO$_4$ and concentrated under reduced pressure. The crude product was purified by a silica SPE cartridge (2 g) eluting with dichloromethane/methanol from 100/0 to 98/2, followed by a preparative HPLC (column: Gemini C18, 100×21 mm, 5 um, mobile phase A: NH$_4$HCO$_3$ sol. 10 mM, pH 10, B: acetonitrile, gradient: 35% (B) for 1 min, from 35% (B) to 60% (B) in 9 min, from 60% (B) to

Example 3

5-methyl-1-(4-{(1S,5R)-1-[4-(trifluoromethyl)phenyl]-3-azabicyclo-[3.1.0]hex-3-yl}butyl)-2,4(1H,3H)-pyrimidinedione hydrochloride (E3)

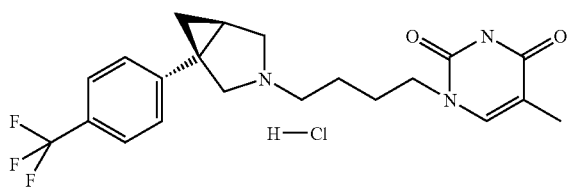

A mixture of (1S,5R)-1-[4-(trifluoromethyl)phenyl]-3-azabicyclo[3.1.0]hexane (Prep4, 70 mg), 1-(4-chlorobutyl)-5-methyl-2,4(1H,3H)-pyrimidinedione (Prep6, 65 mg), $K_2CO_3$ (47 mg) and NaI in DMF (1.5 mL) was heated at 80° C. for 24 hours. Water was then added and the solution was extracted with EtOAc. The organic phase washed with brine, dried over $Na_2SO_4$ and concentrated in vacuo. The crude product was purified by a silica SPE cartridge (2 g) eluting with DCM/MeOH from 100/0 to 98/2, followed by an amino SPE cartridge (1 g) eluting with cyclohexane/EtOAc from 50/50 to 0/100 and a preparative HPLC (column: ABZ plus 20×100 mm, 5 uM, mobile phase A: $H_2O$+0.1% formic acid, mobile phase B: acetonitrile+0.1% formic acid, gradient: from 1 to 20% (B) in 10 min, flow rate: 20 mL/min, UV wavelength range: 210-350 nm, ionization: ES+, mass range: 100-900 amu (ES+)). The product thus obtained was dissolved in DCM and washed with water. The organic phase was dried over $Na_2SO_4$ and concentrated in vacuo to give 5 mg of the free base of the title compound. To a solution of this material in dichloromethane (1 mL) 0.012 mL of HCl (1M solution in $Et_2O$) were added, the solvent was evaporated in vacuo and the material thus obtained triturated with $Et_2O$ to give 7 mg of the title compound as a white slightly hygroscopic solid.

$^1$H-NMR ($CDCl_3$) (free base of the title compound): δ 8.32 (bs, 1 H), 7.58 (d, 2 H), 7.30 (d, 2 H), 7.04 (s, 1 H), 4.01 (s, 1 H), 3.80-3.66 (m, 3 H), 3.15-2.98 (m, 4 H), 2.04 (m, 1H), 1.92 (s, 3H), 1.76 (m, 4H), 1.68 (m, 1 H), 1.12 (m, 2 H). MS (ES) (m/z): 408 [MH]$^+$.

Example 4

5-methyl-1-(4-{(1S,5R/1R,5S)-1-[3-(trifluoromethyl)phenyl]-3-azabicyclo[3.1.0]hex-3-yl}butyl)-2,4 (1H,3H)-pyrimidinedione hydrochloride (E4)

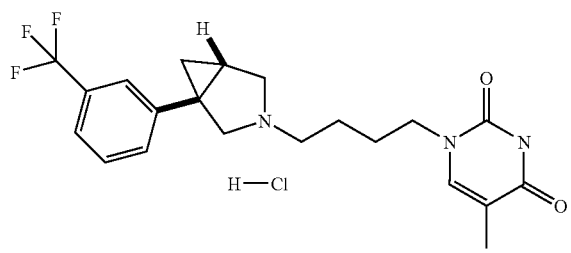

The title compound was prepared with a similar procedure to that set out earlier in Example 1, heating at 90° C. for 5 h, in 23 mg yield as a white slightly hygroscopic solid (y=18%) from (1S,5R/1R,5S)-1-(3-(trifluoromethyl)phenyl)-3-azabicyclo[3.1.0]hexane (reference procedure for preparation reported in WO2005/080382, 40 mg).

$^1$H NMR (DMSO-$d_6$) δ ppm 1.12-1.18 (m, 1 H) 1.49-1.70 (m, 5 H) 1.69-1.73 (m, 3H) 2.22-2.23 (m, 1 H) 3.09-3.21 (m, 2 H) 3.42-3.51 (m, 1 H) 3.51-3.69 (m, 2 H) 3.60 (t, 2H) 3.99 (dd, 1 H) 7.47-7.65 (m, 4 H) 7.53-7.56 (m, 1 H) 10.25 (br. s., 1 H) 11.14-11.24 (m, 1 H). MS (ES) (m/z): 391 [MH]$^+$.

Example 5

1-(4-{(1S,5R)-1-[4-(trifluoromethyl)phenyl]-3-azabicyclo[3.1.0]hex-3-yl}butyl)-2,4(1H,3H)-pyrimidinedione hydrochloride (E5)

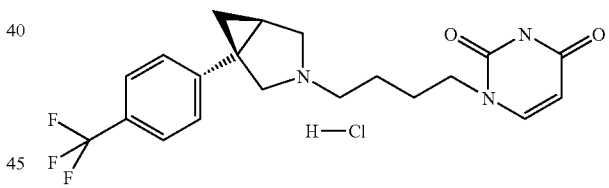

A mixture of (1S,5R)-1-[4-(trifluoromethyl)phenyl]-3-azabicyclo[3.1.0]hexane (Prep4, 80 mg), 1-(4-chlorobutyl)-2,4(1H,3H)-pyrimidinedione (Prep8, 72 mg), TEA (0.098 mL) in DMF (3 mL) was heated at 100° C. for 24 hours. Water was then added and the solution was extracted with EtOAc. The aqueous phase was acidified to pH 7 with aqueous 2% HCl solution and extracted with DCM. The organic phases were washed with brine, dried over $Na_2SO_4$ and concentrated in vacuo. The crude product was purified by a silica SPE cartridge (5 g) eluting with DCM/MeOH from 100/0 to 95/5, followed by an amino SPE column (20 g) eluting with cyclohexane/EtOAc from 50/50 to 0/100 and two preparative HPLC. Conditions of the first HPLC purification: column: ABZ plus 20×100 mm, 5 uM, mobile phase A: $H_2O$+0.1% formic acid, mobile phase B: acetonitrile+0.1% formic acid, gradient: from 1 to 20% (B) in 10 min, flow rate: 20 mL/min, UV wavelength range: 210-350 nm, ionization: ES+, mass range: 100-900 amu (ES+). Conditions of the second HPLC purification: column: Gemini C18, 100×21 mm, 5 um, mobile phase A: $NH_4HCO_3$ sol. 10 mM, pH 10, B: acetonitrile, gradient: 40% (B) for 1 min, from 40% (B) to 75% (B) in 9 min, from 75% (B) to 100% (B) in 1 min, 100% (B) for 4 min, flow rate: 17 mL/min, UV wavelength range: 210-350 nm, ionization: ES+, mass range: 100-900 amu (ES+). The product thus obtained was dissolved in DCM and washed with water. The organic phase was dried over Na$_2$SO$_4$ and concentrated in vacuo to give 20 mg of the free base of the title compound. To a solution of this material in DCM (1 mL) 0.050 mL of HCl (1M solution in Et$_2$O) were added, the solvent was evaporated in vacuo and the material thus obtained triturated with Et$_2$O to give 22 mg of the title compound as a white slightly hygroscopic solid.

$^1$H-NMR (CDCl$_3$) (free base of the title compound): δ 9.22 (bs, 1 H), 7.55 (d, 2 H), 7.25-7.15 (m, 3 H), 5.71 (d, 1H), 3.78 (t, 2 H), 3.38 (d, 1 H), 3.12 (d, 1 H), 2.62-2.44 (m, 4 H), 1.82-1.69 (m, 3H), 1.60-1.44 (m, 3H), 0.85 (m, 1 H). MS (ES) (m/z): 394 [MH]$^+$.

Example 6

5-fluoro-1-(3-{(1S,5R)-1-[4-(trifluoromethyl)phenyl]-3-azabicyclo-[3.1.0]hex-3-yl}propyl)-2,4(1H,3H)-pyrimidinedione hydrochloride (E6)

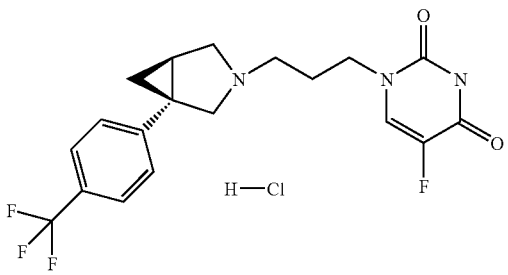

The title compound was prepared with a similar procedure to that set out earlier in Example 6 from (1S,5R)-1-(3-(trifluoromethyl)phenyl)-3-azabicyclo[3.1.0]hexane (Prep10, 18 mg) and 1-(3-chloropropyl)-5-fluoro-2,4(1H,3H)-pyrimidinedione (20 mg) in 12 mg yield as a white slightly hygroscopic solid (y=35%)

$^1$H NMR (DMSO-d$_6$) δ ppm 1.13-1.22 (m, 1 H) 1.58-1.70 (m, 1 H) 1.94-2.10 (m, 2 H) 2.23-2.33 (m, 1 H) 3.09-3.28 (m, 2 H) 3.41-3.54 (m, 1 H) 3.54-3.66 (m, 1 H) 3.65-3.78 (m, 3 H) 3.91-4.11 (m, 1 H) 7.46 (d, 2 H) 7.70 (d, 2 H) 8.10 (d, 1 H) 10.33 (br. s., 1H) 11.67-11.92 (m, 1 H). MS (ES) (m/z): 398[MH]$^+$.

Example 7

5-methyl-1-(5-{(1S,5R)-1-[4-(trifluoromethyl)phenyl]-3-azabicyclo-[3.1.0]hex-3-yl}pentyl)-2,4(1H,3H)-pyrimidinedione hydrochloride (E7)

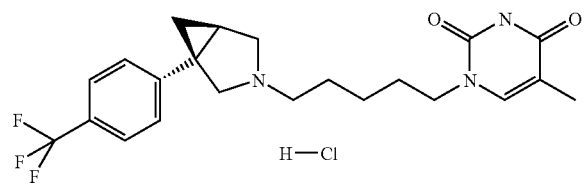

A mixture of (1S,5R)-1-[4-(trifluoromethyl)phenyl]-3-azabicyclo[3.1.0]hexane (41 mg), 1-(4-chloropentyl)-5-methyl-2,4(1H,3H)-pyrimidinedione (Prep11, 50 mg) and TEA (50 μl) in DMF (0.5 mL) was heated at 100° C. overnight. Ammonium chloride was then added and the solution was extracted with dichloromethane. The organic phase was dried and concentrated in vacuo. The crude product was purified by a SCX cartridge followed by a preparative HPLC [column: ABZ plus 20×100 mm, 5 uM, mobile phase A: H$_2$O+0.1% formic acid, mobile phase B: acetonitrile+0.1% formic acid, gradient: from 1 to 20% (B) in 10 min, flow rate: 20 mL/min, UV wavelength range: 210-350 nm, ionization: ES+, mass range: 100-900 amu (ES+)], to give 29 mg of the title compound which was further purified by flash chromatography eluting with DCM/MeOH/NH4OH from 99/1/0.1, to 98/2/0.1, to 97/3/0.1 to give the free base of the title compound (25 mg).

To a solution of this material in DCM (1 mL), HCl (1M solution in Et$_2$O) was added, the solvent was evaporated in vacuo and the material thus obtained triturated with Et$_2$O to give 24 mg of the title compound as a white solid.

$^1$H-NMR (CDCl$_3$): δ 11.23 (m, 1 H), 10.35 (bs, 1 H), 7.69 (d, 2 H), 7.54 (m, 1 H), 7.47 (d, 2H), 4.02 (dd, 1H), 3.68 (dd, 1 H), 3.60 (m, 3 H), 3.47 (m, 1 H), 3.15 (m, 2H), 2.28 (m, 1 H), 1.74 (m, 3H), 1.71 (m, 4 H), 1.58 (m, 1 H), 1.26 (m, 2 H) 1.18 (m, 1 H). MS (ES) (m/z): 421 [MH]$^+$.

Example 8

5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E8)

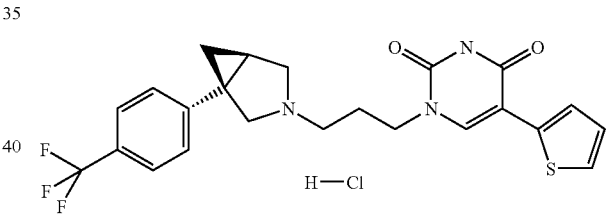

A mixture of (1S,5R)-1-[4-(trifluoromethyl)phenyl]-3-azabicyclo[3.1.0]hexane (Prep4, 40 mg), 1-(3-chloropropyl)-5-(2-thienyl)-2,4(1H,3H)-pyrimidinedione (Prep15, 57 mg), NaI catalytic amount and TEA (0.050 mL) in DMF (0.5 mL) was heated at 100° C. for 24 hours. Aqueous saturated NH$_4$Cl solution was then added to the mixture and then it was extracted with DCM. The organic phases were dried and concentrated in vacuo. The crude product was purified by a SCX cartridge and then by preparative HPLC [(column: XTerra Prep MS C18 30×150 mm, 10 uM; mobile phase A: H2O+0.1% formic acid, mobile phase B: acetonitrile+0.1% formic acid, gradient: from 1 to 25% (B) in 10 min, from 25 to 90% in 4.50 min, from 90 to 100% in 0.50 min; flow rate: 40 mL/min; UV wavelength range: 210-400 nm, ionization: ES+ and ES−; mass range: 150-900 amu (ES+)], to give 52 mg of the title compound as free base. HCl (1M in diethyl ether) was added to a solution of the free base in dichloromethane. The mixture was evaporated and the residue triturated with diethyl ether to give the title compound (40 mg).

$^1$H NMR (DMSO-d$_6$): δ 11.64 (bs, 1H), 10.26 (bs, 1H), 8.41-8.20 (m, 2H), 7.77-7.24 (m, 5H), 7.04 (t, 1H), 4.23-2.86 (m, 9H), 2.42-1.40 (m, 2H), 1.37-0.99 (m, 2H). MS (ES) (m/z): 462 [MH]$^+$.

Example 9

5-phenyl-1-(3-{(1S,5R)-1-[4-(trifluoromethyl)phenyl]-3-azabicyclo-[3.1.0]hex-3-yl}propyl)-2,4(1H,3H)-pyrimidinedione hydrochloride (E9)

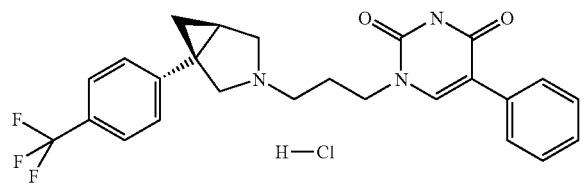

A mixture of (1S,5R)-1-[4-(trifluoromethyl)phenyl]-3-azabicyclo[3.1.0]hexane (Prep4, 40 mg) 1-(3-chloropropyl)-5-phenyl-2,4(1H,3H)-pyrimidinedione (Prep 4, 55 mg), TEA (0.050 mL) and NaI cat. Amount, in DMF (0.5 mL) was heated at 100° C. for 24 hours. Aqueous saturated NH$_4$Cl solution was then added to the mixture and then it was extracted with DCM. The organic phase was dried and concentrated in vacuo. The crude product was purified by a SCX cartridge to give 77 mg of the title compound as free base. HCl (1M in diethyl ether) was added to a solution of the free base in dichloromethane. The mixture was evaporated and the residue triturated with diethyl ether to give the title compound (78 mg).

$^1$H-NMR (CDCl$_3$) δ 11.52 (s, 1H), 10.47 (bs, 1H), 7.96 (s, 1H), 7.68 (d, 2H), 7.58 (d, 2H), 7.48 (d, 2H), 7.38 (t, 2H), 7.29 (t, 1H) 4.03 (dd, 1H), 3.84 (m, 2H), 3.71 (dd, 1H), 3.60 (t, 1H), 3.48 (m, 1H), 3.23 (m, 2H), 2.28 (m, 1H), 2.11 (m, 2H), 1.68 (t, 1H), 1.18 (t, 1H).

MS (ES) (m/z): 456 [MH]$^+$.

Example 10

5-(1-pyrrolidinyl)-1-(3-{(1S,5R)-1-[4-(trifluoromethyl)phenyl]-3-aza-bicyclo[3.1.0]hex-3-yl}propyl)-2,4(1H,3H)-pyrimidinedione hydrochloride (E10)

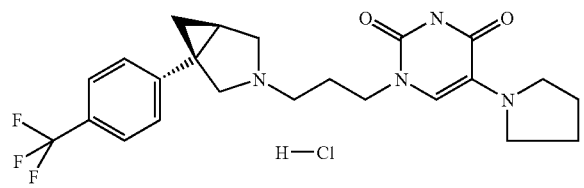

A mixture of (1S,5R)-1-[4-(trifluoromethyl)phenyl]-3-azabicyclo[3.1.0]hexane (Prep4, 11 mg, prepared following a similar procedure to that reported in WO 2005080382), 5-(1-pyrrolidinyl)-2,4(1H,3H)-pyrimidinedione (Prep17, 15 mg) and TEA (0.014 mL) in DMF (0.5 mL) was heated at 100° C. for 24 hours. Water was then added and the solution was extracted with dichloromethane. The organic phase was dried over Na$_2$SO$_4$ and concentrated in vacuo. The crude obtained was loaded over a SCX cartridge and eluted with ammonia (1M in methanol). The resulting product was further purified by preparative HPLC (column: XTerra Prep MS C18 30×150 mm, 10 uM; mobile phase A: H$_2$O+0.1% formic acid, mobile phase B: acetonitrile+0.1% formic acid, gradient: from 1 to 25% (B) in 10 min, from 25 to 90% in 4.50 min, from 90 to 100% in 0.50 min; flow rate: 40 mL/min; UV wavelength range: 210-400 nm, ionization: ES+ and ES−; mass range: 150-900 amu (ES+)). To a solution of the product recovered from the preparative HPLC (5 mg) in dichloromethane (1 mL) HCl (1M in Et$_{2O}$, 1 eq) was added, the solvent was evaporated in vacuo and the material thus obtained triturated with Et$_2$O to give 3 mg of the title compound as a white slightly hygroscopic solid.

$^1$H-NMR (CDCl$_3$) (formiate of the title compound): δ 8.20 (bs, 1H), 7.59 (d, 2H), 7.28 (d, 2H), 6.38 (s, 1H), 3.81 (m, 3H), 3.60 (m, 1H), 2.95-3.05 (m, 4H), 2.14 (m, 1H), 1.91-1.97 (m, 5H), 1.75 (m, 1H), 1.09 (m, 1H). MS (ES) (m/z): 394 [MH]$^+$.

Example 11

5-cyclopropyl-1-(3-{(1S,5R)-1-[4-(trifluoromethyl)phenyl]-3-azabicyclo-[3.1.0]hex-3-yl}propyl)-2,4(1H,3H)-pyrimidinedione hydrochloride (E11)

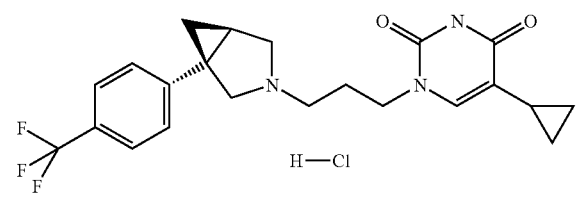

A mixture of (1S,5R)-1-[4-(trifluoromethyl)phenyl]-3-azabicyclo[3.1.0]hexane (Prep4, 35 mg, prepared following a similar procedure to that reported in WO 2005080382), 1-(3-chloropropyl)-5-cyclopropyl-2,4(1H,3H)-pyrimidinedione (Prep16, 46 mg) and TEA (0.042 mL) in DMF (0.5 mL) was heated at 100° C. for 24 hours. Water was then added and the solution was extracted with dichloromethane. The organic phase was dried over Na$_2$SO$_4$ and concentrated in vacuo. The crude product was purified by preparative HPLC (column: XTerra Prep MS C18 30×150 mm, 10 uM; mobile phase A: H$_2$O+0.1% formic acid, mobile phase B: acetonitrile+0.1% formic acid, gradient: from 1 to 25% (B) in 10 min, from 25 to 90% in 4.50 min, from 90 to 100% in 0.50 min; flow rate: 40 mL/min; UV wavelength range: 210-400 nm, ionization: ES+ and ES−; mass range: 150-900 amu (ES+)). The product thus obtained was loaded over a SCX cartridge and eluted with methanol to give 54 mg of the formiate of the title compound. To a solution of this material in dichloromethane (1 mL) HCl (1M in Et$_{2O}$, 1 eq) was added, the solvent was evaporated in vacuo and the material thus obtained triturated with Et$_2$O to give 41 mg of the title compound as a white slightly hygroscopic solid.

$^1$H NMR (DMSO-d$_6$) δ ppm 11.28-11.29 (m, 1H) 10.34 (br. s., 1H) 7.69 (d, 2H) 7.47 (d, 2H) 7.31-7.34 (m, 1H) 4.03 (dd, 1H) 3.65-3.73 (m, 3H) 3.56-3.63 (m, 1H) 3.47-3.47 (m, 1H) 3.13-3.22 (m, 2H) 2.23-2.31 (m, 1H) 1.96-2.07 (m, 2H) 1.62-1.68 (m, 1H) 1.52-1.60 (m, 1H) 1.15-1.21 (m, 1H) 0.65-0.74 (m, 2H) 0.50-0.56 (m, 2H). MS (ES) (m/z): 420 [MH]$^+$.

Example 12

1-(3-{(1S,5R)-1-[2-fluoro-4-(trifluoromethyl)phenyl]-3-azabicyclo[3.1.0]hex-3-yl}propyl)-5-(2-thienyl)-2,4(1H,3H)-pyrimidinedione hydrochloride (E12)

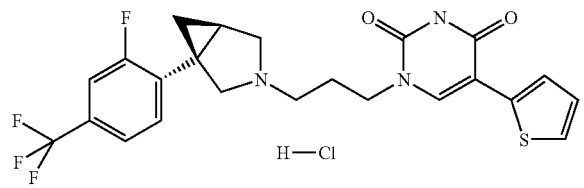

A mixture of (1S,5R)-1-[2-fluoro-4-(trifluoromethyl)phenyl]-3-azabicyclo[3.1.0]hexane (29 mg, prepared following a similar procedure to that reported in WO 2005080382), 1-(3-chloropropyl)-5-(2-thienyl)-2,4(1H,3H)-pyrimidinedione (Prep15, 35 mg) and TEA (0.034 mL) in DMF (1.5 mL) was heated at 100° C. for 24 hours. Water was then added and the solution was extracted with dichloromethane. The organic phase was dried over $Na_2SO_4$ and concentrated in vacuo. The crude obtained was loaded over a SCX cartridge and eluted with ammonia (1M in methanol). The resulting product was further purified by silica flash chromatography (DCM/MeOH 98:2) to obtain 13 mg of the title compound as free base. To a solution of this product (13 mg) in dichloromethane (0.5 mL), HCl (1M in $Et_2O$, 1 eq) was added, the solvent was evaporated in vacuo and the material thus obtained triturated with $Et_2O$ to give 13 mg of the title compound as a yellow solid.

$^1$H-NMR (CDCl$_3$) (formic acid of the title compound): δ 8.20 (bs, 1 H), 7.59 (d, 2 H), 7.28 (d, 2 H), 6.38 (s, 1H), 3.81 (m, 3 H), 3.60 (m, 1H), 2.95-3.05 (m, 4 H), 2.14 (m, 1 H), 1.91-1.97 (m, 5H), 1.75 (m, 1H), 1.09 (m, 1 H). MS (ES) (m/z): 394 [MH]$^+$.

Example 13

5-(trifluoromethyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E13)

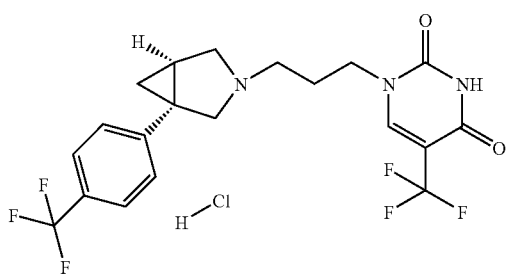

To a solution of 3-(5-trifluoromethyl-2,4-dioxo-3,4-dihydro-2H-pyrimidin-1-yl)-propionaldehyde (Prep21, 0.05 g, 0.21 mmol) in DCE (1 mL), (1S,5R)-1-(4-trifluoromethyl-phenyl)-3-aza-bicyclo[3.1.0]hexane (Prep4, 0.08 g, 0.35 mmol) in DCE (1 mL), AcOH (20 μl, 0.36 mmol) and NaBH(AcO)$_3$ (0.09 g, 0.42) were added and the mixture was stirred at room temperature overnight. Ethyl acetate was added and the solution washed with aqueous saturated NaHCO$_3$. The organic phase was dried (Na$_2$SO$_4$) and evaporated. The crude was purified by flash chromatography with DCM-MeOH—NH$_4$OH (97-3-1) to give the title compound (0.04 mg, 51% yield) as a free base.

5-(trifluoromethyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with a solution of 4N HCl in dioxane (200 μl) to give the title compound as a white solid. The salt was further purified by crystallization with IPA/DIPE to give after filtration 26 mg of title compound.

MS (ES) (m/z): 448.1 [M+H]$^+$. $^1$H-NMR (DMSO-d$_6$, TFA) δ: 11.85 (s, 1 H), 10.31 (br. s., 1 H), 8.41 (s, 1 H), 7.66-7.74 (m, 2 H), 7.46-7.54 (m, 2 H), 4.05 (d, 1 H), 3.84 (dd, 2 H), 3.46-3.76 (m, 3 H), 3.13-3.33 (m, 2 H), 2.29 (ddd, 1 H), 1.97-2.18 (m, 2 H), 1.55-1.69 (m, 1 H), 1.14-1.27 (m, 1H).

Example 14

5-(trifluoromethyl)-1-(4-{(1S,5R)-1-[4-(trifluoromethyl)phenyl]-3-azabicyclo[3.1.0]hex-3-yl}butyl)-2,4 (1H,3H)-pyrimidinedione hydrochloride (E14)

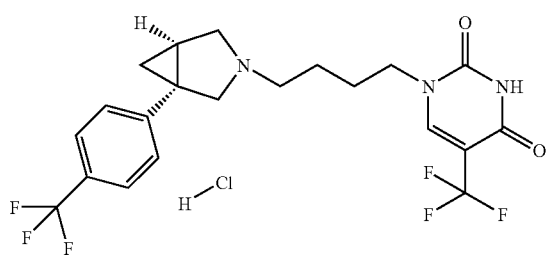

To a solution of 4-(5-trifluoromethyl-2,4-dioxo-3,4-dihydro-2H-pyrimidin-1-yl)-butyraldehyde (Prep24, 22 mg, 0.09 mmol) in dichloroethane (1 mL), (1S,5R)-1-(4-trifluoromethyl-phenyl)-3-aza-bicyclo[3.1.0]hexane (Prep4, 204 mg, 0.09 mmol), AcOH (7.9 mg, 0.13 mmol) and NaBH(AcO)$_3$ (22 mg, 0.18) were added and the mixture was stirred at room temperature overnight. Ethyl acetate was added and the solution was washed with aqueous saturated NaHCO$_3$. The organic phase was dried (Na$_2$SO$_4$) and evaporated. The crude was purified by flash chromatography with DCM-MeOH—NH$_4$OH (95-5-1) to give the title compound (31 mg, 76% yield) as a free base.

5-(trifluoromethyl)-1-(4-{(1S,5R)-1-[4-(trifluoromethyl)phenyl]-3-azabicyclo[3.1.0]hex-3-yl}butyl)-2,4(1H,3H)-pyrimidinedione was treated with a solution of 4N HCl in dioxane (200 μl) to give the title compound as a yellow solid.

MS (ES) (m/z): 462.2 [M+H]$^+$. $^1$H-NMR (DMSO-d$_6$, TFA) δ: 11.80 (s, 1 H), 10.43 (br. s., 1 H), 8.41 (s, 1 H), 7.67-7.77 (m, 2 H), 7.45-7.55 (m, 2 H), 4.04 (dd, 1 H), 3.67-3.81 (m, 3 H), 3.58-3.66 (m, 1 H), 3.45-3.55 (m, 1 H), 3.10-3.31 (m, 2 H), 2.29 (dt, 1 H), 1.59-1.77 (m, 5 H), 1.13-1.30 (m, 1 H)

Example 15

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E15)

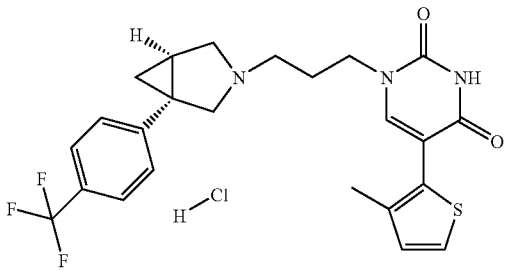

To a solution of 3-[5-(3-methyl-thiophen-2-yl)-2,4-dioxo-3,4-dihydro-2H-pyrimidin-1-yl]-propionaldehyde (Prep29, 16 mg, 0.04 mmol) in DCE (3 mL), (1S,5R)-1-(4-trifluoromethyl-phenyl)-3-aza-bicyclo[3.1.0]hexane (Prep4, 20 mg, 0.05 mmol) in DCE (1 mL), AcOH (6 µl, 0.05 mmol) and NaBH(AcO)$_3$ (30 mg, 0.08 mmol) were added and the mixture was stirred at room temperature overnight. Diethylether was then added and the mixture was washed with 1N solution of HCl, then with aqueous saturated NaHCO$_3$. The organic phase was dried (Na$_2$SO$_4$) and evaporated. The crude was purified by flash chromatography with DCM-MeOH—NH$_4$OH (97-3-1) to give the title compound (8 mg, 42% yield) as a free base.

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with a solution of 4N HCl in dioxane (200 µl) to give the title compound as a white solid.

MS (ES) (m/z): 476.05 [M+H]$^+$. $^1$H-NMR (DMSO-d$_6$) δ: 7.48-7.68 (m, 4 H), 7.32-7.40 (m, 2 H), 7.30 (d, 1 H), 6.88 (d, 1H), 3.79 (t, 2 H), 3.34 (d, 1 H), 3.06 (d, 1 H), 2.54-2.63 (m, 3 H), 2.18 (s, 3 H), 1.80-1.90 (m, 3 H), 1.36-1.45 (m, 1 H), 0.84 (dd, 1 H)

Example 16

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride (E16)

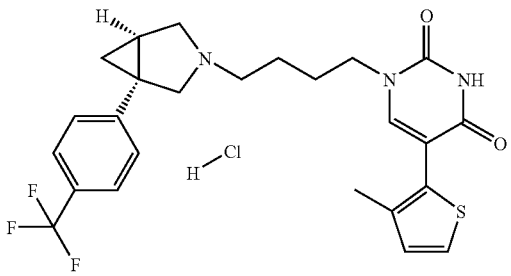

To a solution of 4-[5-(3-methyl-thiophen-2-yl)-2,4-dioxo-3,4-dihydro-2H-pyrimidin-1-yl]-butyraldehyde (Prep32, 30 mg, 0.11 mmol), (1S,5R)-1-(4-trifluoromethyl-phenyl)-3-aza-bicyclo[3.1.0]hexane (Prep4, 21 mg, 0.09 mmol), AcOH (6 µl, 0.1 mmol) in dichloroethane (1.5 mL) and NaBH(AcO)$_3$ (24 mg, 0.11 mmol) were added at 0° C. The reaction was stirred for 30 minutes at room temperature then 2N NaOH (1 mL) was added and the product extracted with ethyl acetate. The organic phase washed with brine, dried (Na$_2$SO$_4$) and evaporated. The crude was purified by flash chromatography with DCM-MeOH—NH$_4$OH (95-5-0.5) to give the title compound (26 mg, 48% yield) as a free base.

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione was treated with a solution of 4N HCl in dioxane (200 µl) to give the title compound as a white solid.

MS (ES) (m/z): 490.02 [M+H]$^+$. $^1$H-NMR (DMSO-d$_6$) δ: 11.52 (s, 1 H), 10.56 (br. s., 1 H), 7.85 (s, 1 H), 7.64-7.75 (m, 2 H), 7.45-7.52 (m, 2 H), 7.42 (d, 1 H), 6.93 (d, 1 H), 3.98-4.07 (m, 1 H), 3.57-3.84 (m, 4 H), 3.44-3.55 (m, 1 H), 3.09-3.28 (m, 2 H), 2.25-2.32 (m, 1 H), 2.17 (s, 3 H), 1.54-1.82 (m, 5 H), 1.14-1.28 (m, 1 H)

Example 17

2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinecarbonitrile hydrochloride (E17)

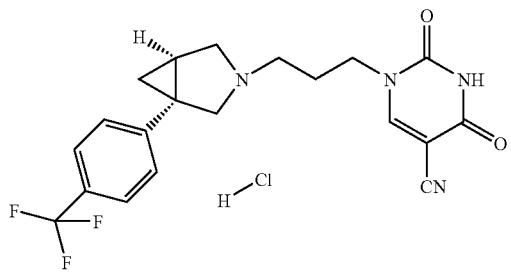

To a solution of 2,4-dioxo-1-(3-oxo-propyl)-1,2,3,4-tetrahydro-pyrimidine-5-carbonitrile (Prep35, 90 mg, 0.47 mmol) in dichloroethane (8 mL), (1S,5R)-1-(4-trifluoromethyl-phenyl)-3-aza-bicyclo[3.1.0]hexane (Prep4, 106 mg, 0.47 mmol), AcOH (42 mg, 0.7 mmol) and NaBH(AcO)$_3$ (198 mg, 0.94 mmol) were added and the mixture was stirred at room temperature overnight. The solvent was evaporated under vacuum, the residue redissolved in ethyl acetate and the obtained mixture washed with aqueous saturated NaHCO$_3$ solution. The organic phase was dried (Na$_2$SO$_4$) and evaporated. The crude was purified by flash chromatography with DCM-MeOH—NH$_4$OH (97-3-1) to give the free base of the title compound as a white solid (70 mg, 38% yield).

The compound obtained was further purified on silica flash isolute column with DCM/MeOH/NH3 9:1:1% and then 2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinecarbonitrile was treated with a solution of 4N HCl in dioxane (200 µl) to give the corresponding hydrochloride salt. The salt was then resuspended in AcOEt and washed with a 5% solution of NaHCO3. After evaporation of the solvent, the free base was treated with a solution of 4N HCl in dioxane to give the title compound as a pale yellow solid. (31 mg)

MS (ES) (m/z): 405.24 [M+H]$^+$. $^1$H-NMR (DMSO-d$_6$) δ: 12.01 (s, 1 H), 10.66 (br. s., 1 H), 8.71 (s, 1 H), 7.66-7.75 (m, 2 H), 7.45-7.55 (m, 2 H), 4.04 (dd, 1 H), 3.83 (t, 2 H), 3.56-3.75 (m, 2 H), 3.40-3.53 (m, 1 H), 3.14-3.26 (m, 2 H), 2.24-2.35 (m, 1 H), 1.96-2.18 (m, 2 H), 1.75 (dd, 1 H), 1.19 (dd, 1H)

Example 18

2,4-dioxo-1-(4-{(1S,5R)-1-[4-(trifluoromethyl)phenyl]-3-azabicyclo[3.1.0]hex-3-yl}butyl)-1,2,3,4-tetrahydro-5-pyrimidinecarbonitrile hydrochloride (E18)

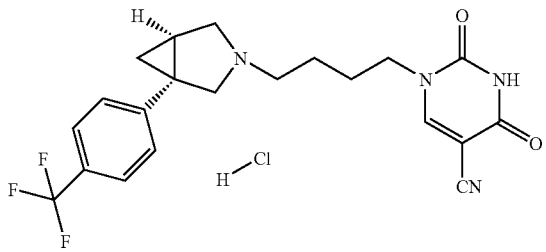

To a solution of 2,4-dioxo-1-(4-oxo-butyl)-1,2,3,4-tetrahydro-pyrimidine-5-carbonitrile (Prep55, 70 mg, 0.34 mmol) in dichloroethane (5 mL), (1S,5R)-1-(4-trifluoromethyl-phenyl)-3-aza-bicyclo[3.1.0]hexane (Prep4, 76 mg, 0.34 mmol) was added. The suspension was cooled at 0° C. and then AcOH (30 mg, 0.68 mmol) and NaBH(AcO)$_3$ (79 mg, 0.38 mmol) were added and the mixture stirred at 0° C. for 4 hours. Water was added and the solvent was evaporated under vacuum, the residue re-dissolved in ethyl acetate and the mixture washed with aqueous saturated NaHCO$_3$ solution. The organic phase was dried (Na$_2$SO$_4$) and evaporated. The crude was purified by flash chromatography with DCM-MeOH—NH$_4$OH (97-3-1) to give the title compound as a white solid (86 mg, 53% yield) as free base 2,4-dioxo-1-(4-{(1S,5R)-1-[4-(trifluoromethyl)phenyl]-3-azabicyclo[3.1.0]hex-3-yl}butyl)-1,2,3,4-tetrahydro-5-pyrimidinecarbonitrile was treated with a solution of 4N HCl in dioxane (200 μl) to give the title compound as a pale yellow solid. (76 mg).

MS (ES) (m/z): 419.2 [M+H]$^+$. $^1$H-NMR (DMSO-d$_6$) δ: 11.97 (s, 1 H), 10.99 (br. s., 1 H), 8.74 (s, 1 H), 7.61-7.72 (m, 2 H), 7.43-7.53 (m, 2 H), 4.02 (dd, 1 H), 3.56-3.78 (m, 4 H), 3.43-3.53 (m, 1 H), 3.06-3.25 (m, 2 H), 2.27 (dt, 1 H), 1.88 (dd, 1 H), 1.58-1.81 (m, 4 H), 1.17 (dd, 1 H)

Example 19

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E19)

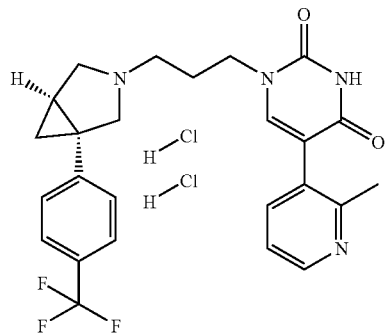

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 100 mg, 0.2 mmol) was dissolved in degassed DME-water solution (6-1, 3.5 mL). 2-Methylpyridine-3-boronic acid (69 mg, 0.4 mmol), Na$_2$CO$_3$ (67 mg, 0.6 mmol), 2-(dicyclohexylphosphino)biphenyl (14 mg, 0.04 mmol) and Pd(PPh$_3$)$_4$ (46 mg, 0.04 mmol) were added and the mixture stirred for 12 hours at 90° C. Fresh 2-(dicyclohexylphosphino)biphenyl (14 mg, 0.04 mmol) and Pd(PPh$_3$)$_4$ (46 mg, 0.04 mmol) were added and the reaction stirred at 90° C. for 2.5 h. The reaction was diluted with ethyl acetate, and washed with water. The organic phase was dried (Na$_2$SO$_4$) and evaporated; the crude was purified by flash chromatography with DCM-MeOH—NH$_4$OH (98-2-1) to give the free base of the title compound as a yellow solid (30 mg, 30% yield).

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione (30 mg) was treated with a solution of 4N HCl in dioxane (2 eq) to give the corresponding dihydrochloride salt that was purified by trituration with IPA/Et2O. After filtration, 17 mg of the title compound was recovered as a white solid.

MS (ES) (m/z): 471.22 [M+H]$^+$. $^1$H-NMR (DMSO-d$_6$, TFA) δ: 11.78 (s, 1 H), 10.98 (br. s., 1 H), 8.79 (dd, 1 H), 8.43 (dd, 1 H), 8.09 (s, 1 H), 7.96 (dd, 1 H), 7.62-7.73 (m, 2 H), 7.39-7.54 (m, 2 H), 4.05 (dd, 1 H), 3.87 (t, 2 H), 3.46-3.75 (m, 3 H), 3.17-3.34 (m, 2 H), 2.69 (s, 3 H), 2.23-2.36 (m, 1 H), 2.06-2.23 (m, 2 H), 1.81 (dd, 1 H), 1.18 (dd, 1 H)

Example 20

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E20)

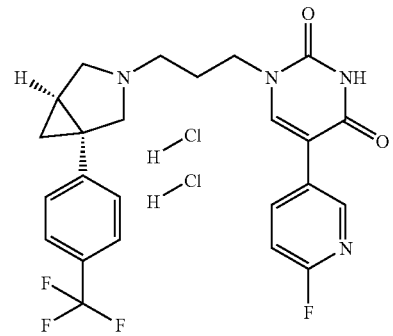

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 30 mg, 0.06 mmol) was dissolved in degassed 5-1 DME-water solution (5-1; 3 mL). 6-Fluoropyridine-3-boronic acid (17 mg, 0.12 mmol), Na$_2$CO$_3$ (14 mg, 0.13 mmol), 2-(dicyclohexylphosphino)biphenyl (4 mg, 0.01 mmol) and Pd(PPh$_3$)$_4$ (14 mg, 0.01 mmol) were added and the mixture stirred for 16 hours at 90° C. The reaction was diluted with ethyl acetate, and washed with water. The organic phase was dried (Na$_2$SO$_4$) and evaporated; the crude was purified by flash chromatography with DCM-MeOH—NH$_4$OH (94-6-1) to give the title compound (10 mg, 35% yield) as a free base.

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with a solution of 4N HCl in dioxane (2 eq) to give the corresponding dihydrochloride salt as a yellow solid that was further purified by trituration with IPA/Et2O. After filtration, 33 mg of the title compound were obtained.

MS (ES) (m/z): 475.12 [M+H]$^+$. $^1$H-NMR (MeOD) δ: 8.42 (d, 1 H), 8.20 (td, 1 H), 7.98 (s, 1 H), 7.60-7.73 (m, 2 H), 7.41-7.59 (m, 2 H), 7.13 (dd, 1 H), 4.07-4.27 (m, 1 H), 4.00 (t, 2 H), 3.82-3.95 (m, 1 H), 3.55-3.81 (m, 2 H), 3.35-3.47 (m, 2 H), 2.19-2.40 (m, 3 H), 1.29-1.56 (m, 2 H)

Example 21

5-(2-fluorophenyl)-1-(3-{(1S,5R)-1-[4-(trifluoromethyl)phenyl]-3-azabicyclo[3.1.0]hex-3-yl}propyl)-2,4(1H,3H)-pyrimidinedione hydrocholoride (E21)

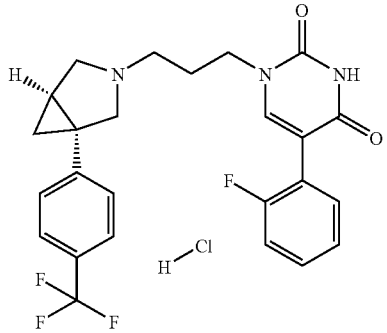

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 80 mg, 0.16 mmol) was dissolved in degassed DME-water solution (5-1, 10 mL). 0.2-Fluorophenyl-boronic acid (33 mg, 0.23 mmol), Na$_2$CO$_3$ (34 mg, 0.32 mmol), 2-(dicyclohexylphosphino)biphenyl (14 mg, 0.04 mmol) and Pd(PPh$_3$)$_4$ (46 mg, 0.04 mmol) were added and the mixture stirred for 3 hours at 90° C. The solvents were evaporated under vacuum and the crude was redissolved in ethyl acetate, and washed with water. The organic phase was dried (Na$_2$SO$_4$) and evaporated; the crude was purified by flash chromatography with DCM-MeOH—NH$_4$OH (98-2-0.2) followed by SCX cartridge washing with MeOH and eluting with MeOH/NH3 95:5 to give the title compound (58 mg, 76% yield) as free base.

5-(2-fluorophenyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with a solution of 4N HCl in dioxane (500 µl) to give the title compound as a white solid.

MS (ES) (m/z): 474.18 [M+H]$^+$. $^1$H-NMR (DMSO-d$_6$, TFA) δ: 11.06 (s, 1 H), 7.77 (d, 1 H), 7.62-7.69 (m, 2 H), 7.49-7.55 (m, 2 H), 7.35-7.48 (m, 2 H), 7.16-7.24 (m, 2 H), 3.94-4.08 (m, 1 H), 3.87 (t, 2 H), 3.56-3.79 (m, 3 H), 3.26-3.34 (m, 2 H), 2.24-2.31 (m, 1 H), 2.09-2.20 (m, 2 H), 1.56-1.62 (m, 1 H), 1.21-1.35 (m, 1 H)

Example 22

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E22)

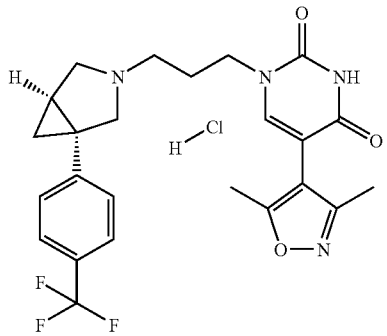

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 150 mg, 0.3 mmol) was dissolved in degassed DME-water solution (5-1, 6 mL). 3,5-Dimethyl-isoxazole-4-boronic acid (85 mg, 0.6 mmol), Na$_2$CO$_3$ (70 mg, 0.66 mmol), 2-(dicyclohexylphosphino)biphenyl (21 mg, 0.06 mmol) and Pd(PPh$_3$)$_4$ (70 mg, 0.06 mmol) were added and the mixture was refluxed for 5 hours. Then the mixture was irradiated in a microwave oven at 120° for 30 minutes. The solvents were evaporated under vacuum and the crude was redissolved in ethyl acetate, and washed with water. The organic phase was dried (Na$_2$SO$_4$) and evaporated; the crude was purified by flash chromatography with DCM-MeOH—NH$_4$OH (98-2-0.2) to give the free base of title compound (16 mg, 11% yield). The compound was further purified on SCX, washing with MeOH and eluting with MeOH/NH3 95:5.

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with a solution of 4N HCl in dioxane (500 µl) to give the title compound as a white solid.

MS (ES) (m/z): 475.19 [M+H]$^+$. $^1$H-NMR (DMSO-d$_6$, TFA) δ: 11.11 (br. s., 1 H), 7.69 (s, 1 H), 7.67 (d, 2 H), 7.52 (d, 2 H), 4.01 (br. s., 1 H), 3.86 (t, 2 H), 3.57-3.81 (m, 3 H), 3.30 (dd, 2 H), 2.32 (s, 3 H), 2.23-2.31 (m, 1 H), 2.09-2.21 (m, 5 H), 1.60-1.67 (m, 1 H), 1.19-1.35 (m, 1 H)

Example 23

5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E23)

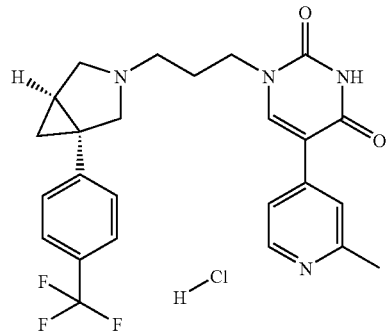

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 123 mg, 0.24 mmol) was dissolved in degassed DME-water solution (5-1, 5 mL). 2-Methylpyridine 4-boronic acid (66 mg, 0.49 mmol), Na$_2$CO$_3$ (51 mg, 0.49 mmol), 2-(dicyclohexylphosphino)biphenyl (20 mg, 0.05 mmol) and Pd(PPh$_3$)$_4$ (57 mg, 0.05 mmol) were added and the mixture stirred for 3 hours at 90° C. AcOEt was added and the mixture washed with water. The organic phase was dried (Na$_2$SO$_4$) and evaporated; the crude was purified by flash chromatography with DCM-MeOH—NH$_4$OH (98-2-0.2) to give the title compound (30 mg, 27% yield) as free base 5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with a solution of 4N HCl in dioxane (1 eq) to give the title compound as a white solid. (32 mg)

MS (ES) (m/z): 471.15 [M+H]$^+$. $^1$H-NMR (DMSO-d$_6$, TFA) δ: 11.90 (s, 1 H), 10.95 (br. s., 1 H), 8.85 (s, 1 H), 8.71 (d, 1 H), 8.34 (d, 1 H), 8.30 (dd, 1 H), 7.65-7.71 (m, 2 H), 7.45-7.53 (m, 2 H), 4.05 (d, 1 H), 3.96 (t, 2 H), 3.45-3.76 (m, 3 H), 3.19-3.34 (m, 2 H), 2.72 (s, 3 H), 2.12-2.32 (m, 3 H), 1.82 (dd, 1 H), 1.18 (dd, 1 H)

Example 24

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrocholoride (E24)

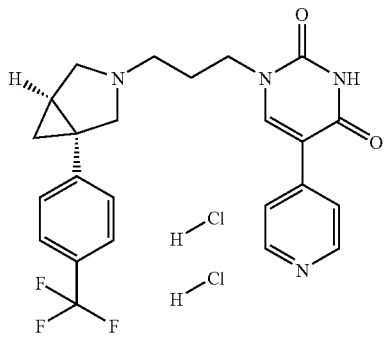

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 46 mg, 0.09 mmol) was dissolved in degassed DME-water solution (5-1, 1 mL). Pyridine 4-boronic acid (22 mg, 0.18 mmol), Na₂CO₃ (20 mg, 0.18 mmol), 2-(dicyclohexylphosphino)biphenyl (7 mg, 0.02 mmol) and Pd(PPh₃)₄ (20 mg, 0.02 mmol) were added and the mixture was placed in a microwave oven and heated at 150° for 20 minutes. The mixture was diluted with ethyl acetate, and washed with water. The organic phase was dried (Na₂SO₄) and evaporated; the crude was dissolved in MeOH and loaded on SCX cartridge washing with MeOH and eluting with MeOH/NH3 95:5. The residue was purified by flash chromatography with DCM-MeOH—NH₄OH (99-1-0.1) to give the title compound (13 mg, 32% yield) as free base.

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with a solution of 4N HCl in dioxane (2 eq) to give the title compound as a white solid. (13 mg, 32%)

MS (ES) (m/z): 457.21 [M+H]⁺. ¹H-NMR (DMSO-d₆, TFA) δ: 11.92 (s, 1 H), 11.01 (br. s., 1 H), 8.90 (s, 1 H), 8.86 (d, 2 H), 8.48 (d, 2 H), 7.66-7.73 (m, 2 H), 7.46-7.54 (m, 2 H), 3.89-4.12 (m, 3 H), 3.67-3.76 (m, 1 H), 3.57-3.65 (m, 1 H), 3.43-3.57 (m, 1 H), 3.17-3.33 (m, 2 H), 2.11-2.32 (m, 3 H), 1.84 (dd, 1 H), 1.14-1.27 (m, 1 H)

Example 25

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E25)

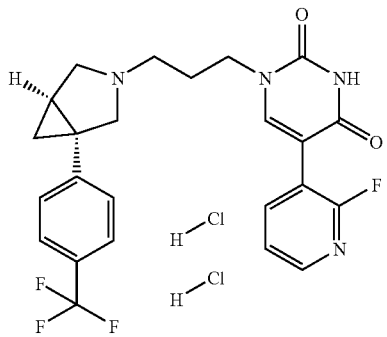

Step a)

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep. 40, 80 mg, 0.16 mmol) was dissolved in degassed MeOH (2 ml). 2-Fluoro-pyridine-3-boronic acid (45 mg, 0.32 mmol), KF (18 mg, 0.32 mmol), and Pd(OAc)₂ (8 mg, 10% weight) were added and the mixture was irradiated in a microwave oven at 120° for 20 minutes. The solvent was evaporated under vacuum and the crude was redissolved in ethyl acetate, and washed with water. The organic phase was dried (Na₂SO₄) and evaporated. A second batch of this compound was prepared starting from 5-Iodo-1-{3-[(1S,5R)-1-(4-trifluoromethyl-phenyl)-3-aza-bicyclo[3.1.0]hex-3-yl]-propyl}-1H-pyrimidine-2,4-dione (50 mg, 0.1 mmol) and using the same synthetic procedure. The crudes deriving from the two batches were mixed and purified by flash chromatography with DCM-MeOH (98-2) to give the title compound (22 mg, 27% yield) as free base.

Step b)

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione (22 mg) was dissolved in dioxane and then treated with a solution of 4N HCl in dioxane (2 eq) to give the title compound as a white solid. (21 mg)

MS (ES) (m/z): 475.12 [M+H]⁺. ¹H-NMR (DMSO-d₆, TFA) δ: 11.20 (br. s., 1 H), 8.19 (ddd, 1 H), 8.02 (ddd, 1 H), 7.90 (s, 1H), 7.67 (d, 2 H), 7.52 (d, 2 H), 7.37 (ddd, 1 H), 3.94-4.08 (m, 2 H), 3.88 (t, 2 H), 3.61-3.76 (m, 2 H), 3.27-3.34 (m, 2 H), 2.25-2.35 (m, 1 H), 2.10-2.20 (m, 2 H), 1.54-1.61 (m, 1 H), 1.27-1.36 (m, 1 H)

Example 26

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E26)

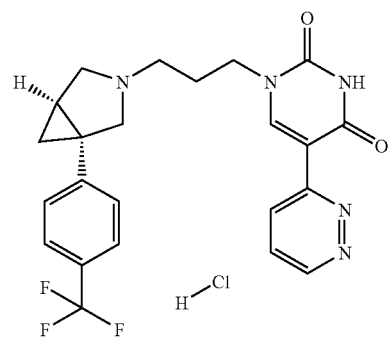

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 200 mg, 0.4 mmol) was dissolved in degassed dry DMF (10 mL). 3-(Tributylstannyl)pyridazine (147 mg, 0.4 mmol), and Pd(PPh₃)₄ (92 mg, 0.08 mmol) were added and the mixture was stirred for 4 hours at 90° C. A 5% aqueous solution of NaHCO₃$_{aq}$ was added and the reaction mixture washed with Et₂O and the product was finally extracted with ethyl acetate. The organic phase was dried (Na₂SO₄) and evaporated; the crude was purified by preparative HPLC/MS to give the title compound as trifluoroacetate salt that was further purified by flash chromatography with DCM-MeOH—NH₄OH (95-5-1) to give the title compound as free base (12 mg, 8% yield).

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in dioxane and then treated with a solution of 4N HCl in dioxane (500 µl) to give the title compound as a pale yellow solid. (15 mg, 7%)

MS (ES) (m/z): 458.16 [M+H]$^+$. $^1$H-NMR (DMSO-d$_6$, TFA) δ: 11.87 (s, 1 H), 11.29 (br. s., 1 H), 9.72 (dd, 1 H), 9.32 (dd, 1 H), 8.83 (s, 1 H), 8.38 (dd, 1 H), 7.64-7.77 (m, 2 H), 7.45-7.56 (m, 2 H), 3.95 (t, 2 H), 3.43-3.76 (m, 4 H), 3.19-3.35 (m, 2 H), 2.15-2.32 (m, 3 H), 1.96 (dd, 1 H), 1.16 (dd, 1 H).

Example 27

5-(3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E27)

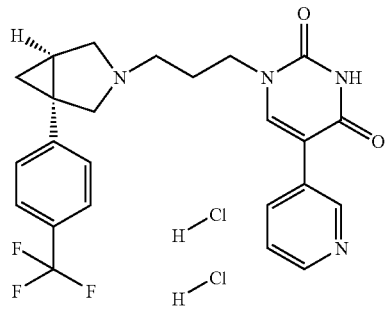

A solution of 1-(3-chloro-propyl)-5-pyridin-3-yl-1H-pyrimidine-2,4-dione (Prep43, 92 mg, 0.34 mmol), (1S,5R)-1-(4-trifluoromethyl-phenyl)-3-aza-bicyclo[3.1.0]hexane (Prep4, 68 mg, 0.34 mmol), and DIPEA (134 µl, 1 mmol) in absolute EtOH (3 mL) was placed in a microwave oven and irradiated at 130° C. for 3 hours. The solvent was removed under vacuum and the residue was partitioned between water and ethyl acetate. The organic phase was dried (Na$_2$SO$_4$), filtered and evaporated. The residue was purified by preparative LC-MS. After treatment with 4N HCl in dioxane (2 eq), the title compound was obtained (5 mg, 4% yield)

ESMS m/z 457.21 [M+H]$^+$. $^1$H-NMR (DMSO-d$_6$, TFA) δ: 11.83 (s, 1 H), 9.17 (s, 1 H), 8.81 (d, 1 H), 8.74 (dt, 1 H), 8.50 (s, 1 H), 8.03 (dd, 1 H), 7.64-7.77 (m, 2 H), 7.40-7.53 (m, 2 H), 4.06 (d, 1 H), 3.90 (t, 2H), 3.45-3.76 (m, 3 H), 3.17-3.32 (m, 2 H), 2.22-2.34 (m, 1 H), 2.07-2.22 (m, 2 H), 1.65-1.82 (m, 1 H), 1.15-1.26 (m, 1 H)

Example 28

5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione dihydrochloride (E28)

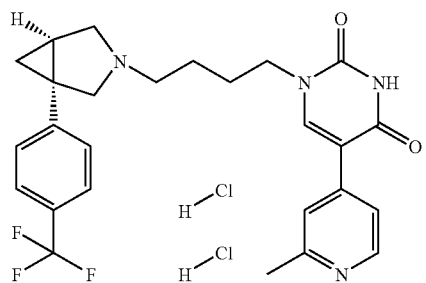

A solution of 1-(4-Chloro-butyl)-5-(2-methyl-pyridin-4-yl)-1H-pyrimidine-2,4-dione (Prep46, 74 mg, 0.25 mmol), (1S,5R)-1-(4-trifluoromethyl-phenyl)-3-aza-bicyclo[3.1.0]hexane (Prep4, 57 mg, 0.25 mmol), and TEA (101 µl, 1 mmol) in absolute EtOH (3 mL) was refluxed for 48 hours. The reaction was then evaporated under vacuum and the residue was dissolved in 2N HCl$_{aq}$ and washed with ethyl acetate. The aqueous phase was then basified with solid NaHCO$_3$ and extracted with ethyl acetate. The organic phase was dried (Na$_2$SO$_4$) and evaporated; the residue was dissolved in DCM and treated with PS-isocyanate (250 mg) resin under stirring for 2 h. After filtration and evaporation of the solvent the crude was purified by LC-MS preparative and then loaded on SCX cartridge washing with MeOH and eluting with MeOH/NH3 95:5 to give 30 mg of the title compound as free base (33%, yield). 5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione was dissolved in dioxane and then treated with a solution of 4N HCl in dioxane (2 eq) to give the title compound as a pale yellow solid. (33 mg, 23.5%)

MS (ES) (m/z): 485.22 [M+H]$^+$. $^1$H-NMR (DMSO-d$_6$, TFA) δ: 11.87 (s, 1 H), 10.80 (br. s., 1 H), 8.81 (s, 1 H), 8.70 (d, 1 H), 8.34 (d, 1 H), 8.31 (dd, 1 H), 7.61-7.72 (m, 2 H), 7.46-7.59 (m, 2 H), 4.04 (dd, 1 H), 3.87 (t, 2 H), 3.43-3.74 (m, 4 H), 3.14-3.30 (m, 2 H), 2.71 (s, 3 H), 2.28 (dt, 1 H), 1.66-1.86 (m, 4 H), 1.13-1.28 (m, 1 H).

Example 29

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione dihydrochloride (E29)

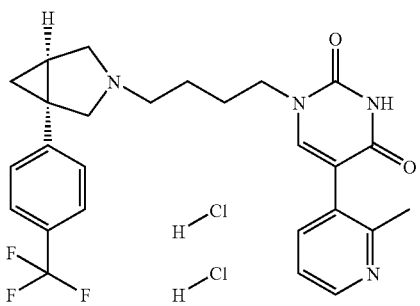

A solution of 1-(4-chloro-butyl)-5-(2-methyl-pyridin-2-yl)-1H-pyrimidine-2,4-dione (Prep48, 100 mg, 0.34 mmol), (1S,5R)-1-(4-trifluoromethyl-phenyl)-3-aza-bicyclo[3.1.0]hexane (Prep4, 77 mg, 0.34 mmol), and DIPEA (132 µl, 1 mmol) in absolute EtOH (3 mL) was heated at 125° C. for 3 hours in a microwave oven. The solvent was removed under vacuum and the residue was partitioned between water and ethyl acetate. The organic phase was dried (Na$_2$SO$_4$), filtered and evaporated. The residue was dissolved in DCM and treated with PS-isocyanate resin (250 mg) under stirring for 3 h. After filtration and evaporation of the solvent, the crude was purified by flash chromatography with DCM-MeOH—NH$_4$OH (98-2-0.2) to give the title compound (60 mg, 36% yield) as free base.

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione was treated with 4N HCl in dioxane (2 eq), to give the title compound as a white powder. (68 mg, 36% yield)

$^{1}$H-NMR (CDCl$_3$) δ: 8.72 (d, 1 H), 8.33 (d, 1 H), 8.08 (s, 1 H), 7.77-7.92 (m, 1 H), 7.70 (d, 2 H), 7.49 (d, 2 H), 3.99 (t, 1 H), 3.73-3.89 (m, 2 H), 3.58-3.73 (m, 2 H), 3.28-3.55 (m, 2 H), 3.14-3.24 (m, 1 H), 2.66 (s, 3 H), 2.18-2.36 (m, 1 H), 1.92-2.05 (m, 1 H), 1.58-1.90 (m, 4 H), 1.10-1.22 (m, 1 H)[α]$^{25}_A$-47.2 (c=0.4, MeOH)

Example 30

5-(6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E30)

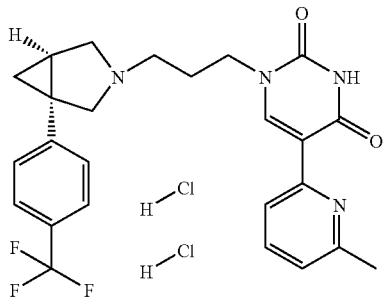

A solution of 5-(6-methyl-pyridin-2-yl)-1H-pyrimidine-2,4-dione hydrochloride (Prep50, 171 mg, 0.72 mmol), (1S,5R)-3-(3-chloro-propyl)-1-(4-trifluoromethyl-phenyl)-3-aza-bicyclo[3.1.0]hexane (Prep13, 240 mg, 0.79 mmol), and DIPEA (278 μl, 2.2 mmol) in DMSO (3 mL) was heated at 125° C. for 3 hours in a microwave oven. Water was added and the product was extracted with ethyl acetate. The crude was purified by preparative LC/MS followed by SCX cartridge washing with MeOH and eluting with MeOH/NH3 95:5 The free base obtained was treated with 4N HCl in dioxane (2 eq), to give the title compound as a white powder. (40 mg)

MS (ES) (m/z): 471.22 [M+H]$^+$. $^1$H-NMR (DMSO-d$_6$, TFA) δ: 11.46 (br. s., 1 H), 8.62 (s, 1 H), 8.09 (d, 1 H), 7.92 (t, 1 H), 7.67 (d, 2 H), 7.52 (d, 2 H), 7.35 (d, 1 H), 4.01-4.12 (m, 1 H), 3.97 (t, 2 H), 3.49-3.86 (m, 3 H), 3.25-3.38 (m, 2 H), 2.62 (s, 3 H), 2.17-2.30 (m, 3 H), 1.73-1.86 (m, 1 H), 1.16-1.27 (m, 1 H). [α]$^{20}_D$ –47.5 (c=0.4, MeOH)

Example 31

5-(2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E31)

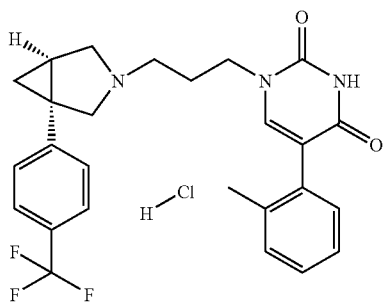

5-Phenyl-1H-pyrimidine-2,4-dione (Prep53, 52 mg, 0.25 mmol) was dissolved in MeCN-DMSO (3:1, 3 mL). Ethyl-diisopropyl-amine (132 μl, 0.8 mmol) and (1S,5R)-3-(3-chloro-propyl)-1-(4-trifluoromethyl-phenyl)-3-aza-bicyclo[3.1.0]hexane (Prep13, 69 mg, 0.3 mmol) were added. The mixture was placed in a microwave oven and then irradiated at 150° C. for 6 hours (3 cycles×1 h). A second run was performed on 5-Phenyl-1H-pyrimidine-2,4-dione (Prep53, 123 mg, 0.43 mmol), ethyl-diisopropyl-amine (0.2 μl, 1.2 mmol) and (1S,5R)-3-(3-chloro-propyl)-1-(4-trifluoromethyl-phenyl)-3-aza-bicyclo[3.1.0]hexane (Prep13, 130 mg, 0.43 mmol) in the same conditions. The two mixtures were mixed and evaporated under vacuum. The residue was dissolved in ethyl acetate and washed with water. The crude was purified by preparative LC-MS to give 79 mg of the title compound as trifluoroacetate salt. The compound was loaded on SCX cartridge washing with MeOH and then eluting with MeOH/NH3 95:5. The free base obtained was treated with 4N HCl in dioxane (2 eq), to give the title compound as a white powder (32 mg).

MS (ES) (m/z): 470.51 [M+H]$^+$. $^1$H-NMR (DMSO-d$_6$, TFA) δ: 11.44 (s, 1 H), 10.67 (br. s., 1 H), 7.71 (s, 1 H), 7.70 (d, 2 H), 7.49 (d, 2 H), 7.14-7.29 (m, 4 H), 4.07 (dd, 1 H), 3.82 (t, 2 H), 3.73 (dd, 1 H), 3.57-3.68 (m, 1 H), 3.43-3.56 (m, 1 H), 3.15-3.35 (m, 2 H), 2.25-2.33 (m, 1 H), 2.19 (s, 3 H), 2.05-2.17 (m, 2 H), 1.74 (dd, 1 H), 1.14-1.25 (m, 1 H)

Example 32

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione dihydrochloride (E32)

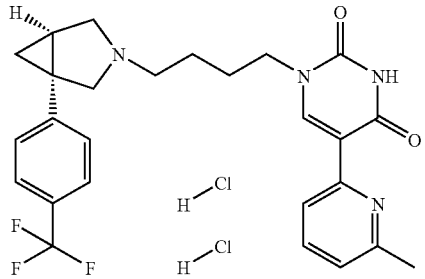

A solution of 1-(4-chloro-butyl)-5-(6-methyl-pyridin-2-yl)-1H-pyrimidine-2,4-dione (Prep51, 95 mg, 0.32 mmol), (1S,5R)-1-(4-trifluoromethyl-phenyl)-3-aza-bicyclo[3.1.0]hexane (Prep4, 74 mg, 0.32 mmol), and TEA (98 μl, 1 mmol) in absolute EtOH (4 mL) was refluxed for 48 h. Then dry DIPEA (83.6 mg, 0.64 mmol) was added and the mixture placed in a microwave oven and irradiated at 125° C. for 4 hours. The solvent was removed under vacuum and the residue was partitioned between water and ethyl acetate. The organic phase was dried (Na$_2$SO$_4$), filtered and evaporated. The residue was dissolved in DCM and treated with PS-isocyanate resin (250 mg) under stirring for 2 h. After filtration and evaporation of the solvent, the crude was purified by flash chromatography with DCM-MeOH—NH$_4$OH (98-2-0.2) to give the title compound as free base.

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione was treated with 4N HCl in dioxane (2 eq), to give the title compound as a white powder. (55 mg, 31% yield).

MS (ES) (m/z): 485.15 [M+H]$^+$. $^1$H-NMR (DMSO-d$_6$, TFA) δ: 12.04 (s, 1 H), 10.57 (br. s., 1 H), 8.77 (s, 1 H), 8.30

(dd, 1 H), 8.11 (d, 1 H), 7.60-7.72 (m, 3 H), 7.45-7.57 (m, 2 H), 4.05 (d, 1 H), 3.81-3.96 (m, 2 H), 3.47-3.78 (m, 3 H), 3.13-3.33 (m, 2 H), 2.72 (s, 3 H), 2.29 (ddd, 1 H), 1.68-1.83 (m, 5 H), 1.11-1.25 (m, 1 H)

Example 33

4-thioxo-1-(4-{(1S,5R)-1-[4-(trifluoromethyl)phenyl]-3-azabicyclo[3.1.0]hex-3-yl}butyl)-3,4-dihydro-2(1H)-pyrimidinone hydrochloride (E33)

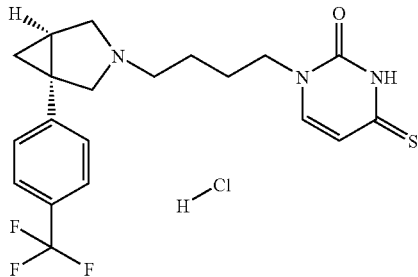

A solution of 1-(4-{(1S,5R)-1-[4-(trifluoromethyl)phenyl]-3-azabicyclo[3.1.0]hex-3-yl}butyl)-2,4(1H,3H)-pyrimidinedione (E5, 110 mg, 0.3 mmol) and Lawesson's reagent (184 mg, 0.5 mmol) in DME (2 mL) was stirred at reflux for 2 hours. The solvent was evaporated under vacuum. The crude was re-dissolved in ethyl acetate and washed with water. The organic phase was dried (Na$_2$SO$_4$) filtered and evaporated; the crude was purified by flash chromatography with DCM-MeOH—NH$_4$OH (98-2-0.2) to give the title compound as a yellow oil (80 mg, 63% yield).

4-thioxo-1-(4-{(1S,5R)-1-[4-(trifluoromethyl)phenyl]-3-azabicyclo[3.1.0]hex-3-yl}butyl)-3,4-dihydro-2(1H)-pyrimidinone was dissolved in dioxane and then treated with a solution of 4N HCl in dioxane (500 µl) to give the title compound as a yellow oil.

MS (ES) (m/z): 410.15 [M+H]$^+$. $^1$H-NMR (DMSO-d$_6$, TFA) δ: 12.63 (s, 1 H), 7.70 (d, 2 H), 7.61 (d, 1 H), 7.49 (d, 2 H), 6.27 (dd, 1 H), 4.03 (dd, 1 H), 3.72 (t, 2 H), 3.57-3.69 (m, 2 H), 3.44-3.55 (m, 1 H), 3.20 (br. s., 2 H), 2.28 (ddd, 1 H), 1.56-1.81 (m, 5 H), 1.09-1.28 (m, 1 H).

Example 34

5-(2,6-difluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E34)

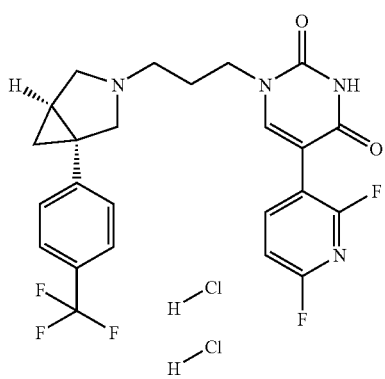

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 100 mg, 0.2 mmol) was dissolved in dry and degassed THF (2 mL). 2,6-Difluoro-pyridine-3-boronic acid (80 mg, 0.5 mmol), KF (17 mg, 0.3 mmol), and Pd(OAc)$_2$ (5 mg, 5% weight) were added and the mixture was irradiated in a microwave oven at 90° for 30 minutes. The solvent was evaporated under vacuum and the crude was redissolved in ethyl acetate, and washed with brine. The organic phase was dried (Na$_2$SO$_4$) and evaporated; the crude was purified by flash chromatography with DCM-MeOH—NH$_4$OH (99-1-0.1) to give the title compound (12 mg, 12% yield) as free base 5-(2,6-difluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in dioxane and then treated with a solution of 4N HCl in dioxane (2 eq) to give the title compound as a white solid. (12.7 mg)

MS (ES) (m/z): 493.17 [M+H]$^+$. $^1$H-NMR (DMSO-d$_6$, TFA) δ: 11.68 (s, 1 H), 10.49 (br. s., 1 H), 8.20 (dt, 1 H), 8.05 (s, 1 H), 7.70 (d, 2 H), 7.49 (d, 2 H), 7.26 (dd, 1 H), 4.06 (dd, 1 H), 3.84 (t, 2 H), 3.73 (dd, 1 H), 3.62 (dd, 1 H), 3.46-3.56 (m, 1 H), 3.18-3.34 (m, 2 H), 2.26-2.32 (m, 1 H), 2.05-2.19 (m, 2 H), 1.67 (dd, 1 H), 1.20 (dd, 1 H).

Example 35

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E35)

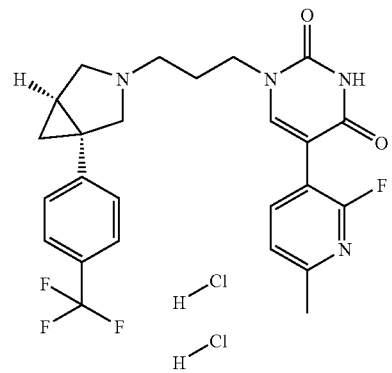

Method a):

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 150 mg, 0.3 mmol) was dissolved in degassed MeOH (4 mL). 2-Fluoro-6-methyl-pyridine-3-boronic acid (140 mg, 0.9 mmol), KF (140 mg, 2.4 mmol), and Pd(OAc)$_2$ (15 mg, 10% weight) were added and the mixture was heated to vigorous reflux for 4 hours. The solvent was evaporated under vacuum and the crude was partitioned between ethyl acetate and brine. The organic phase was dried (Na$_2$SO$_4$) and evaporated; the crude was purified by flash chromatography with DCM-MeOH—NH$_4$OH (98-2-0.2) to give the title compound (23 mg, 16% yield) as free base 5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in dioxane and then treated with a solution of 4N HCl in dioxane (2 eq) to give the title compound as a white solid.

MS (ES) (m/z): 489.19 [M+H]+. 1H-NMR (DMSO-d6) δ: 11.61 (s, 1 H), 10.16 (br. s., 1 H), 7.96 (s, 1 H), 7.87 (dd, 1 H), 7.70 (m, 2 H), 7.49 (m, 2 H), 7.25 (dd, 1 H), 3.98-4.15 (m, 1 H), 3.83 (dd, 2 H), 3.69-3.79 (m, 1 H), 3.57-3.69 (m, 1 H), 3.44-3.56 (m, 1 H), 3.18-3.35 (m, 2 H), 2.44 (s, 3 H), 2.21-2.38 (m, 1 H), 1.95-2.21 (m, 2 H), 1.47-1.68 (m, 1 H), 1.15-1.28 (m, 1 H).

Method b):

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione (E65, 90 mg, 0.18 mmol) was dissolved in 2 ml of dioxane and then 4M HCl in dioxane solution (92 μl, 0.36 mmol) was added. The mixture was stirred at room temperature for 5 minutes, and then the solvent was removed in vacuum to give 99 mg of the title compound as a white solid (96%, yield).

MS (ES) (m/z): 489.19 [M+H]+. 1H-NMR (DMSO-d6) δ: 11.61 (s, 1 H), 10.16 (br. s., 1 H), 7.96 (s, 1 H), 7.87 (dd, 1 H), 7.70 (m, 2 H), 7.49 (m, 2 H), 7.25 (dd, 1 H), 3.98-4.15 (m, 1 H), 3.83 (dd, 2 H), 3.69-3.79 (m, 1 H), 3.57-3.69 (m, 1 H), 3.44-3.56 (m, 1 H), 3.18-3.35 (m, 2 H), 2.44 (s, 3 H), 2.21-2.38 (m, 1 H), 1.95-2.21 (m, 2 H), 1.47-1.68 (m, 1 H), 1.15-1.28 (m, 1 H).

Example 36

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E36)

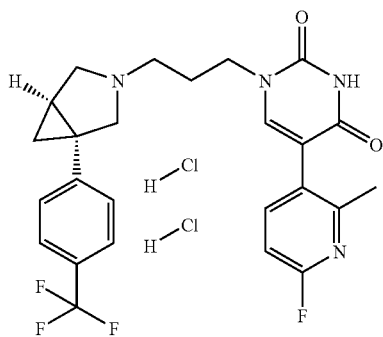

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 150 mg, 0.3 mmol) was dissolved in degassed MeOH (4 mL). 6-Fluoro-2-methyl-pyridine-3-boronic acid (140 mg, 0.9 mmol), KF (140 mg, 2.4 mmol), and Pd(OAc)2 (15 mg, 10% weight) were added and the mixture was heated to vigorous reflux for 4 hours. The solvent was evaporated under vacuum and the crude was partitioned between ethyl acetate and brine. The organic phase was dried (Na2SO4) and evaporated; the crude was purified by flash chromatography with DCM-MeOH—NH4OH (98-2-0.2) to give the title compound (7 mg) as a free base.

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione (7 mg) was dissolved in dioxane and then treated with a solution of 4N HCl in dioxane (2 eq) to give the title compound as an off-white powder (8 mg, 5% yield)

MS (ES) (m/z): 489.19 [M+H]+. 1H-NMR (DMSO-d6) δ: 11.57 (s, 1 H), 7.83 (s, 1 H), 7.75 (dd, 1 H), 7.70 (m, 2 H), 7.48 (m, 2 H), 7.03 (dd, 1 H), 3.96-4.17 (m, 1 H), 3.82 (t, 2 H), 3.46-3.78 (m, 4 H), 3.37-3.47 (m, 1 H), 2.35 (s, 3 H), 2.22-2.30 (m, 1 H), 2.10 (dt, 2 H), 1.49-1.74 (m, 1 H), 1.11-1.32 (m, 1 H).

Example 37

5-[2-(methyloxy)-3-pyridinyl]-1-(3-{(1S,5R)-1-[4-(trifluoromethyl)phenyl]-3-azabicyclo[3.1.0]hex-3-yl}propyl)-2,4(1H,3H)-pyrimidinedione (E37)

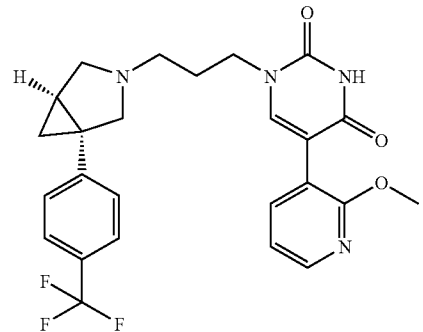

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 150 mg, 0.3 mmol) was dissolved in degassed MeOH (4 mL). 2-Methoxy-pyridine-3-boronic acid (136 mg, 0.9 mmol), KF (155 mg, 2.7 mmol), and Pd(OAc)2 (15 mg, 10% weight) were added and the mixture was heated to vigorous reflux for 2.5 hours. The mixture was diluted with MeOH, loaded on SCX cartridge washing with MeOH and MeOH/NH3 95:5. The solvent was evaporated under vacuum and the residue was purified by flash chromatography with ethyl acetate to give the title compound as free base (70 mg, 48% yield).

MS (ES) (m/z): 487.14 [M+H]+. 1H-NMR (MeOD) δ: 8.13 (dd, 1 H), 7.79 (s, 1 H), 7.75 (dd, 1 H), 7.56 (m, 2 H), 7.32 (m, 2 H), 7.01 (dd, 1 H), 3.94 (s, 3 H), 3.91 (t, 2 H), 3.42 (d, 1 H), 3.16 (d, 1 H), 2.59-2.69 (m, 3 H), 2.55 (dd, 1 H), 1.77-2.06 (m, 3 H), 1.38-1.51 (m, 1 H), 0.87 (dd, 1 H)

Example 38

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione dihydrochloride (E38)

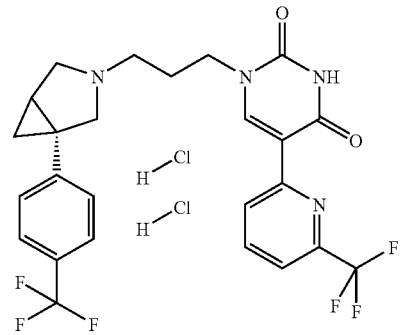

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 150 mg, 0.3 mmol) was dissolved in degassed MeOH (4 mL). 6-(Trifluoromethyl)pyridine-2-boronic acid pinacol ester (243 mg, 0.9 mmol), KF (155 mg, 2.7 mmol), and Pd(OAc)$_2$ (15 mg, 10% weight) were added and the mixture was heated to vigorous reflux for 2.5 hours. The solvent was evaporated under vacuum and the crude was partitioned between ethyl acetate and brine. The organic phase was dried (Na$_2$SO$_4$) and evaporated; the crude was purified by flash chromatography with ethyl acetate-NH$_4$OH (0.25%) to give the title compound (23 mg, 13% yield) as free base.

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione was dissolved in dioxane and then treated with a solution of 4N HCl in dioxane (2 eq) to give the title compound as a brown oil (23 mg, 15%).

MS (ES) (m/z): 525.08 [M+H]$^+$. $^1$H-NMR (MeOD) δ: 8.57 (s, 1 H), 8.56 (d, 1 H), 8.03 (dd, 1 H), 7.61-7.74 (m, 3 H), 7.50 (m, 2 H), 4.11-4.26 (m, 1 H), 4.07 (dd, 2 H), 3.81-3.95 (m, 1 H), 3.57-3.77 (m, 3 H), 3.36-3.45 (m, 1 H), 2.15-2.41 (m, 3 H), 1.27-1.46 (m, 3H)

Example 39

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E39)

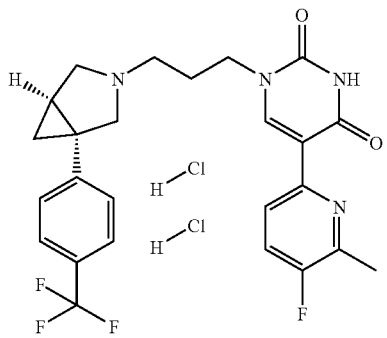

Step a
5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 150 mg, 0.3 mmol) was dissolved in degassed MeOH (4 mL). 5-Fluoro-6-methyl-pyridine-2-boronic acid pinacol ester (220 mg, 0.9 mmol), KF (155 mg, 2.6 mmol), and Pd(OAc)$_2$ (20 mg, 10% weight) were added and the mixture was heated to 85° C. for 2.5 hours. The solvent was evaporated under vacuum and the crude was partitioned between ethyl acetate and water. The organic phase was dried (Na$_2$SO$_4$) and evaporated; the residue was loaded on SCX cartridge washing with MeOH and eluting with MeOH/NH3 99.5:0.5. The crude was then purified by flash chromatography with ethyl acetate-NH$_4$OH (0.25%) to give the title compound (8 mg, 5%) as free base.

Step b
5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione (8 mg) was dissolved in dioxane and then a solution of 4N HCl in dioxane (2 eq) was added to give the title compound as pale yellow solid (8 mg, 5% yield)

MS (ES) (m/z): 489.12 [M+H]$^+$. $^1$H-NMR (MeOD) δ: 8.76 (s, 1 H), 8.24 (dd, 1 H), 8.01 (t, 1 H), 7.66 (m, 2 H), 7.51 (m, 2 H), 4.19 (d, 1 H), 4.09 (t, 2 H), 3.91 (d, 1 H), 3.63-3.78 (m, 2 H), 3.38-3.52 (m, 2 H), 2.69 (d, 3 H), 2.25-2.41 (m, 3 H), 1.58 (dd, 1 H), 1.25-1.40 (m, 1 H)

Example 40

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E40)

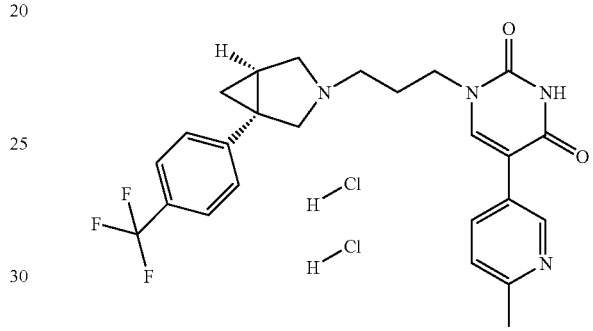

To a solution of 3-[5-(6-Methyl-pyridin-3-yl)-2,4-dioxo-3,4-dihydro-2H-pyrimidin-1-yl]-propionaldehyde (Prep59, 90 mg, 0.35 mmol), (1S,5R)-1-(4-trifluoromethyl-phenyl)-3-aza-bicyclo[3.1.0]hexane (Prep4, 71 mg, 0.31 mmol) and AcOH (21 mg, 0.35 mmol) in dichloroethane (2 mL), NaBH(AcO)$_3$ (77 mg, 0.36 mmol) was added portionwise at 0° C. The mixture was stirred at 0° C. for further 45 minutes, then a 1N solution of NaOH was added and the mixture extracted with EtOAc. The organic phase was dried and evaporated, the residue redissolved in DCM and treated with PS-isocyanate resin (400 mg) under stirring for 4 h. After filtration, the solvent was evaporated under vacuum, and the crude was purified by flash chromatography with DCM-MeOH—NH$_4$OH (95-5-0.5) to give the title compound (65 mg, 40% yield) as free base.

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in dioxane and treated with 4N HCl in dioxane (2 eq), to give the title compound as a white powder (65 mg, 34.4% yield)

MS (ES) (m/z): 471.08 [M+H]$^+$. $^1$H-NMR (MeOD) δ: 9.10 (d, 1 H), 8.71 (dd, 1 H), 8.37 (s, 1 H), 7.90 (d, 1 H), 7.67 (m, 2 H), 7.51 (m, 2 H), 4.19 (d, 1 H), 4.04 (t, 2 H), 3.91 (d, 1 H), 3.61-3.80 (m, 2 H), 3.37-3.45 (m, 2 H), 2.79 (s, 3 H), 2.26-2.37 (m, 3 H), 1.45-1.62 (m, 1 H), 1.25-1.44 (m, 1 H).

Example 41

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione hydrochloride (E41)

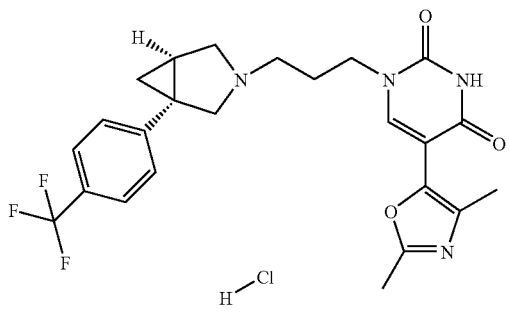

To a solution of 3-[5-(2,4-Dimethyl-oxazol-5-yl)-2,4-dioxo-3,4-dihydro-2H-pyrimidin-1-yl]-propionaldehyde (Prep64, 74 mg, 0.28 mmol) in dichloroethane (2 mL), (1S,5R)-1-(4-trifluoromethyl-phenyl)-3-aza-bicyclo[3.1.0]hexane (Prep4, 57.4 mg, 0.25 mmol), AcOH (18.5 mg, 0.28 mmol) and NaBH(AcO)$_3$ (65 mg, 0.31 mmol) were added portionwise at 0° C. The mixture was stirred at 0° C. for further 30 minutes. A 1N solution of NaOH was added and the mixture extracted with EtOAc. The organic phase was treated with PS isocyanate resin, filtered and evaporated under vacuum. The crude was purified by flash chromatography (DCM/MeOH/NH4OH 95:5:05) to give the title compound as free base. The free base was dissolved in dissolved in dioxane and treated with 4N HCl in dioxane (1 eq), to give the title compound as a white powder. (38 mg, 24%)

MS (ES) (m/z): 475.12 [M+H]$^+$. $^1$H-NMR (DMSO-d$_6$, TFA) δ: 11.61 (s, 1 H), 10.44 (br. s., 1 H), 7.94 (s, 1 H), 7.70 (d, 2 H), 7.49 (d, 2 H), 4.05 (dd, 1 H), 3.84 (t, 2 H), 3.72 (dd, 1 H), 3.62 (dd, 1 H), 3.45-3.56 (m, 1 H), 3.16-3.33 (m, 2 H), 2.37 (s, 3 H), 2.25-2.34 (m, 1 H), 2.08 (s, 3 H), 2.03-2.17 (m, 2 H), 1.66 (dd, 1 H), 1.15-1.31 (m, 1 H)

Example 42

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione hydrochloride (E42)

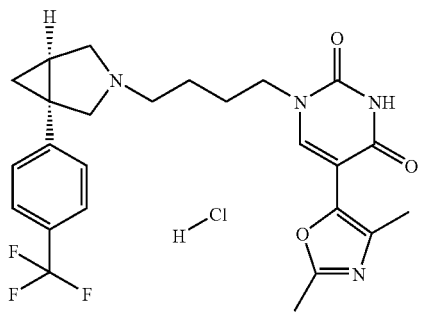

A solution of 1-(4-chloro-butyl)-5-(2,4-dimethyl-oxazol-5-yl)-1H-pyrimidine-2,4-dione (Prep65, 100 mg, 0.34 mmol), (1S,5R)-1-(4-trifluoromethyl-phenyl)-3-aza-bicyclo[3.1.0]hexane (Prep4, 68 mg, 0.3 mmol), and DIPEA (130 mg, 1 mmol) in absolute EtOH (3 ml) was placed in a microwave oven and irradiated at 130° C. for 3 hours. The solvent was removed under vacuum and the residue was partitioned between water and ethyl acetate. The organic phase was evaporated, the crude dissolved in dichloromethane and treated with PS-isocyanate resin (400 mg) under stirring for 3 h. After filtration, the solvent was evaporated and the crude purified by preparative LC-MS. The residue was loaded over a SCX cartridge eluting with MeOH and the product obtained was treated with 4N HCl in dioxane (1 eq), to give the title compound as a white powder. (43 mg, 24% yield).

MS (ES) (m/z): 489.15 [M+H]$^+$. $^1$H-NMR (DMSO-d$_6$, TFA) δ: 11.56 (s, 1 H), 10.71 (br. s., 1 H), 7.96 (s, 1 H), 7.70 (d, 2 H), 7.49 (d, 2 H), 4.03 (dd, 1 H), 3.76 (t, 2 H), 3.57-3.73 (m, 2 H), 3.45-3.54 (m, 1 H), 3.10-3.28 (m, 2 H), 2.36 (s, 3 H), 2.25-2.31 (m, 1 H), 2.07 (s, 3 H), 1.61-1.81 (m, 5 H), 1.18 (dd, 1 H). [α]$^{20}_D$ −41 (c=0.4, MeOH)

Example 43

5-(5-chloro-2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E43)

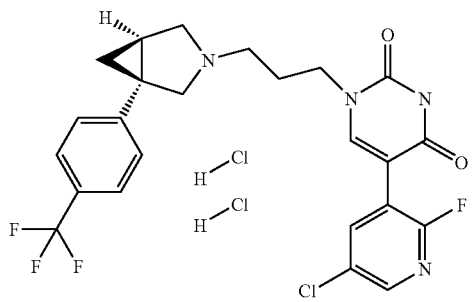

A mixture of 5-iodo-1-{3-[(1S,5R)-1-(4-trifluoromethyl-phenyl)-3-aza-bicyclo[3.1.0]hex-3-yl]-propyl}-1H-pyrimidine-2,4-dione (Prep 40, 150 mg, 0.3 mmol), 2-fluoro-5-chloropyridine-3-boronic acid (142 mg, 0.9 mmol), KF (157 mg, 2.7 mmol), and Pd(OAc)$_2$ (20 mg) in degassed MeOH (4 ml) was placed in a microwave oven and warmed at 120° C. for 25 minutes. The mixture was filtered, MeOH was evaporated and the crude partitioned between brine and ethyl acetate. The organic phase was dried (Na$_2$SO$_4$) and evaporated; the crude was purified by flash chromatography with ethyl acetate-NH$_4$OH (0.5%) to give the title compound (10 mg, 6% yield).

5-(5-chloro-2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with a solution of 4N HCl in dioxane (2 eq) to give the title compound.

MS (ES) (m/z): 509.15 [M+H]$^+$. $^1$H-NMR (DMSO-d$_6$, TFA) δ: 11.72 (s, 1 H), 8.31 (dd, 1 H), 8.17 (dd, 1 H), 8.11 (s, 1 H), 7.70 (d, 2 H), 7.49 (d, 1 H), 3.99-4.11 (m, 1 H), 3.78-3.90 (m, 2 H), 3.44-3.77 (m, 4 H), 3.19-3.28 (m, 1 H), 2.23-2.34 (m, 1 H), 2.01-2.17 (m, 2 H), 1.53-1.68 (m, 1 H), 1.16-1.30 (m, 2 H).

Example 44

5-(3-fluoro-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E44)

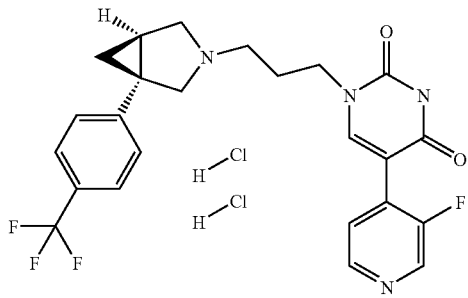

3-[5-(3-Fluoro-pyridin-4-yl)-2,4-dioxo-3,4-dihydro-2H-pyrimidin-1-yl]-propionaldehyde (Prep69, 63 mg, 0.24 mmol) was dissolved in DCM-MeOH 1-1 (2 ml). The resulting solution was cooled at 0° C. and then (1S,5R)-1-(4-trifluoromethyl-phenyl)-3-aza-bicyclo[3.1.0]hexane (54 mg, 0.24 mmol), AcOH (17 μl) and NaBH(AcO)$_3$ (55 mg, 0.26 mmol) were added. The mixture was left to reach room temperature and the stirring was prolonged for further 18 hours. 1N NaOH was added and the product was extracted with DCM. The organic phase was dried (Na$_2$SO$_4$) and evaporated. The crude was redissolved in DCM and treated with PS-isocyanate (300 mg) overnight. The residue was finally purified with SCX cartridge, washing with MeOH and then collecting the product with MeOH—NH$_4$OH (95-5) to give 17 mg of the title compound (16% yield).

5-(3-fluoro-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in dioxane and treated with 4N HCl in dioxane (2 eq), to give the title compound as a white powder.

MS (ES) (m/z): 475.34 [M+H]$^+$. $^1$H-NMR (DMSO-d$_6$, TFA) δ: 11.72 (s, 1 H), 10.48 (br. s., 1 H), 8.64 (d, 1 H), 8.48 (dd, 1 H), 8.14 (s, 1 H), 7.70 (m, 2 H), 7.61 (dd, 1 H), 7.49 (m, 2 H), 4.06 (dd, 1 H), 3.87 (t, 2 H), 3.47-3.80 (m, 3 H), 3.20-3.36 (m, 2 H), 2.26-2.38 (m, 1 H), 2.00-2.22 (m, 2 H), 1.59-1.76 (m, 1 H), 1.10-1.30 (m, 1 H)

Example 45

5-(2-chloro-5-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E45)

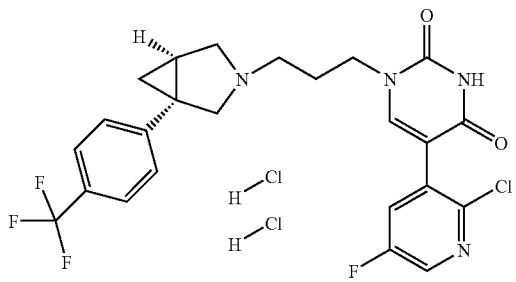

3-[5-(2-Chloro-5-fluoro-pyridin-3-yl)-2,4-dioxo-3,4-dihydro-2H-pyrimidin-1-yl]-propionaldehyde (Prep73, 90 mg, 0.27 mmol), (1S,5R)-1-(4-trifluoromethyl-phenyl)-3-aza-bicyclo[3.1.0]hexane (61 mg, 0.27 mmol), and AcOH (16 mg, 0.27 mmol) in dichloroethane-MeOH 1-1 (4 ml) were stirred until complete dissolution, NaBH(AcO)$_3$ (86 mg, 0.40 mmol) was then added portionwise at 0° C. The mixture was stirred at 0° C. for further 1 hour, basified with 2N NaOH and then extracted with ethyl acetate. The organic phase was dried (Na$_2$SO$_4$) and evaporated. The crude was purified by preparative LC-MS. The so obtained trifluoroacetate salt was further purified by flash chromatography with DCM-MeOH—NH$_4$OH (95-5-0.5) to afford 4.5 mg of the title compound (3% yield).

5-(2-chloro-5-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in dioxane and treated with 4N HCl in dioxane (2 eq), to give the title compound as a white powder.

MS (ES) (m/z): 509.15 [M+H]$^+$. $^1$H-NMR (DMSO-d$_6$, TFA) δ: 11.71 (s, 1 H), 10.35 (br. s., 1 H), 8.50 (d, 1 H), 8.03 (s, 1 H), 7.89 (dd, 1 H), 7.70 (m, 2 H), 7.50 (m, 2 H), 4.08 (dd, 1 H), 3.84 (t, 2 H), 3.75 (dd, 1 H), 3.63 (dd, 1 H), 3.44-3.57 (m, 1 H), 3.18-3.36 (m, 2 H), 2.24-2.36 (m, 1 H), 2.03-2.22 (m, 2 H), 1.63 (dd, 1 H), 1.14-1.30 (m, 1 H)

Example 46

5-(6-fluoro-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E46)

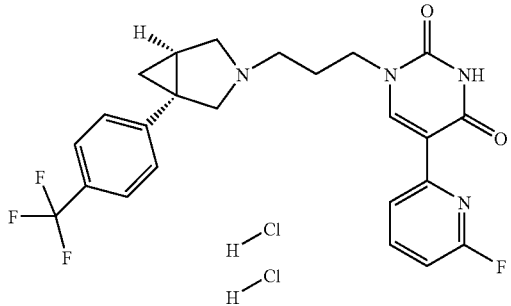

A solution of 3-[5-(6-Fluoro-pyridin-2-yl)-2,4-dioxo-3,4-dihydro-2H-pyrimidin-1-yl]-propionaldehyde (Prep77, 170 mg, 0.57 mmol), (1S,5R)-1-(4-trifluoromethyl-phenyl)-3-aza-bicyclo[3.1.0]hexane (115 mg, 0.51 mmol), and AcOH (34 mg, 0.57 mmol) in dichloroethane (4 ml) was cooled to 0° C. NaBH(AcO)$_3$ (180 mg, 0.85 mmol) was added portionwise. The mixture was stirred at 0° C. for further 1 hour and then basified with 1N NaOH. Brine was added and the product extracted with ethyl acetate. The organic phase was dried (Na$_2$SO$_4$) and evaporated. The crude was purified by preparative LC-MS. The so obtained trifluoroacetate salt was passed over a SCX cartridge to give 18 mg of the title compound (8% yield).

5-(6-fluoro-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in dioxane and treated with 4N HCl in dioxane (2 eq), to give the title compound as a off-white powder.

MS (ES) (m/z): 475.14 [M+H]$^+$. $^1$H-NMR (DMSO-d$_6$, TFA) δ: 11.67 (s, 1 H), 10.71 (br. s., 1 H), 8.52 (s, 1 H), 8.20-8.29 (m, 1 H), 7.99 (dt, 1 H), 7.68 (m, 2 H), 7.48 (m, 2 H), 7.02-7.11 (m, 1 H), 4.04 (dd, 1 H), 3.85-3.99 (m, 2 H), 3.54-3.80 (m, 2 H), 3.42-3.54 (m, 1 H), 3.19-3.35 (m, 2 H), 2.22-2.37 (m, 1 H), 1.97-2.22 (m, 2 H), 1.74 (dd, 1 H), 1.18 (dd, 1 H)

Example 47

6-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile dihydrochloride (E47)

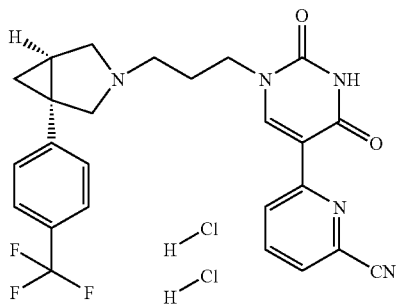

A solution of 6-(2,4-Dioxo-1,2,3,4-tetrahydro-pyrimidin-5-yl)-pyridine-2-carbonitrile hydrochloride (Prep79, 106 mg, 0.42 mmol), (1S,5R)-3-(3-chloro-propyl)-1-(4-trifluoromethyl-phenyl)-3-aza-bicyclo[3.1.0]hexane (133 mg, 0.44 mmol), KI (1 mg) and DIPEA (103 mg, 0.8 mmol) in DMSO (1 ml) was heated at 125° C. for 3 hours in a microwave oven. Water was added and the product was extracted with diethylether. The organic layer washed with brine, dried ($Na_2SO_4$) and evaporated. The residue was purified by preparative LC/MS. The so obtained trifluoroacetate salt was passed over a SCX cartridge to afford the title compound.

6-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile was dissolved in dioxane and treated with 4N HCl in dioxane (2 eq), to give 68 mg of the title compound as a white powder (29% yield)

MS (ES) (m/z): 482.05 [M+H]$^+$. $^1$H-NMR (DMSO-d$_6$, TFA) δ: 1.74 (s, 1 H), 10.64 (br. s., 1 H), 8.59 (s, 1 H), 8.53 (dd, 1 H), 8.00-8.12 (m, 1 H), 7.91 (dd, 1 H), 7.69 (m, 2 H), 7.49 (m, 2 H), 4.05 (dd, 1 H), 3.97 (t, 2 H), 3.72 (dd, 1 H), 3.58-3.67 (m, 1 H), 3.44-3.56 (m, 1 H), 3.19-3.33 (m, 2 H), 2.23-2.35 (m, 1 H), 2.04-2.23 (m, 2 H), 1.68-1.82 (m, 1 H), 1.13-1.23 (m, 1 H)

Examples 48-50

The following examples (E48-E50) were prepared using a similar procedure as set out earlier in Example 25 (step a) for Free Bases and Step b) for hydrochloride salts) starting from 2-Fluoro-pyridine-3-boronic acid and the appropriate iodo derivative (SM).

| Examples | SM | Analytical data ([MH]$^+$ Free Base, $^1$H NMR) |
|---|---|---|
| E48 Free Base: 5-(2-fluoro-3-pyridinyl)-1-(3-{(1S,5R)-1-[2-fluoro-4-(trifluoromethyl)phenyl]-3-azabicyclo[3.1.0]hex-3-yl}propyl)-2,4(1H,3H)-pyrimidinedione | P85 | MS (ES) (m/z): 493 [MH$^+$]; $C_{24}H_{21}F_5N_4O_2$ requires 492.45 $^1$H-NMR (CDCl$_3$) δ ppm 8.17-8.27(m, 3H)7.66-7.73(m, 1H)7.33-7.36(m, 2H)7.26-7.32(m, 2H)3.94(t, 2H)3.26(dd, 1H)3.11(d, 1H)2.56-2.62(m, 3H)2.45-2.51(m, 1H)1.89-1.98(m, 2H)1.78-1.83(m, 1H)1.34-1.39(m, 1H)0.81-0.86(m, 1H) |
| Example 48: 5-(2-fluoro-3-pyridinyl)-1-(3-{(1S,5R)-1-[2-fluoro-4-(trifluoromethyl)phenyl]-3-azabicyclo[3.1.0]hex-3-yl}propyl)-2,4(1H,3H)-pyrimidinedione dihydrochloride | | MS (ES) (m/z): 493: [MH$^+$]; $C_{24}H_{21}F_5N_4O_2$ requires 492.45 $^1$H NMR (DMSO-d$_6$) δ ppm 11.62-11.72(m, 1H)10.40(br.s., 1H)8.20-8.24(m, 1H)8.03(br.s., 1H)7.97-8.02(m, 1H)7.70-7.76(m, 1H)7.58-7.68(m, 2H)7.39-7.46(m, 1H)3.94-4.02(m, 1H)3.83(t, 2H)3.73-3.80(m, 1H)3.50-3.59(m, 1H)3.44(t, 1H)3.16-3.30(m, 2H)2.26-2.41(m, 1H)2.01-2.15(m, 2H)1.58-1.68(m, 1H)1.07-1.19(m, 1H) |
| E49 Free Base: 5-(2-fluoro-3-pyridinyl)-1-(3-{(1S,5R/1R,5S)-1-[3-(trifluoromethyl)phenyl]-3-azabicyclo[3.1.0]hex-3-yl}propyl)-2,4(1H,3H)-pyrimidinedione | P83 | MS (ES) (m/z): 475 [MH$^+$]; $C_{24}H_{22}F_4N_4O_2$ requires 474.46 $^1$H-NMR (CDCl$_3$) δ ppm 8.35(br.s., 1H)8.15-8.25(m, 2H)7.68-7.73(m, 1H)7.30-7.49(m, 5H)3.90-3.97(m, 2H)3.34(d, 1H)3.11(d, 1H)2.55-2.64(m, 3H)2.49-2.56(m, 1H)1.90-2.00(m, 2H)1.75-1.82(m, 1H)1.37-1.45(m, 1H)0.81-0.89(m, 1H) |
| Example 49: 5-(2-fluoro-3-pyridinyl)-1-(3-{(1S,5R/1R,5S)-1-[3-(trifluoromethyl)phenyl]-3-azabicyclo[3.1.0]hex-3-yl}propyl)-2,4(1H,3H)-pyrimidinedione dihydrochloride | | MS (ES) (m/z): 475 [MH$^+$]; $C_{24}H_{22}F_4N_4O_2$ requires 474.46 $^1$H NMR (500 MHz, MeOD) δ ppm 8.19(d, 1H)8.01-8.12(m, 1H)7.90-7.96(m, 1H)7.50-7.73(m, 4H)7.33-7.41(m, 1H)4.09-4.23(m, 1H)3.97(t, 2H)3.81-3.92(m, 1H)3.65(br.s., 2H)3.39(br.s., 2H)2.32(br.s., 1H)2.18(br.s., 2H)1.29-1.43(m, 2H) |
| E50 Free Base: 1-{3-[(1S,5R/1R,5S)-1-(4-chlorophenyl)-3-azabicyclo[3.1.0]hex-3-yl]propyl}-5-(2-fluoro-3-pyridinyl)-2,4(1H,3H)-pyrimidinedione | P81 | MS (ES) (m/z): 441 [MH$^+$]; $C_{23}H_{22}ClFN_4O_2$ requires 440.90 $^1$H-NMR (CDCl$_3$) δ ppm 8.38(br.s., 1H)8.15-8.25(m, 2H)7.65-7.73(m, 1H)7.25-7.31(m, 1H)7.25(d, 2H)7.08(d, 2H)3.89-3.98(m, 2H)3.28(d, 1H)3.07(d, 1H)2.45-2.63(m, 4H)1.89-1.99(m, 2H)1.66-1.73(m, 1H)1.31-1.37(m, 1H)0.75-0.84(m, 1H) |

Example 51

5-(4-fluoro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione (E51)

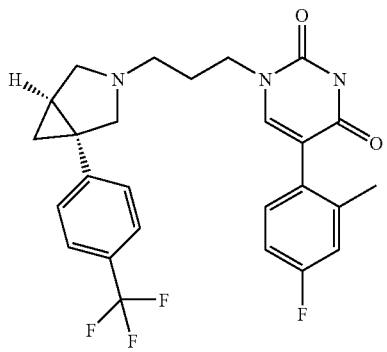

5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40, 75 mg, 0.15 mmol) was dissolved in 1,2-dimethoxyethane (DME) (4 ml) and water (0.80 ml). (4-Fluoro-2-methylphenyl)boronic acid (32 mg, 0.21 mmol) (commercial source Aldrich), sodium carbonate (31.5 mg, 0.297 mmol), 2-(dicyclohexylphosphino)biphenyl (13.01 mg, 0.037 mmol) and Pd(PPh$_3$)$_4$ (42.9 mg, 0.037 mmol) were added and the mixture was heated at 90° C. for 18 hours.

The reaction was quenched with water (3 ml) and the organic layers were extracted with DCM (3×4 ml) The organic layers were combined, dried over Na$_2$SO$_4$, filtered and concentrated in vacuo. The crude material was passed through SCX (2 g) cartridge (eluting with methanol followed by 2N ammonia solution in methanol) and then purified by preparative HPLC chromatography using a MDAP Waters FractionLynx Autopurification System™ equipped with a Gemini C18 AXIA, 50×21 mm, 5 μm column (Phenomenex®); mobile phase (A: NH4HCO3 10 mM aq. sol, pH=10; B: CH3CN), flow rate=17 ml/min; UV wavelength range: 210-350 nm; gradient 35% (B) to 40% (B) in 1 min, 40% (B) to 70% (B) in 7 min, 70% (B) to 100% (B) in 1 min, 100% (B) for 1.5 min). After evaporation of the solvent the compound recovered (23 mg, 0.047 mmol) was dissolved in DCM (1 ml) and treated with HCl (0.041 ml of a 1.25 M solution in methanol, 0.12 mmol). The resulting mixture was stirred at room temperature for 0.5 hour. Evaporation of the solvent and trituration with diethyl ether (2×3 ml) gave the hydrochloride salt of the title compound. The title compound was then recovered (13 mg, 0.027 mmol, 6%) after passage through SCX (2 g) cartridge (eluting with methanol followed by 2N ammonia solution in methanol).

MS (ES) (m/z): 488 [MH$^+$]; C$_{26}$H$_{25}$F$_4$N$_3$O$_2$ requires 488.5
$^1$H-NMR (CDCl$_3$) δ ppm 8.15 (br. s., 1 H) 7.54 (d, 2 H) 7.17-7.24 (m, 3 H) 7.11 (dd, 1 H) 6.99 (dd, 1 H) 6.93 (td, 1 H) 3.87 (t, 2 H) 3.31 (d, 1 H) 3.07 (d, 1 H) 2.56-2.64 (m, 3H) 2.45-2.54 (m, 1 H) 2.26-2.29 (m, 3 H) 1.89-1.99 (m, 2 H) 1.75-1.83 (m, 1 H) 1.33-1.41 (m, 1 H) 0.80-0.89 (m, 1 H)

Examples 52-55

The following examples (E52-E55) were prepared using a similar procedure as set out earlier in (Example 51) starting from the appropriate boronic acid and 5-Iodo-1-{3-[(1S,5R)-1-(4-trifluoromethyl-phenyl)-3-aza-bicyclo[3.1.0]hex-3-yl]-propyl}-1H-pyrimidine-2, 4-dione (Prep40). Boronic acids used are all commercially available (from Aldrich or Alfa Aesar)

| Examples | Analytical data ([MH]$^+$, $^1$H NMR) |
|---|---|
| Example 52<br>5-[2-(1-methylethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione | MS (ES) (m/z): 498 [MH$^+$]; C$_{28}$H$_{30}$F$_3$N$_3$O$_2$ requires 497.56<br>$^1$H-NMR (CDCl$_3$) δ ppm 8.16(br.s., 1H)7.54(d, 2H)7.37-7.41(m, 2H)7.20(d, 2H)7.17-7.25(m, 2H)7.08-7.12(m, 1H)3.88(t, 2H)3.27-3.37(m, 1H)3.02-3.15(m, 1H)2.83-2.96(m, 1H)2.40-2.67(m, 4H)1.87-2.00(m, 2H)1.71-1.84(m, 1H)1.34-1.44(m, 1H)1.12-1.29(m, 6H)0.76-0.90(m, 1H) |
| Example 53<br>5-(4-chloro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione | MS (ES) (m/z): 504 [MH$^+$]; C$_{26}$H$_{25}$ClF$_3$N$_3$O$_2$ requires 503.95<br>$^1$H-NMR (CDCl$_3$) δ ppm 8.20(br.s., 1H)7.54(d, 2H)7.16-7.24(m, 4H)7.08(d, 1H)3.88(td, 2H)3.31(d, 1H)3.08(d, 1H)2.55-2.66(m, 3H)2.48-2.54(m, 1H)2.20-2.30(m, 3H)1.89-1.99(m, 3H)1.75-1.82(m, 1H)1.33-1.39(m, 1H)0.81-0.89(m, 1H) |
| Example 54<br>5-[2-(trifluoromethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione | MS (ES) (m/z): 524 [MH$^+$]; C$_{26}$H$_{23}$F$_6$N$_3$O$_2$ requires 523.47<br>$^1$H-NMR (CDCl$_3$) δ ppm 8.18(br.s., 1H)7.78(d, 1H)7.57-7.65(m, 1H)7.50-7.57(m, 3H)7.35-7.42(m, 1H)7.15-7.26(m, 3H)3.88(t, 2H)3.24-3.34(m, 1H)3.03-3.10(m, 1H)2.53-2.64(m, 3H)2.45-2.53(m, 1H)1.87-1.99(m, 2H)1.72-1.81(m, 1H)1.34-1.42(m, 1H)0.77-0.87(m, 1H) |
| Example 55<br>5-{2-[(trifluoromethyl)oxy]phenyl}-1-(3-{(1S,5R)-1-[4-(trifluoromethyl)phenyl]-3-azabicyclo[3.1.0]hex-3-yl}propyl)-2,4(1H,3H)-pyrimidinedione | MS (ES) (m/z): 540 [MH$^+$]; C$_{26}$H$_{23}$F$_6$N$_3$O$_3$ requires 539.47<br>$^1$H-NMR (CDCl$_3$) δ ppm 8.19(br.s., 1H)7.54(d, 2H)7.48(dd, 1H)7.40(dd, 4H)7.20(d, 2H)3.90(t, 2H)3.31(d, 1H)3.08(d, 1H)2.59(d, 3H)2.49(d, 1H)1.89-1.98(m, 2H)1.74-1.82(m, 1H)1.36-1.44(m, 1H)0.80-0.88(m, 1H) |

Example 56

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione (E56)

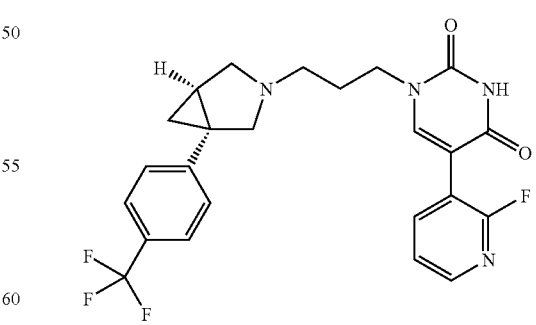

To a solution of 1-[3,3-bis(methyloxy)propyl]-5-(2-fluoro-3-pyridinyl)-2,4(1H,3H)-pyrimidinedione (Prep89, 133 mg, 0.430 mmol) in Tetrahydrofuran (THF) (4 ml) at ambient temperature under an Argon atmosphere, hydrochloric acid 2M solution (0.5 ml, 1.000 mmol) was added and the reaction mixture stirred for 5 h. Volatiles were evaporated at rotary (cold bath) and the residue was taken up with triethylamine (0.240 ml, 1.720 mmol) and 4 ml of THF and the slurry was re-evaporated to dryness. The crude obtained was directly used in the next step without any further purification. It was diluted with Acetonitrile (4.00 ml) and to the mixture was added acetic acid (0.025 ml, 0.430 mmol) followed by (1S,5R)-1-(4-trifluoromethyl-phenyl)-3-aza-bicyclo[3.1.0]hexane (Prep4, 98 mg, 0.430 mmol). The resulting mixture stirred at ambient temperature under an Argon atmosphere for 20 minutes then the mixture was cooled down to 0° C. and sodium triacetoxyboronhydride (137 mg, 0.645 mmol) was added in one portion. The reaction mixture was stirred overnight allowing the Temperature to reach gradually ambient. Reaction mixture was diluted with NaHCO₃ saturated solution (5 mL) and extracted with AcOEt (3×20 mL). Combined organics were dried over Na₂SO₄ and evaporated to dryness to get crude material as thick yellow oil (300 mg) that was purified by SiO₂ flash chromatography eluting with AcOEt/NH₄OH from 100/0 to 96/4 (TLC Rf=0.35 AcOEt/NH4OH 96/4). Evaporation of the solvent afforded the title compound (190 mg) as white foam.

MS (ES) (m/z): 475.1 [M+H]⁺. ¹H-NMR (CDCl₃, 500 MHz) δ: 8.69 (s, 1 H), 8.20 (m, 2 H), 7.70 (s, 1 H), 7.53 (d, 2 H), 7.28 (m, 1 H), 7.20 (d, 2 H), 3.93 (m, 2 H), 3.34 (d, 1 H), 3.10 (d, 1 H), 2.59 (m, 3 H), 2.49 (dd, 1 H), 1.95 (m, 2 H), 1.79 (m, 1 H), 1.43 (t, 1 H), 0.87 (dd, 1 H).

Example 57

5-(2-fluoro-3-pyridinyl)-1-(3-{(1S)-1-[4-(trifluoromethyl)phenyl]-3-azabicyclo[3.1.0]hex-3-yl}propyl)-2,4(1H,3H)-pyrimidinedione dihydrochloride (E57)

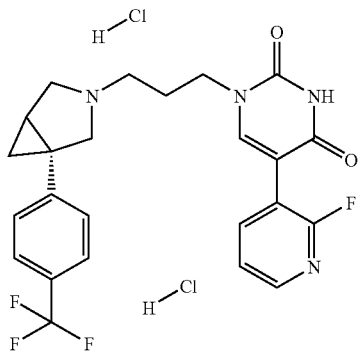

2.0 g of 5-Iodo-1-{3-[(1S,5R)-1-(4-trifluoromethyl-phenyl)-3-aza-bicyclo[3.1.0]hex-3-yl]-propyl}-1H-pyrimidine-2,4-dione (Prep40) were split in 10 batches of 200 mg of 5-iodo-1-(3-{(1S,5R)-1-[4-(trifluoromethyl)phenyl]-3-azabicyclo[3.1.0]hex-3-yl}propyl)-2,4(1H,3H)-pyrimidinedione each.

For each batch 5-iodo-1-(3-{(1S,5R)-1-[4-(trifluoromethyl)phenyl]-3-azabicyclo[3.1.0]hex-3-yl}propyl)-2,4(1H,3H)-pyrimidinedione (200 mg, 0.396 mmol), (2-fluoro-3-pyridinyl)boronic acid (335 mg, 2.375 mmol) and potassium fluoride (207 mg, 3.56 mmol) were dissolved in degassed MeOH (5 mL). Then in each batch palladium(II) acetate (25 mg, 12.5% weight) was added and the mixture was submitted to microwave irradiation for 15 minutes at 100° C. The reaction mixtures were submitted again to microwave irradiation (5 minutes at 100° C.).

Then all batches were filtered on a pad of celite and combined in a single batch.

The solvent was eliminated under reduced pressure and the residue was partitioned between AcOEt and brine, filtered to remove the emulsion and separated. Organic phase was dried over Na₂SO₄. Solvent was eliminated under reduced pressure and the residue was purified with SCX cartridge providing 1.6 g of yellow foam which was further purified by flash chromatography (eluent: AcOEt with 0.25% of NH4OH) providing (5-(2-fluoro-3-pyridinyl)-1-(3-{(1S,5R)-1-[4-(trifluoromethyl)phenyl]-3-azabicyclo[3.1.0]hex-3-yl}propyl)-2,4 (1H,3H)-pyrimidinedione (712 mg, 1.501 mmol, 37.9% yield) as a white powder.

¹H-NMR (CDCl₃) δ: 8.20 (m, 3 H), 7.70 (s, 1H), 7.54 (d, 2H), 7.22 (d, 2H), 3.94 (m, 2H), 3.34 (d, 1H), 3.10 (d, 1H), 2.60 (m, 3H), 2.50 (m, 1H), 1.96 (m, 2H), 1.80 (m, 1H), 1.43 (m, 1H), 0.87 (m, 1H)

The latter was dissolved in 1,4-dioxane and 2.2 eq (825 μL) of HCl 4,0M in 1,4-dioxane were added to the solution. Solvent was eliminated under reduced pressure giving an orange powder which was then triturated with Et₂O and filtered. Salt was further purified by dissolving it in MeOH and converting it again into free base with SCX cartridge. The white solid thus obtained was dissolved in Et₂O and 1,4-dioxane and 2.2 eq of HCl (1N solution in Et₂O; 3.3 mL) were added dropwise. Solution was filtered providing 629.6 mg of the title compound (29% yield) as a white powder.

MS (ES) (m/z): 475 [M+H]⁺. ¹H-NMR (DMSO-d₆) δ: 8.21 (m, 1 H), 8.04 (s, 1H), 8.00 (m, 1H), 7.70 (d, 2H), 7.48 (d, 2H), 7.42 (m, 1H), 4.05 (m, 1H), 3.83 (m, 2H), 3.73 (m, 1H), 3.62 (m, 1H), 3.50 (m, 1H), 3.30 (m, 2H), 2.29 (m, 1H), 2.10 (m, 2H), 1.63 (m, 1H), 1.14 (m, 1H) [α]²⁴_D −51.11 (c=1, MeOH)

Example 58

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione (E58)

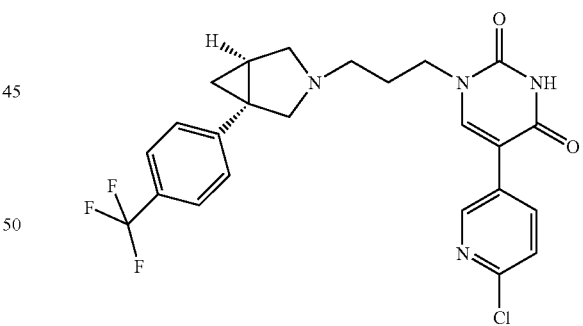

A solution of 3-[5-(6-Chloro-pyridin-3-yl)-2,4-dioxo-3,4-dihydro-2H-pyrimidin-1-yl]-propionaldehyde (Prep93, 0.82 mmol), (1S,5R)-1-(4-trifluoromethyl-phenyl)-3-aza-bicyclo [3.1.0]hexane (Prep4, 186 mg, 0.82 mmol), and AcOH (58 μl) in dichloroethane-MeOH (10-0.1, 8 ml) was cooled to 0° C. NaBH(AcO)₃ (182 mg, 0.86 mmol) was added portionwise. The mixture was stirred at 0° C. for further one hour and then basified with 1N NaOH. Brine was added and the product extracted with DCM. The organic phase was dried (Na₂SO₄) and evaporated. The residue was redissolved in DCM and stirred overnight in the presence of PS-isocyanate. The mixture was filtered and the solvent evaporated. The crude was purified by flash chromatography eluting with DCM-MeOH—NH₄OH (98:2:0.2) to give 140 mg of the title compound (34% yield).

MS (ES) (m/z): 491.17 [M+H]⁺. ¹H-NMR (DMSO-d₆, TFA) δ: 11.67 (s, 1 H), 9.72 (br. s., 1 H), 8.62 (d, 1 H), 8.17 (s, 1 H), 8.09 (dd, 1 H), 7.70 (m, 2 H), 7.56 (d, 1 H), 7.49 (m, 2 H), 4.01-4.25 (m, 1 H), 3.86 (t, 2H), 3.70-3.81 (m, 1 H), 3.66 (dd, 1 H), 3.45-3.58 (m, 1 H), 3.19-3.44 (m, 2 H), 2.22-2.41 (m, 1 H), 1.90-2.22 (m, 2 H), 1.39 (dd, 1 H), 1.24 (dd, 1 H).

Example 59

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E59)

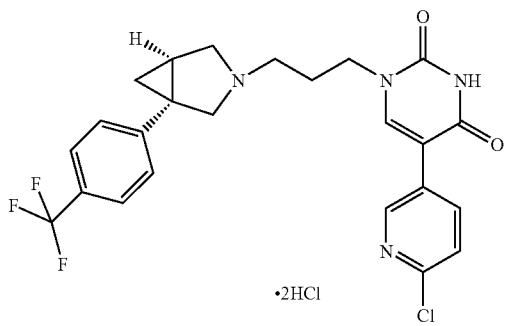

5-(6-chloro-3-pyridinyl)-1-(3-{(1S,5R)-1-[4-(trifluoromethyl)phenyl]-3-azabicyclo[3.1.0]hex-3-yl}propyl)-2,4(1H, 3H)-pyrimidinedione (E58, 31 mg, 0.06 mmol) was suspended in 1 ml of dioxane and 4M HCl in dioxane solution (31 μl, 0.12 mmol) was added. The mixture was stirred at room temperature for 5 minutes, and then the solvent was removed in vacuum to give 33 mg of the title compound as an off-white powder (94%, yield).

MS (ES) (m/z): 491.17 [M+H]⁺. ¹H-NMR (DMSO-d₆) δ: 11.66 (s, 1 H), 10.34 (br. s., 1 H), 8.63 (d, 1 H), 8.20 (s, 1 H), 8.10 (dd, 1 H), 7.70 (m, 2 H), 7.56 (d, 1 H), 7.49 (m, 2 H), 4.06 (dd, 1 H), 3.87 (t, 2 H), 3.39-3.79 (m, 5 H), 2.22-2.37 (m, 1 H), 1.99-2.22 (m, 2 H), 1.66 (dd, 1 H), 1.06-1.32 (m, 1 H).

Example 60

5-(2-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E60)

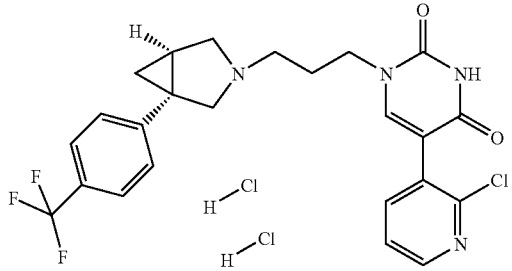

A solution of 3-[5-(2-chloro-pyridin-3-yl)-2,4-dioxo-3,4-dihydro-2H-pyrimidin-1-yl]-propionaldehyde (Prep97, 128 mg, 0.46 mmol), (1S,5R)-1-(4-trifluoromethyl-phenyl)-3-aza-bicyclo[3.1.0]hexane (Prep4, 104 mg, 0.46 mmol), and AcOH (32 μl) in dichloroethane-MeOH (10-01, 4 ml) was cooled to 0° C. NaBH(AcO)₃ (102 mg, 0.48 mmol) was added portionwise. The mixture was stirred at 0° C. for further 1 hour and then basified with 1N NaOH. The product was extracted with DCM. The organic phase was dried (Na₂SO₄) and evaporated. The crude was purified by flash chromatography eluting with DCM-MeOH—NH4OH (98:2:0.2) to give 77 mg of the free base of title compound (34% yield).

5-(2-chloro-3-pyridinyl)-1-(3-{(1S,5R)-1-[4-(trifluoromethyl)phenyl]-3-azabicyclo[3.1.0]hex-3-yl}propyl)-2,4(1H, 3H)-pyrimidinedione was dissolved in dioxane (1 ml) and treated with 4N HCl in dioxane solution (78 μl 0.31 mmol), to give 86 mg of the title compound as a off-white powder (98% yield).

MS (ES) (m/z): 491.10 [M+H]⁺. ¹H-NMR (DMSO-d₆) δ: 11.63 (s, 1 H), 10.71 (br. s., 1 H), 8.42 (dd, 1 H), 7.97 (s, 1 H), 7.85 (dd, 1 H), 7.70 (m, 2 H), 7.50 (m, 2 H), 7.42-7.50 (m, 1 H), 4.06 (dd, 1 H), 3.84 (t, 2 H), 3.73 (dd, 1 H), 3.58-3.67 (m, 1 H), 3.42-3.54 (m, 1 H), 3.10-3.31 (m, 2 H), 2.24-2.35 (m, 1 H), 2.02-2.22 (m, 2 H), 1.77 (dd, 1 H), 1.19 (dd, 1 H).

Example 61

5-(2-fluoro-5-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E61)

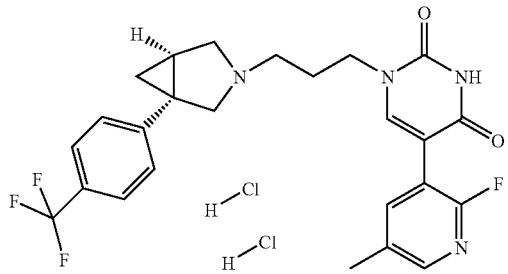

A solution of 3-[5-(2-fluoro-5-methyl-pyridin-3-yl)-2,4-dioxo-3,4-dihydro-2H-pyrimidin-1-yl]-propionaldehyde (Prep101, 150 mg, 0.54 mmol), (1S,5R)-1-(4-trifluoromethyl-phenyl)-3-aza-bicyclo[3.1.0]hexane (Prep4, 104 mg, 0.46 mmol), and AcOH (32 mg) in dichloroethane (3 ml) was cooled to 0° C. NaBH(AcO)₃ (172 mg, 0.81 mmol) was added portionwise. The mixture was stirred at 0° C. for one hour and then basified with 2N NaOH. The product was extracted with ethyl acetate, the organic phase washed with brine, dried (Na₂SO₄) and evaporated to give 150 mg of a colorless oil. The crude was purified by preparative LC-MS. The so obtained trifluoroacetate salt was passed over a SCX cartridge to give 48 mg of the title compound (19% yield).

5-(2-fluoro-5-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in dioxane (1 ml) and treated with 4N HCl in dioxane solution (2 eq), to give 59 mg of the title compound.

MS (ES) (m/z): 489.22 [M+H]⁺. ¹H-NMR (DMSO-d₆, TFA) δ: 11.62 (s, 1 H), 10.84 (br. s., 1 H), 8.02-8.06 (m, 1 H), 8.01 (s, 1 H), 7.83 (dd, 1 H), 7.69 (m, 2 H), 7.49 (m, 2 H), 4.05 (dd, 1 H), 3.84 (t, 2 H), 3.72 (dd, 1 H), 3.57-3.66 (m, 1 H), 3.43-3.55 (m, 1 H), 3.17-3.34 (m, 2 H), 2.31 (s, 3 H), 2.22-2.30 (m, 1 H), 2.04-2.22 (m, 2 H), 1.80 (dd, 1 H), 1.18 (dd, 1 H)

Example 62

3-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile (E62)

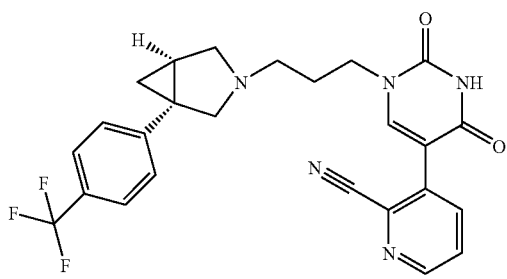

A solution of 3-[2,4-dioxo-1-(3-oxo-propyl)-1,2,3,4-tetrahydro-pyrimidin-5-yl]-pyridine-2-carbonitrile (Prep105, 130 mg, 0.48 mmol), (1S,5R)-1-(4-trifluoromethyl-phenyl)-3-aza-bicyclo[3.1.0]hexane (Prep4, 87 mg, 0.38 mmol), and AcOH (29 mg, 0.48 mmol) in dichloroethane (3 ml) was cooled to 0° C. NaBH(AcO)$_3$ (153 mg, 0.72 mmol) was added portionwise. The mixture was stirred at 0° C. for one hour and then basified with 1N NaOH. The product was extracted with ethyl acetate, the organic phase washed with brine, dried (Na$_2$SO$_4$) and evaporated to give 180 mg of an oil. The crude was dissolved in DCM and treated with PS-isocyanate (250 mg) at room temperature overnight, filtered and evaporated. The residue was purified by flash chromatography eluting with DCM-MeOH—NH$_4$OH (95-5-05) to give 40 mg of an oil that was further purified by preparative LC-MS. The so obtained trifluoroacetate salt was passed over a SCX cartridge to give 13 mg of the title compound (7% yield).
MS (ES) (m/z): 482.2 [M+H]$^+$.

Example 63

5-(2-chloro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E63)

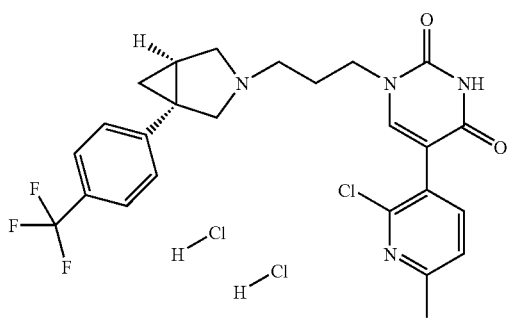

A solution of 3-[5-(2-chloro-6-methylpyridin-3-yl)-2,4-dioxo-3,4-dihydro-2H-pyrimidin-1-yl]-propionaldehyde (Prep109, 78 mg, 0.26 mmol), (1S,5R)-1-(4-trifluoromethyl-phenyl)-3-aza-bicyclo[3.1.0]hexane (Prep4, 60 mg, 0.26 mmol), and AcOH (19 µl) in dichloroethane (4 ml) was cooled to 0° C. NaBH(AcO)$_3$ (58 mg, 0.26 mmol) was added portionwise. The mixture was stirred at 0° C. for further 2 hours and then basified with 1N NaOH. The product extracted with DCM, the organic phase was dried (Na$_2$SO$_4$) and evaporated. The residue was redissolved in DCM and stirred overnight in presence of PS-isocyanate. The mixture was filtered and the solvent was evaporated. The crude was purified by flash chromatography eluting with DCM-MeOH—NH$_4$OH (98:2:0.2) and then was passed over a SCX cartridge to give 20 mg of the free base of title compound (15% yield).

5-(2-chloro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was treated with 4N HCl in dioxane solution (2 eq) to give 22 mg of the title compound.

MS (ES) (m/z): 505.18 [M+H]$^+$. $^1$H-NMR (DMSO-d$_6$, TFA) δ: 11.59 (s, 1 H), 10.55 (br. s., 1 H), 7.91 (s, 1 H), 7.63-7.78 (m, 3 H), 7.50 (m, 2 H), 7.33 (d, 1 H), 4.07 (dd, 1 H), 3.83 (t, 2 H), 3.73 (dd, 1 H), 3.58-3.67 (m, 1 H), 3.45-3.56 (m, 1 H), 3.14-3.33 (m, 2 H), 2.49 (s, 3 H), 2.23-2.35 (m, 1 H), 2.12 (quin, 2 H), 1.72 (dd, 1 H), 1.19 (dd, 1 H)

Example 64

5-(4-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E64)

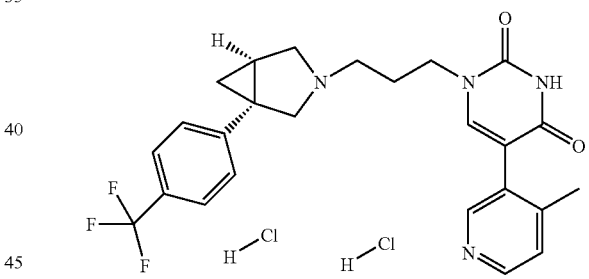

A solution of 3-[5-(4-Methyl-pyridin-3-yl)-2,4-dioxo-3,4-dihydro-2H-pyrimidin-1-yl]-propionaldehyde (Prep113, 84 mg, 0.32 mmol), (1S,5R)-1-(4-trifluoromethyl-phenyl)-3-aza-bicyclo[3.1.0]hexane (Prep4, 74 mg, 0.32 mmol), and AcOH (23 µl) in dichloroethane (4 ml) was cooled to 0° C. NaBH(AcO)$_3$ (72 mg, 0.34 mmol) was added portionwise. The mixture was stirred at 0° C. for 2 hours and at room temperature for 30 minutes and then basified with 1N NaOH. The product was extracted with DCM, the organic phase was dried (Na$_2$SO$_4$) and evaporated. The residue was redissolved in DCM and stirred for 5 hours in presence of PS-isocyanate. The mixture was filtered and the solvent was evaporated. The crude was purified by flash chromatography eluting with DCM-MeOH—NH$_4$OH (98:2:0.2) to give 41 mg of the free base of title compound (27% yield).

5-(4-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione was suspended in dioxane (2 ml) and treated with a 4N HCl in dioxane solution (2 eq) to give the title compound as a white solid.

MS (ES) (m/z): 471.22 [M+H]$^+$. $^1$H-NMR (DMSO-d$_6$) δ: 11.57 (s, 1 H), 10.67 (br. s., 1 H), 8.45 (d, 1 H), 8.37 (s, 1 H), 7.87 (s, 1 H), 7.70 (m, 2 H), 7.49 (m, 2 H), 7.35 (d, 1 H), 4.06 (dd, 1 H), 3.84 (t, 2 H), 3.73 (dd, 1 H), 3.58-3.67 (m, 1 H), 3.38-3.56 (m, 3 H), 2.26-2.35 (m, 1 H), 2.26 (s, 3 H), 2.02-2.20 (m, 2 H), 1.76 (dd, 1 H), 1.19 (dd, 1 H)

Example 65

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione (E65)

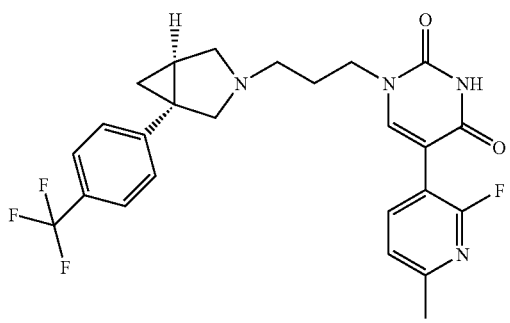

A solution of 3-[5-(2-fluoro-6-methyl-pyridin-3-yl)-2,4-dioxo-3,4-dihydro-2H-pyrimidin-1-yl]-propionaldehyde (Prep117, 0.46 mmol), (1S,5R)-1-(4-trifluoromethyl-phenyl)-3-aza-bicyclo[3.1.0]hexane (Prep4, 104 mg, 0.46 mmol), and AcOH (32 µl) in dichloroethane-MeOH (10-0.5, 4 ml) was cooled to 0° C. NaBH(AcO)$_3$ (102 mg, 0.48 mmol) was added portionwise. The mixture was stirred at 0° C. for one hour and then basified with 1N NaOH. The product was extracted with DCM. The organic phase was dried (Na$_2$SO$_4$) and evaporated. The residue was redissolved in DCM and stirred overnight in the presence of PS-isocyanate (300 mg). The mixture was filtered and the solvent evaporated. The crude was purified by flash chromatography eluting with DCM-MeOH—NH$_4$OH (98-2-0.2) and then SCX cartridge to give 90 mg of the title compound (40% yield).

MS (ES) (m/z): 489.19 [M+H]$^+$.

Example 66

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione dihydrochloride (E66).

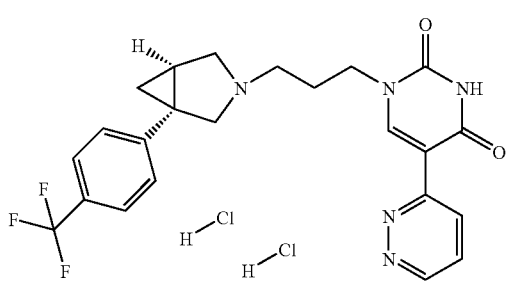

A solution of 3-(2,4-dioxo-5-pyridazin-3-yl-3,4-dihydro-2H-pyrimidin-1-yl)-propionaldehyde hydrochloride (Prep123, 100 mg, 0.35 mmol), (1S,5R)-1-(4-trifluoromethyl-phenyl)-3-aza-bicyclo[3.1.0]hexane (Prep4, 80 mg, 0.35 mmol), and AcOH (21 mg, 0.35 mmol) in dichloroethane-MeOH (1-1, 4 ml) was cooled to 0° C. NaBH(AcO)$_3$ (83 mg, 0.39 mmol) was added portionwise. The mixture was stirred at 0° C. for further one hour and then basified with 1N NaOH. The product was extracted with ethyl acetate. The organic phase was dried (Na$_2$SO$_4$) and evaporated. The residue was redissolved in DCM and stirred for 72 hours in the presence of PS-isocyanate (300 mg). The mixture was filtered and the solvent evaporated. The crude was triturated with diethyl ether to give 20 mg the free base of title compound (12% yield).

5-(3-pyridazinyl)-1-(3-{(1S,5R)-1-[4-(trifluoromethyl)phenyl]-3-azabicyclo[3.1.0]hex-3-yl}propyl)-2,4(1H,3H)-pyrimidinedione was dissolved in MeOH and treated with 4N HCl in dioxane solution (2 eq). The solvent was evaporated and the residue triturated with diethyl ether to afford 31 mg of the title compound.

MS (ES) (m/z): 458.16 [M+H]$^+$. $^1$H-NMR (DMSO-d$_6$, TFA) δ: 11.87 (s, 1 H), 11.29 (br. s., 1 H), 9.72 (dd, 1 H), 9.32 (dd, 1 H), 8.83 (s, 1 H), 8.38 (dd, 1 H), 7.64-7.77 (m, 2 H), 7.45-7.56 (m, 2 H), 3.95 (t, 2 H), 3.43-3.76 (m, 4 H), 3.19-3.35 (m, 2 H), 2.15-2.32 (m, 3 H), 1.96 (dd, 1 H), 1.16 (dd, 1 H).

Example 67

5-(2-pyrazinyl)-1-(3-{(1S,5R)-1-[4-(trifluoromethyl)phenyl]-3-azabicyclo[3.1.0]hex-3-yl}propyl)-2,4(1H,3H)-pyrimidinedione (E67)

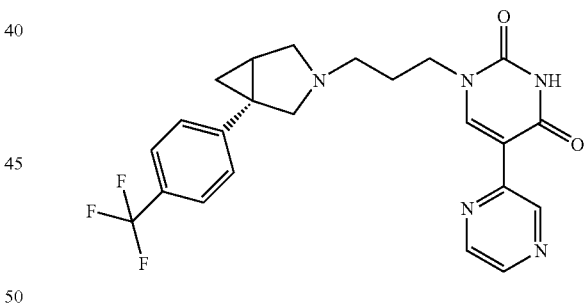

A solution of 3-(2,4-dioxo-5-pyrazin-2-yl-3,4-dihydro-2H-pyrimidin-1-yl)-propionaldehyde (Prep127, 0.38 mmol), (1S,5R)-1-(4-trifluoromethyl-phenyl)-3-aza-bicyclo[3.1.0]hexane (Prep4, 86 mg, 0.38 mmol), and AcOH (26 µl) in dichloroethane-MeOH (10-0.5, 4 ml) was cooled to 0° C. NaBH(AcO)$_3$ (84 mg, 0.40 mmol) was added portionwise. The mixture was stirred at 0° C. for further one hour and then basified with 1N NaOH. The product was extracted with DCM. The organic phase was dried (Na$_2$SO$_4$) and evaporated. The residue was redissolved in DCM and stirred overnight in the presence of PS-isocyanate. The mixture was filtered and the solvent evaporated. The crude was purified by flash chromatography eluting with DCM-MeOH—NH$_4$OH (98-2-0.2) to give 78 mg of the title compound (45% yield).

MS (ES) (m/z): 458.17 [M+H]$^+$.

Example 68

5-(2-pyrazinyl)-1-(3-{(1S,5R)-1-[4-(trifluoromethyl) phenyl]-3-azabicyclo[3.1.0]hex-3-yl}propyl)-2,4(1H, 3H)-pyrimidinedione dihydrochloride (E68)

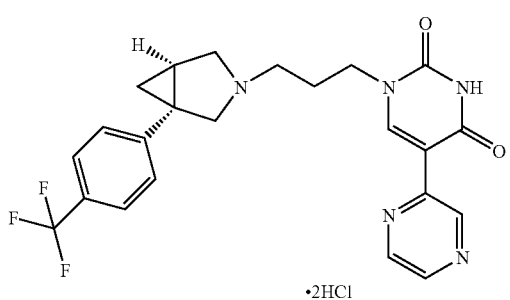

·2HCl 5-(2-pyrazinyl)-1-(3-{(1S,5R)-1-[4-(trifluoromethyl)phenyl]-3-azabicyclo[3.1.0]hex-3-yl}propyl)-2,4(1H,3H)-pyrimidinedione (E67, 78 mg, 0.17 mmol) was dissolved in 2 ml of dioxane and then 4N HCl in dioxane solution (85 µl, 0.34 mmol) was added. The mixture was stirred at room temperature for 5 minutes, and then the solvent was removed in vacuum. The residue was triturated with petroleum ether to give 81.2 mg of the title compound as a yellow solid (90%, yield).

MS (ES) (m/z): 458.17 [M+H]$^+$. $^1$H-NMR (DMSO-d$_6$, TFA) δ: 11.75 (s, 1 H), 10.74 (br. s., 1 H), 9.40 (d, 1 H), 8.64 (dd, 1 H), 8.59 (s, 1 H), 8.54 (d, 1 H), 7.69 (m, 2 H), 7.48 (m, 2 H), 4.04 (dd, 1 H), 3.95 (t, 2 H), 3.71 (dd, 1 H), 3.61 (dd, 1 H), 3.43-3.55 (m, 1 H), 3.18-3.37 (m, 2 H), 2.23-2.29 (m, 1 H), 2.06-2.23 (m, 2 H), 1.76 (dd, 1 H), 1.18 (dd, 1 H)

Example 69

5-(2-fluoro-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione dihydrochloride (E69)

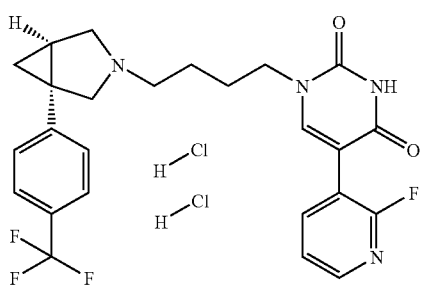

A solution of 1-(4-chloro-butyl)-5-(2-fluoro-pyridin-3-yl)-1H-pyrimidine-2,4-dione (Prep131, 185 mg, 0.62 mmol), (1S,5R)-1-(4-trifluoromethyl-phenyl)-3-aza-bicyclo[3.1.0] hexane (Prep4, 141 mg, 0.62 mmol), and DIPEA (241 mg, 1.87 mmol) in absolute EtOH (4 ml) was heated at 130° C. for 4.5 hours in a microwave oven. The solvent was removed under vacuum and the residue was purified by flash chromatography (DCM-MeOH—NH$_4$OH (95-5-0.5) to give 140 mg of a compound that was further purified by preparative LC-MS. The obtained trifluoroacetate salt was passed over SCX cartridge to give 40 mg of the title compound (13% yield) as a free base.

5-(2-fluoro-3-pyridinyl)-1-(4-{(1S)-1-[4-(trifluoromethyl)phenyl]-3-azabicyclo[3.1.0]hex-3-yl}butyl)-2,4(1H, 3H)-pyrimidinedione was treated with 4N HCl in dioxane (2 eq). After evaporation of the solvent and trituration with diethyl ether, 41 mg of the title compound were obtained as a white powder. (89% yield)

MS (ES) (m/z): 489.22 [M+H]$^+$. $^1$H-NMR (CDCl$_3$) δ: 11.61 (s, 1 H), 10.55 (br. s., 1 H), 8.21 (ddd, 1 H), 8.05 (s, 1 H), 8.02 (ddd, 1 H), 7.70 (m, 2 H), 7.49 (m, 2 H), 7.40 (ddd, 1 H), 4.04 (dd, 1 H), 3.77 (t, 2 H), 3.71 (dd, 1 H), 3.63 (dd, 1 H), 3.44-3.56 (m, 1 H), 3.09-3.33 (m, 2 H), 2.20-2.36 (m, 1 H), 1.50-1.96 (m, 5 H), 1.20 (dd, 1 H)

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. Compound of formula (I)' or a salt thereof:

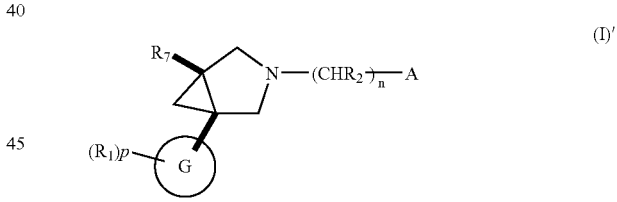

wherein

G is selected from a group consisting of phenyl, a 5- or 6-membered monocyclic heteroaryl group, and a 8- to 11-membered heteroaryl bicyclic group;

A is a group P1 or a group P2 wherein

P1 is

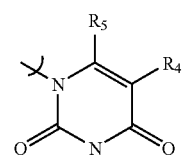

and P2 is

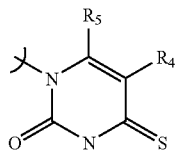

p is an integer ranging from 0 to 5;
$R_1$ is halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or corresponds to a group $R_6$; and when p is an integer ranging from 2 to 5, each $R_1$ may be the same or different;
$R_2$ is hydrogen or $C_{1-4}$alkyl;
n is 3, 4, 5 or 6;
$R_6$ is selected from the group consisting of isoxazolyl, —$CH_2$—N-pyrrolyl, 1,1-dioxido-2-isothiazolidinyl, thienyl, thiazolyl, pyridyl, and 2-pyrrolidinonyl, wherein the $R_6$ group is optionally substituted by one or two substituents selected from the group consisting of halogen, cyano, $C_{1-4}$alkyl, halo$C_{1-4}$alkyl, $C_{1-4}$alkoxy, and $C_{1-4}$alkanoyl;
$R_4$ is selected from the group consisting of hydrogen, halogen, hydroxy, cyano, $C_{1-4}$alkyl, $C_{3-7}$ cycloalkyl, halo$C_{1-4}$ alkyl, $C_{1-4}$alkoxy, halo$C_{1-4}$alkoxy, $C_{1-4}$alkanoyl and NR'R''; or $R_4$ is a phenyl group, a 5-14 membered heterocyclic group; and any of such phenyl or heterocyclic group is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl, halo$C_{1-4}$alkoxy and $SF_5$;
$R_5$ is selected from the group consisting of hydrogen, halogen, hydroxy, cyano, $C_{1-4}$alkyl, $C_{3-7}$ cycloalkyl, halo$C_{1-4}$ alkyl, $C_{1-4}$alkoxy, halo$C_{1-4}$alkoxy, $C_{1-4}$alkanoyl and NR'R''; or $R_5$ is a phenyl group, a 5-14 membered heterocyclic group; wherein the phenyl or heterocyclic groups is optionally substituted by 1, 2, 3 or 4 substituents selected from the group consisting of halogen, cyano, $C_{1-4}$alkyl, halo$C_{1-4}$alkyl, $C_{1-4}$alkoxy, $C_{1-4}$alkanoyl and $SF_5$;
$R_7$ is hydrogen or $C_{1-2}$alkyl;
R' is H, $C_{1-4}$ alkyl or $C_{1-4}$ alkanoyl;
R'' is defined as R';
R' and R'' taken together with the interconnecting nitrogen atom may form a 5-, 6-membered saturated or unsaturated heterocyclic ring; wherein at least one of $R_4$ and $R_5$ is hydrogen; and wherein only one $R_2$ group may be different from hydrogen.

2. A compound as claimed in claim 1 which is a compound of formula (IA)

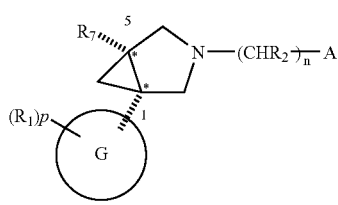

wherein G, A, p, n, $R_1$, $R_2$ and $R_7$ are as defined for compounds of formula (I)', or salts thereof.

3. A compound as claimed in claim 1 which is a compound of formula (IM)

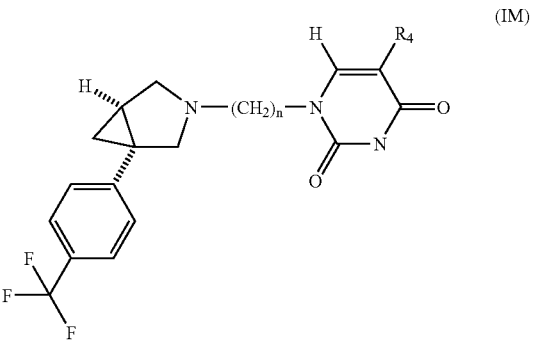

wherein $R_4$ and n are as defined for compounds of formula (I)', or salts thereof.

4. A compound of formula (I)' as claimed in claim 1 selected in the group consisting of:
1-(3-{(1S,5R)-1-[4-(trifluoromethyl)phenyl]-3-azabicyclo[3.1.0]hex-3-yl}propyl)- 2,4(1H,3H)-pyrimidinedione;
5-methyl-1-(3-{(1S,5R)-1-[4-(trifluoromethyl)phenyl]-3-azabicyclo[3.1.0]hex-3-yl}propyl)-2,4(1H,3H)-pyrimidinedione;
5-methyl-1-(4-{(1S,5R)-1-[4-(trifluoromethyl)phenyl]-3-azabicyclo[3.1.0]hex-3-yl}butyl)-2,4(1H,3H)-pyrimidinedione;
5-methyl-1-(4-{(1S,5R/1R,5S)-1-[3-(trifluoromethyl)phenyl]-3-azabicyclo[3.1.0]hex-3-yl}butyl)-2,4(1H, 3H)-pyrimidinedione;
1-(4-{(1S,5R)-1-[4-(trifluoromethyl)phenyl]-3-azabicyclo[3.1.0]hex-3-yl}butyl)- 2,4(1H,3H)-pyrimidinedione;
5-fluoro-1-(3-{(1S,5R)-1-[4-(trifluoromethyl)phenyl]-3-azabicyclo[3.1.0]hex-3-yl}propyl)-2,4(1H,3H)-pyrimidinedione;
5-methyl-1-(5-{(1S,5R)-1-[4-(trifluoromethyl)phenyl]-3-azabicyclo[3.1.0]hex-3-yl}pentyl)-2,4(1H,3H)-pyrimidinedione;
5-phenyl-1-(3-{(1S,5R)-1-[4-(trifluoromethyl)phenyl]-3-azabicyclo[3.1.0]hex-3-yl}propyl)-2,4(1H,3H)-pyrimidinedione;
5-(2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;
5-(1-pyrrolidinyl)-1-(3-{(1S,5R)-1-[4-(trifluoromethyl)phenyl]-3-azabicyclo[3.1.0]hex- 3-yl}propyl)-2,4(1H, 3H)-pyrimidinedione;
5-cyclopropyl-1-(3-{(1S,5R)-1-[4-(trifluoromethyl)phenyl]-3-azabicyclo[3.1.0]hex-3-yl}propyl)-2,4(1H,3H)-pyrimidinedione;
1-(3-{(1S,5R)-1-[2-fluoro-4-(trifluoromethyl)phenyl]-3-azabicyclo[3.1.0]hex-3-yl}propyl)-5-(2-thienyl)-2,4 (1H,3H)-pyrimidinedione;
5-(trifluoromethyl)-1-(3-{(1S,5R)-1-[4-(trifluoromethyl)phenyl]-3-azabicyclo[3.1.0]hex-3-yl}propyl)-2,4(1H, 3H)-pyrimidinedione;
5-(trifluoromethyl)-1-(4-{(1S,5R)-1-[4-(trifluoromethyl)phenyl]-3-azabicyclo[3.1.0]hex-3-yl}butyl)-2,4(1H, 3H)-pyrimidinedione;

5-(3-methyl-2-thienyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-methyl-2-thienyl)-1-(4-{(1S,5R)-1-[4-(trifluoromethyl)phenyl]-3-azabicyclo[3.1.0]hex-3-yl}butyl)-2,4(1H,3H)-pyrimidinedione;

2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinecarbonitrile;

2,4-dioxo-1-(4-{(1S,5R)-1-[4-(trifluoromethyl)phenyl]-3-azabicyclo[3.1.0]hex-3-yl}butyl)-1,2,3,4-tetrahydro-5-pyrimidinecarbonitrile;

5-(2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluorophenyl)-1-(3-{(1S,5R)-1-[4-(trifluoromethyl)phenyl]-3-azabicyclo[3.1.0]hex- 3-yl}propyl)-2,4(1H,3H)-pyrimidinedione;

5-(3,5-dimethyl-4-isoxazolyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methyl-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-pyridazinyl)-1-(3-{(1S,5R)-1-[4-(trifluoromethyl)phenyl]-3-azabicyclo[3.1.0]hex- 3-yl}propyl)-2,4(1H, 3H)-pyrimidinedione;

5-(3-pyridinyl)-1-(3-{(1S,5R)-1-[4-(trifluoromethyl)phenyl]-3-azabicyclo[3.1.0]hex- 3-yl}propyl)-2,4(1H,3H)-pyrimidinedione;

5-(2-methyl-4-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(2-methyl-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-2-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

4-thioxo-1-(4-{(1S,5R)-1-[4-(trifluoromethyl)phenyl]-3-azabicyclo[3.1.0]hex-3-yl}butyl)-3,4-dihydro-2(1H)-pyrimidinone;

5-(2,6-difluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(methyloxy)-3-pyridinyl]-1-(3-{(1S,5R)-1-[4-(trifluoromethyl)phenyl]-3-azabicyclo[3.1.0]hex-3-yl}propyl)-2,4(1H,3H)-pyrimidinedione;

1-(3-{(1R,5R)-1-methyl-5-[4-(trifluoromethyl)phenyl]-3-azabicyclo[3.1.0]hex-3-yl}propyl)-5-[6-(trifluoromethyl)-2-pyridinyl]-2,4(1H,3H)-pyrimidinedione;

5-(5-fluoro-6-methyl-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2,4-dimethyl-1,3-oxazol-5-yl)-1-(4-{(1S,5R)-1-[4-(trifluoromethyl)phenyl]-3-azabicyclo[3.1.0]hex-3-yl}butyl)-2,4(1H,3H)-pyrimidinedione;

5-(5-chloro-2-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(3-fluoro-4-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-5-fluoro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-fluoro-2-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

6-[2,4-dioxo-1-(3-{(1S,5R)-1-[4-(trifluoromethyl)phenyl]-3-azabicyclo[3.1.0]hex-3-yl}propyl)-1,2,3,4-tetrahydro-5-pyrimidinyl]-2-pyridinecarbonitrile;

5-(2-fluoro-3-pyridinyl)-1-(3-{(1S,5R)-1-[2-fluoro-4-(trifluoromethyl)phenyl]-3-azabicyclo[3.1.0]hex-3-yl}propyl)-2,4(1H,3H)-pyrimidinedione;

5-(2-fluoro-3-pyridinyl)-1-(3-{(1S,5R/1R,5S)-1-[3-(trifluoromethyl)phenyl]-3-azabicyclo[3.1.0]hex-3-yl}propyl)-2,4(1H,3H)-pyrimidinedione;

1-{3-[(1S,5R/1R,5S)-1-(4-chlorophenyl)-3-azabicyclo[3.1.0]hex-3-yl]propyl}-5-(2-fluoro-3-pyridinyl)-2,4(1H,3H)-pyrimidinedione;

5-(4-fluoro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(1-methylethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione;

5-(4-chloro-2-methylphenyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-[2-(trifluoromethyl)phenyl]-1-(3-{(1S,5R)-1-[4-(trifluoromethyl)phenyl]-3-azabicyclo[3.1.0]hex-3-yl}propyl)-2,4(1H,3H)-pyrimidinedione;

5-{2-[(trifluoromethyl)oxy]phenyl}-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-fluoro-5-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-chloro-6-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(6-chloro-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

3-[2,4-dioxo-1-(3-{(1S,5R)-1-[4-(trifluoromethyl)phenyl]-3-azabicyclo[3.1.0]hex-3-yl}propyl]-1,2,3,4-tetrahydro-5-pyrimidinyl]-2-pyridinecarbonitrile;

5-(4-methyl-3-pyridinyl)-1-(3-{(1S,5R)-1-[4-(trifluoromethyl)phenyl]-3-azabicyclo[3.1.0]hex-3-yl}propyl)-2,4(1H,3H)-pyrimidinedione;

5-(2-pyrazinyl)-1-(3-{(1S,5R)-1-[4-(trifluoromethyl)phenyl]-3-azabicyclo[3.1.0]hex-3-yl}propyl)-2,4(1H,3H)-pyrimidinedione; and 5-(2-fluoro-3-pyridinyl)-1-(4-{(1S,5R)-1-[4-(trifluoromethyl)phenyl]-3-azabicyclo[3.1.0]hex-3-yl}butyl)-2,4(1H,3H)-pyrimidinedione;

and salts thereof.

5. A method for treating alcohol dependence comprising administering a therapeutically effective amount of a compound of (I)' according to claim 1 or a pharmaceutically acceptable salt thereof to a patient in need thereof, alone or admixed with a pharmaceutically acceptable carrier.

6. A pharmaceutical composition comprising a compound of formula (I)' according to claim 1 or a pharmaceutically acceptable salt thereof, and a pharmaceutically acceptable carrier.

* * * * *